(12) United States Patent
Scadding et al.

(10) Patent No.: US 12,336,553 B2
(45) Date of Patent: Jun. 24, 2025

(54) COMPOSITIONS AND METHODS FOR REDUCING GREENHOUSE GAS

(71) Applicant: Rumin8 Pty Ltd, Mount Pleasant (AU)

(72) Inventors: Cameron Scadding, Landsdale (AU); Rachel Scadding, Landsdale (AU); Silke Jacques, Treeby (AU); Matthew Callahan, Haverford, PA (US)

(73) Assignee: Rumin8 Pty Ltd, Mount Pleasant (AU)

( * ) Notice: Subject to any disclaimer, the term of this patent is extended or adjusted under 35 U.S.C. 154(b) by 0 days.

(21) Appl. No.: 18/125,468

(22) Filed: Mar. 23, 2023

(65) Prior Publication Data

US 2024/0261232 A1    Aug. 8, 2024

Related U.S. Application Data

(60) Provisional application No. 63/444,066, filed on Feb. 8, 2023.

(51) Int. Cl.

| | | |
|---|---|---|
| *A23K 50/10* | (2016.01) | |
| *A23K 10/18* | (2016.01) | |
| *A23K 10/20* | (2016.01) | |
| *A23K 10/28* | (2016.01) | |
| *A23K 10/30* | (2016.01) | |
| *A23K 20/105* | (2016.01) | |
| *A23K 20/121* | (2016.01) | |
| *A23K 20/147* | (2016.01) | |
| *A23K 20/158* | (2016.01) | |
| *A23K 20/163* | (2016.01) | |
| *A23K 40/35* | (2016.01) | |
| *A61K 9/00* | (2006.01) | |
| *A61K 31/02* | (2006.01) | |
| *A61K 31/23* | (2006.01) | |
| *A61K 36/31* | (2006.01) | |
| *A61K 47/14* | (2017.01) | |
| *A61K 47/36* | (2006.01) | |
| *A61P 1/14* | (2006.01) | |

(52) U.S. Cl.
CPC ............. *A23K 50/10* (2016.05); *A23K 10/20* (2016.05); *A23K 10/30* (2016.05); *A23K 20/105* (2016.05); *A23K 20/121* (2016.05); *A23K 20/147* (2016.05); *A23K 20/158* (2016.05); *A23K 20/163* (2016.05); *A61K 9/0056* (2013.01); *A61K 9/0068* (2013.01); *A61K 31/02* (2013.01); *A61K 31/23* (2013.01); *A61K 36/31* (2013.01); *A61K 47/14* (2013.01); *A61P 1/14* (2018.01)

(58) Field of Classification Search
CPC ........ A01G 33/00; A01H 13/00; A23K 10/12; A23K 10/30; A23K 20/105; A23K 40/35; A23K 50/10; Y02A 40/80
See application file for complete search history.

(56) References Cited

U.S. PATENT DOCUMENTS

| | | | |
|---|---|---|---|
| 3,660,562 | A | 5/1972 | Grass, Jr. et al. |
| 4,961,934 | A | 10/1990 | Iwasaki et al. |
| 4,994,284 | A | 2/1991 | Miller |
| 5,972,910 | A | 10/1999 | May et al. |
| 2018/0310592 | A1 | 11/2018 | Embree et al. |
| 2021/0251940 | A1 | 8/2021 | Faris et al. |
| 2022/0031780 | A1* | 2/2022 | De Nys ................. A23K 50/10 |
| 2022/0175670 | A1 | 6/2022 | Lay et al. |
| 2024/0139103 | A1 | 5/2024 | Lay et al. |
| 2024/0252449 | A1 | 8/2024 | Scadding et al. |
| 2024/0260611 | A1 | 8/2024 | Scadding et al. |
| 2024/0261233 | A1 | 8/2024 | Scadding et al. |

FOREIGN PATENT DOCUMENTS

| | | |
|---|---|---|
| AU | 2022100024 A4 | 3/2022 |
| WO | WO-2015109362 A2 | 7/2015 |
| WO | WO-2020113279 A1 | 6/2020 |
| WO | WO-2020243792 A1 | 12/2020 |
| WO | WO-2021205420 A1 | 10/2021 |
| WO | WO-2022136857 A1 | 6/2022 |
| WO | WO-2022221925 A1 | 10/2022 |
| WO | WO-2022232876 A1 | 11/2022 |
| WO | WO-2023010170 A1 | 2/2023 |
| WO | WO-2024165922 A2 | 8/2024 |

OTHER PUBLICATIONS

Natural source D-alpha tocopheryl succinate 1210IU (Wilmatol VES-1210); Wilmar International; one page pdf; downloaded 2023.*
GBA Builders; "Lyophilization 101" (web.archive.org/web/20211201025015/https://www.gbabuilders.com/post/lyophilization-101); web archive retrival of publication on Dec. 1, 2021.*
Ken J.; "How Much Water for Freeze-Dried vs. Dehydrated Food"; Modern Survival Blog; published Oct. 17, 2012.*
Pereira et al; "Enteric methane mitigation strategies in ruminants: a review"; Rev Colomb Cienc Pecu; 28:124-143; 2015.*
Dohme et al.; "Comparative efficiency of various fats rich in medium chain fatty acids to suppress ruminal methanogenesis as measured with RUSITEC."; Can. J. Anim. Sci. 80: 473-482; Sep. 2000.*
Machmuller, Andrea; Agriculture, Ecosystems and Environment 112 (2006); pp. 107-114; published online Oct. 13, 2005.*
Adeyemi et al.,; Italian Journal of Animal Science, 2016; vol. 15, No. 4, pp. 666-672; published online Oct. 31, 2016.*
Adeyemi et al., Anim Sci J. (87); pp. 1137-1147; published online 2015.*
Chagas et al. In Vitro Evaluation of Different Dietary Methane Mitigation Strategies. Animals 2019, 9, 1120. 17 pages.

(Continued)

*Primary Examiner* — Jeffrey T. Palenik
(74) *Attorney, Agent, or Firm* — WILSON SONSINI GOODRICH & ROSATI

(57) ABSTRACT

Provided herein are consumable compositions for methane reduction in ruminants comprising a haloalkane and a medium chain triglyceride (MCT). The use of MCT in the consumable compositions has been found to enhance the anti-methanogenic effect of the consumable compositions in ruminants. Also provided herein are methods of preparing the consumable composition and methods of administering the consumable compositions to ruminants.

20 Claims, 21 Drawing Sheets

(56) References Cited

OTHER PUBLICATIONS

Co-pending U.S. Appl. No. 18/125,474, inventors Scadding; Cameron et al., filed Mar. 23, 2023.
Co-pending U.S. Appl. No. 18/125,476, inventors Scadding; Cameron et al., filed Mar. 23, 2023.
Delle Site. The Vapor Pressure of Environmentally Significant Organic Chemicals: A Review of Methods and Data at Ambient Temperature. J. Phys. Chem. Ref. Data, vol. 26, No. 1, pp. 157-193 (1997).
Durmic et al. In vitro screening of selected feed additives, plant essential oils and plant extracts for rumen methane mitigation. J Sci Food Agric, vol. 94, Issue 6, pp. 1191-1196 (Apr. 2014). First published Sep. 14, 2013. Retrieved at URL: https://www.academia.edu/download/41238439/In_Vitro_Screening_Of_Selected_Feed_Addi20 160114-7158-1ms1iwg.pdf20160115-19908-1kafbad.pdf.
Garcia et al. Essential oils from Lippia turbinata and Tagetes minuta persistently reduce in vitro ruminal methane production in a continuous-culture system. Animal Production Science 59(4) 709-720 (May 24, 2018). Retrieved at URL: https://www.researchgate.net/profile/Maria-Jose-Martinez-3/publication/325339915_Essential_oils_from_Lippia_turbinata_and_Tagetes_minuta_persistently_reduce_in_vitro_ruminal_methane_production_in_a_continuous-culture_system/links/5b070d000f7e9b1ed7edeb8e/Essential-oils-from-Lippia-turbinata-and-Tagetes-minuta-persistently-reduce-in-vitro-ruminal-methane-production-in-a-continuous-culture-system.pdf.
Hino et al. Maintenance of Protozoa and Methanogens, and Fiber Digestion in Rumen-Simulating Continuous Culture. J Gen Appl Microbiol 39, 35-45 (1993).
PCT/AU2022/050836 Written Opinion mailed Sep. 16, 2022.
U.S. Appl. No. 18/125,476 Office Action dated Aug. 30, 2023.
PCT/AU2022/050836 International Search Report mailed Sep. 16, 2022.
Ambrose. Vapor Pressures. In: Le Neindre, et al., eds. In Experimental Thermodynamics of Non-reacting Systems, pp. 607-656. Butterworths, London (1975).
Carson. The measurement of vapor pressure. Ribeiro Da Silva, ed. Thermochemistry and Its Applications to Chemical and Biochemical Systems, pp. 127-141. Riedel Publishing Company (1984).
Durmic et al. In vitro fermentative traits of Australian woody perennial plant species that may be considered as potential sources of feed for grazing ruminants. Animal Feed Science and Technology 160 (2010) 98-109.
Lecithin (emulsifier). AmieSue.com web page. Archived from Oct. 23, 2021. Wayback Machine Archives. Accessed Nov. 15 2023 at URL: https://web.archive.org/web/20211023112624/https://nouveauraw.com/reference-library/ingredient-directory/raw-lecithin-thickener/. 2 pages.
Medium Chain Triglycerides. Ataman Chemicals web page (2015). Accessed Nov. 15, 2023. 9 pages.
Ramin et al. Development of an in vitro method for determination of methane production kinetics using a fully automated in vitro gas system—A modelling approach. Animal Feed Science and Technology 174 (2012) 190-200.
U.S. Appl. No. 18/125,474 Office Action dated Dec. 1, 2023.
Verevkin. Phase changes in pure component systems: Liquids and gases. In Weir et al., eds. Experimental Thermodynamics, vol. 7 pp. 5-30 (2005). Elsevier.
Eugene, M. et al. Meta-analysis on the Effects of Lipid Supplementation on Methane Production in Lactating Dairy Cows. Canadian Journal of Animal Science 88(2):331-334 (2008).
Machmuller, A. et al. Diet composition affects the level of ruminal methane suppression by medium-chain fatty acids. Australian Journal of Agricultural Research 52(7):713-722 (2001).
PCT/IB2024/000064 International Search Report and Written Opinion dated Sep. 25, 2024.
Flores-Santiago et al. Reduction of enteric methane emissions in heifers fed tropical grass-based rations supplemented with palm oil. Fermentation 8(8):349, pp. 1-16 (2022).
Machmuller, et al. Methane suppression by coconut oil and associated effects on nutrient and energy balance in sheep. Canadian Journal of Animal Science 79(1):65-72 (1999).
Richardson and Halick, Moisture in molasses as a factor in the heading of feeds. Texas Agriculture Experiment Station, Texas A&M Bulletin 754, 16 pages (1954).
U.S. Appl. No. 18/125,474 Office Action dated Apr. 15, 2024.
U.S. Appl. No. 18/125,476 Office Action dated Jan. 18, 2024.
U.S. Appl. No. 18/125,476 Office Action dated May 20, 2024.

* cited by examiner

Oil mixed over total mixed ration
Oil mixed over pellets
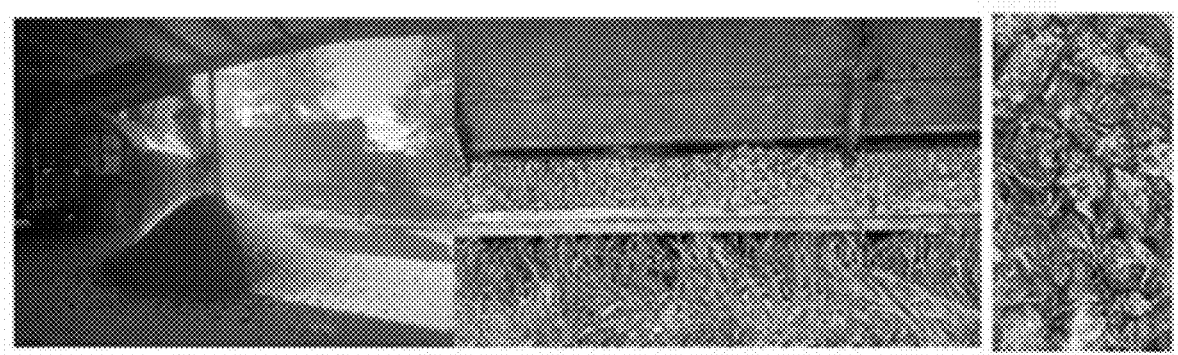
Oil pressed in pellets
FIG. 6

Solid mixed on supplement pellet
Solid mixed in a mineral mix
FIG. 7

| Formulation No. | Dose | Final bromo (mg per vial) | Final conc. (g/kg DM) | % Bioactive/ DM | % CH4 reduction |
|---|---|---|---|---|---|
| 1 | none | 0 | | | |
| | low | 0.015 | 0.03 | 0.003 | 4 |
| | med | 0.075 | 0.15 | 0.015 | 1 |
| | high | 0.15 | 0.3 | 0.03 | 1 |
| 2 | none | 0 | | | |
| | low | 0.015 | 0.03 | 0.003 | 4 |
| | med | 0.075 | 0.15 | 0.015 | 97 |
| | high | 0.15 | 0.3 | 0.03 | 98 |
| 3 | none | 0 | | | |
| | low | 0.015 | 0.03 | 0.003 | 3 |
| | med | 0.075 | 0.15 | 0.015 | 95 |
| | high | 0.15 | 0.3 | 0.03 | 97 |
| 4 | none | 0 | | | |
| | low | 0.015 | 0.03 | 0.003 | 7 |
| | med | 0.075 | 0.15 | 0.015 | 11 |
| | high | 0.15 | 0.3 | 0.03 | 14 |
| 7 | none | 0 | | | |
| | low | 0.015 | 0.03 | 0.003 | 8 |
| | med | 0.075 | 0.15 | 0.015 | 19 |
| | high | 0.15 | 0.3 | 0.03 | 97 |
| 9 | none | 0 | 0.00 | 0 | |
| | very low | 0.02 | 0.04 | 0.004 | 26 |
| | | 0.04 | 0.08 | 0.008 | 23 |
| | | 0.06 | 0.12 | 0.012 | 98 |
| | | 0.08 | 0.16 | 0.016 | 98 |
| | | 0.1 | 0.20 | 0.02 | 98 |
| | | 0.12 | 0.24 | 0.024 | 97 |
| | | 0.14 | 0.28 | 0.028 | 98 |
| | | 0.2 | 0.40 | 0.04 | 98 |
| | very high | 0.3 | 0.60 | 0.06 | 98 |
| 10 | 0 | 0 | 0.00 | 0 | |
| | very low | 0.02 | 0.04 | 0.004 | 11 |
| | | 0.04 | 0.08 | 0.008 | 76 |
| | | 0.06 | 0.12 | 0.012 | 95 |
| | | 0.08 | 0.16 | 0.016 | 94 |
| | | 0.1 | 0.20 | 0.02 | 98 |
| | | 0.12 | 0.24 | 0.024 | 99 |
| | | 0.14 | 0.28 | 0.028 | 98 |
| | | 0.2 | 0.40 | 0.04 | 98 |
| | very high | 0.3 | 0.60 | 0.06 | 98 |
| 25 | 0 | 0 | 0 | 0 | |
| | ultra low | 0.04 | 0.008 | 0.0008 | 10 |
| | low | 0.2 | 0.04 | 0.004 | -7 |
| | low | 0.4 | 0.08 | 0.008 | 81 |
| 26 | 0 | 0 | 0 | 0 | |
| | ultra low | 0.04 | 0.008 | 0.0008 | 4 |
| | low | 0.2 | 0.04 | 0.004 | 14 |
| | low | 0.4 | 0.08 | 0.008 | 94 |
| 27 | 0 | 0 | 0.00 | 0 | |
| | very low | 0.02 | 0.04 | 0.004 | 94 |
| | | 0.04 | 0.08 | 0.008 | 96 |
| | | 0.06 | 0.12 | 0.012 | 98 |
| 28 | 0 | 0 | 0.00 | 0 | |
| | very low | 0.02 | 0.04 | 0.004 | 40 |
| | | 0.04 | 0.08 | 0.008 | 96 |
| | | 0.06 | 0.12 | 0.012 | 97 |
| 29 | 0 | 0 | 0.00 | 0 | |
| | very low | 0.02 | 0.04 | 0.004 | 7 |
| | | 0.04 | 0.08 | 0.008 | 36 |
| | low | 0.06 | 0.12 | 0.012 | 81 |

FIG. 8

| No. | Dose | Final bromo (mg) per vial | Final conc. (g/kg DMI) | % Bioactive /DMI | % CH4 reduction |
|---|---|---|---|---|---|
| 27 | 0 | 0 | 0.00 | 0 | |
| | ultra low | 0.002 | 0.004 | 0.0004 | -8 |
| | | 0.008 | 0.016 | 0.0016 | -7 |
| | | 0.02 | 0.04 | 0.004 | 4 |
| | low | 0.04 | 0.08 | 0.008 | 35 |
| 28 | 0 | 0 | 0.00 | 0 | |
| | ultra low | 0.002 | 0.004 | 0.0004 | -7 |
| | | 0.008 | 0.016 | 0.0016 | -6 |
| | | 0.02 | 0.04 | 0.004 | -2 |
| | low | 0.04 | 0.08 | 0.008 | 17 |

FIG. 9

| Formulation No | Dose | Final bromo (mg) per vial | Final conc (g/kg DMI) | % Bioactive /DMI | % CH4 reduction |
|---|---|---|---|---|---|
| 5 | none | 0 | | | |
|   | low | 0.015 | 0.03 | 0.003 | 9 |
|   | med | 0.075 | 0.15 | 0.015 | 95 |
|   | high | 0.15 | 0.3 | 0.03 | 93 |
| 11 | none | 0 | 0.00 | 0 | |
|    | very low | 0.02 | 0.04 | 0.004 | 14 |
|    |          | 0.04 | 0.08 | 0.008 | 95 |
|    |          | 0.06 | 0.12 | 0.012 | 96 |
|    |          | 0.08 | 0.16 | 0.016 | 97 |
|    |          | 0.1  | 0.20 | 0.02  | 96 |
|    |          | 0.12 | 0.24 | 0.024 | 96 |
|    |          | 0.14 | 0.28 | 0.028 | 96 |
|    |          | 0.2  | 0.40 | 0.04  | 97 |
|    | very high | 0.3 | 0.60 | 0.06 | 97 |
| 21 |          | 0     | 0     | 0      |    |
|    | ultra low | 0.004 | 0.008 | 0.0008 | -4 |
|    | low      | 0.02  | 0.04  | 0.004  | 93 |
|    | low      | 0.04  | 0.08  | 0.008  | 95 |
| 22 |          | 0     | 0     | 0      |    |
|    | ultra low | 0.04 | 0.008 | 0.0008 | 1  |
|    | low      | 0.2   | 0.04  | 0.004  | 92 |
|    | low      | 0.4   | 0.08  | 0.008  | 96 |
| 23 |          | 0     | 0     | 0      |    |
|    | ultra low | 0.04 | 0.008 | 0.0008 | 5  |
|    | low      | 0.2   | 0.04  | 0.004  | 88 |
|    | low      | 0.4   | 0.08  | 0.008  | 96 |
| 24 |          | 0     | 0     | 0      |    |
|    | ultra low | 0.04 | 0.008 | 0.0008 | -24 |
|    | low      | 0.2   | 0.04  | 0.004  | -7 |
|    | low      | 0.4   | 0.08  | 0.008  | -21 |
| 31 |          | 0     | 0     | 0.00   | 0  |
|    | very low | 0.02  | 0.04  | 0.004  | 89 |
|    |          | 0.04  | 0.08  | 0.008  | 23 |
|    | low      | 0.06  | 0.12  | 0.012  | 97 |
| 32 |          | 0     | 0     | 0.00   | 0  |
|    | very low | 0.02  | 0.04  | 0.004  | 98 |
|    |          | 0.04  | 0.08  | 0.008  | 97 |
|    | low      | 0.06  | 0.12  | 0.012  | 97 |
| 33 |          | 0     | 0     | 0.00   | 0  |
|    | very low | 0.02  | 0.04  | 0.004  | 90 |
|    |          | 0.04  | 0.08  | 0.008  | 97 |
|    | low      | 0.06  | 0.12  | 0.012  | 98 |

FIG. 10

| No. | Dose | Final bromo (mg) per vial | Final conc (g/kg DMI) | % Bioactive /DMI | % CH4 reduction |
|---|---|---|---|---|---|
| 31 | none | 0 | | | |
| | ultra low | 0.002 | 0.004 | 0.0004 | -5 |
| | | 0.004 | 0.008 | 0.0008 | -6 |
| | | 0.006 | 0.012 | 0.0012 | 0 |
| | | 0.008 | 0.016 | 0.0016 | 1 |
| | | 0.01 | 0.02 | 0.002 | 4 |
| | very low | 0.02 | 0.04 | 0.004 | 87 |
| | | 0.04 | 0.08 | 0.008 | 95 |
| | | 0.06 | 0.12 | 0.012 | 97 |
| | medium | 0.08 | 0.16 | 0.016 | 97 |
| 32 | none | 0 | | | |
| | ultra low | 0.002 | 0.004 | 0.0004 | -7 |
| | | 0.004 | 0.008 | 0.0008 | -5 |
| | | 0.006 | 0.012 | 0.0012 | 1 |
| | | 0.008 | 0.016 | 0.0016 | 4 |
| | | 0.01 | 0.02 | 0.002 | 7 |
| | very low | 0.02 | 0.04 | 0.004 | 90 |
| | | 0.04 | 0.08 | 0.008 | 95 |
| | | 0.06 | 0.12 | 0.012 | 97 |
| | medium | 0.08 | 0.16 | 0.016 | 97 |

FIG. 11

| Formulation No | Dose | Final bromo (mg) per vial | Final conc. (g/kg DMI) | % Bioactive /DMI | % CH4 reduction |
|---|---|---|---|---|---|
| 12 | none | 0 | 0 | 0 | 0 |
| | high | 0.15 | 0.3 | 0.03 | 98 |
| | med | 0.075 | 0.15 | 0.015 | 98 |
| | low | 0.015 | 0.03 | 0.003 | 6 |
| | high-pellet | 0.15 | 0.3 | 0.03 | 98 |
| 13 | none | 0 | 0 | 0 | 0 |
| | high | 0.15 | 0.3 | 0.03 | 98 |
| | med | 0.075 | 0.15 | 0.015 | 15 |
| | low | 0.015 | 0.03 | 0.003 | 0 |
| | high-pellet | 0.15 | 0.3 | 0.03 | 98 |
| 14 | none | 0 | 0 | 0 | 0 |
| | high | 0.15 | 0.3 | 0.03 | 97 |
| | med | 0.075 | 0.15 | 0.015 | 97 |
| | low | 0.015 | 0.03 | 0.003 | 5 |
| | high-pellet | 0.15 | 0.3 | 0.03 | 98 |
| 15 | none | 0 | 0 | 0 | 0 |
| | high | 0.15 | 0.3 | 0.03 | 98 |
| | med | 0.075 | 0.15 | 0.015 | 98 |
| | low | 0.015 | 0.03 | 0.003 | 1 |
| | high-pellet | 0.15 | 0.3 | 0.03 | 98 |
| 17 | none | 0 | 0.00 | 0 | |
| | very low | 0.02 | 0.04 | 0.004 | 97 |
| | | 0.04 | 0.08 | 0.008 | 98 |
| | | 0.06 | 0.12 | 0.012 | 98 |
| | | 0.08 | 0.16 | 0.016 | 98 |
| | | 0.1 | 0.20 | 0.02 | 98 |
| | | 0.12 | 0.24 | 0.024 | 98 |
| | | 0.14 | 0.28 | 0.028 | 98 |
| | | 0.2 | 0.40 | 0.04 | 98 |
| | very high | 0.3 | 0.60 | 0.06 | 98 |
| 18 | 0 | 0 | 0.00 | 0 | |
| | very low | 0.02 | 0.04 | 0.004 | 4 |
| | | 0.04 | 0.08 | 0.008 | -9 |
| | | 0.06 | 0.12 | 0.012 | 8 |
| | | 0.08 | 0.16 | 0.016 | 2 |
| | | 0.1 | 0.20 | 0.02 | -3 |
| | | 0.12 | 0.24 | 0.024 | 0 |
| | | 0.14 | 0.28 | 0.028 | -3 |
| | | 0.2 | 0.40 | 0.04 | 6 |
| | very high | 0.3 | 0.60 | 0.06 | 20 |
| 19 | 0 | 0 | 0.00 | 0 | |
| | very low | 0.02 | 0.04 | 0.004 | 19 |
| | | 0.04 | 0.08 | 0.008 | 13 |
| | | 0.06 | 0.12 | 0.012 | 97 |
| | | 0.08 | 0.16 | 0.016 | 99 |
| | | 0.1 | 0.20 | 0.02 | 97 |
| | | 0.12 | 0.24 | 0.024 | 98 |
| | | 0.14 | 0.28 | 0.028 | 98 |
| | | 0.2 | 0.40 | 0.04 | 98 |
| | very high | 0.3 | 0.60 | 0.06 | 98 |

FIG. 12

| No. | Dose/frequency | Final bromo (mg) per vial | Final conc (g/kg DMI) | % Bioactive /DMI | % CH4 reduction |
|---|---|---|---|---|---|
| After 2 days | | | | | |
| 20 | low - add once | 0.45 | 0.03 | 0.003 | 100 |
| After 7 days | | | | | |
| Control | none | 0 | | | 0 |
| 10 | low - daily | 0.9 | 0.03 | 0.003 | 100 |
| 10 | low - 48 hrs | 0.9 | 0.03 | 0.003 | 75 |
| 20 | low - add once | 0.15 | 0.01 | 0.001 | 100 |
| 29- slow | low - daily | 0.45 | 0.03 | 0.003 | 9 |
| 27- slow | ultra low- 7 days (double dose) | 0.15 | 0.01 | 0.001 | 16 |
| 27- powder | very low- 7 days (double dose) | 0.3 | 0.02 | 0.002 | 36 |
| After 14 days | | | | | |
| Control | none | 0 | | | 0 |
| 10 | low - daily | 0.45 | 0.03 | 0.003 | 100 |
| 10 | low - 48 hrs | 0.45 | 0.03 | 0.003 | 78 |
| 20 | low - add once | 0.15 | 0.01 | 0.001 | 94 |
| 29- slow | low | 0.9 | 0.06 | 0.006 | 10 |
| 27- slow | ultra low- 7 days (double dose) | 0.3 | 0.02 | 0.002 | 14 |
| 27- powder | very low- 7 days (double dose) | 0.6 | 0.04 | 0.004 | 99 |

FIG. 13

| No. | Dose (daily) | Final bromo (mg) per vial | Final conc (g/kg DMI) | % Bioactive /DMI | % CH4 reduction |
|---|---|---|---|---|---|
| After 7 days ||||||
| Control | none | 0 | | | 0 |
| 11 | very low | 0.6 | 0.04 | 0.004 | 100 |
| | low | 1.2 | 0.08 | 0.008 | 100 |
| | medium | 1.8 | 0.12 | 0.012 | 100 |
| 31 | very low | 0.6 | 0.04 | 0.004 | 98 |
| After 14 days ||||||
| Control | none | 0 | | | 0 |
| 11 | very low | 0.6 | 0.04 | 0.004 | 100 |
| | low | 1.2 | 0.08 | 0.008 | 100 |
| | medium | 1.8 | 0.12 | 0.012 | 100 |
| 31 | very low | 0.6 | 0.04 | 0.004 | 98 |

FIG. 14

| No. | Dose | Final bromo (mg) per vial | Final conc (g/kg DMI) | % Bioactive /DMI | % CH4 reduction |
|---|---|---|---|---|---|
| After 2 days ||||||
| 19 | very low | 0.3 | 0.02 | 0.002 | 100 |
|  | low | 0.9 | 0.06 | 0.006 | 100 |
|  | medium | 1.8 | 0.12 | 0.012 | 100 |
| After 7 days ||||||
| 19 | ultra low | 0.03 | 0.002 | 0.0002 | 100 |
|  | very low | 0.16 | 0.011 | 0.0011 | 100 |
|  | low | 0.3 | 0.02 | 0.002 | 99 |
| After 14 days ||||||
| 19 | ultra low | 0.03 | 0.002 | 0.0002 | 99 |
|  | very low | 0.16 | 0.011 | 0.0011 | 99 |
|  | low | 0.3 | 0.02 | 0.002 | 100 |

FIG. 15

| Formulation No | Dose | Final bromo (mg) per vial | Final conc (g/kg DMI) | % Bioactive /DMI | % CH4 reduction |
|---|---|---|---|---|---|
| 9-cow | 0 | 0 | 0.00 | 0 | |
| | very low | 0.02 | 0.04 | 0.004 | 98 |
| | | 0.04 | 0.08 | 0.008 | 99 |
| | | 0.06 | 0.12 | 0.012 | 99 |
| | | 0.08 | 0.16 | 0.016 | 99 |
| | | 0.1 | 0.20 | 0.02 | 99 |
| | | 0.12 | 0.24 | 0.024 | 99 |
| | | 0.14 | 0.28 | 0.028 | 99 |
| | | 0.2 | 0.40 | 0.04 | 92 |
| | very high | 0.3 | 0.60 | 0.06 | 99 |
| 9- sheep | none | 0 | 0.00 | 0 | |
| | very low | 0.02 | 0.04 | 0.004 | 26 |
| | | 0.04 | 0.08 | 0.008 | 23 |
| | | 0.06 | 0.12 | 0.012 | 98 |
| | | 0.08 | 0.16 | 0.016 | 98 |
| | | 0.1 | 0.20 | 0.02 | 98 |
| | | 0.12 | 0.24 | 0.024 | 97 |
| | | 0.14 | 0.28 | 0.028 | 98 |
| | | 0.2 | 0.40 | 0.04 | 98 |
| | very high | 0.3 | 0.60 | 0.06 | 98 |
| 10-cow | 0 | 0 | 0.00 | 0 | |
| | very low | 0.02 | 0.04 | 0.004 | 99 |
| | | 0.04 | 0.08 | 0.008 | 94 |
| | | 0.06 | 0.12 | 0.012 | 99 |
| | | 0.08 | 0.16 | 0.016 | 99 |
| | | 0.1 | 0.20 | 0.02 | 99 |
| | | 0.12 | 0.24 | 0.024 | 99 |
| | | 0.14 | 0.28 | 0.028 | 99 |
| | | 0.2 | 0.40 | 0.04 | 99 |
| | very high | 0.3 | 0.60 | 0.06 | 99 |
| 10- sheep | 0 | 0 | 0.00 | 0 | |
| | very low | 0.02 | 0.04 | 0.004 | 11 |
| | | 0.04 | 0.08 | 0.008 | 76 |
| | | 0.06 | 0.12 | 0.012 | 95 |
| | | 0.08 | 0.16 | 0.016 | 94 |
| | | 0.1 | 0.20 | 0.02 | 98 |
| | | 0.12 | 0.24 | 0.024 | 99 |
| | | 0.14 | 0.28 | 0.028 | 98 |
| | | 0.2 | 0.40 | 0.04 | 98 |
| | very high | 0.3 | 0.60 | 0.06 | 98 |

FIG. 16

| No | Dose | Final bromo (mg) per vial | Final conc (g/kg DMI) | % Bioactive /DMI | % CH4 reduction |
|---|---|---|---|---|---|
| 11-cow | none | 0 | 0.00 | 0 | |
| | very low | 0.02 | 0.04 | 0.004 | 98 |
| | | 0.04 | 0.08 | 0.008 | 99 |
| | | 0.06 | 0.12 | 0.012 | 99 |
| | | 0.08 | 0.16 | 0.016 | 99 |
| | | 0.1 | 0.20 | 0.02 | 99 |
| | | 0.12 | 0.24 | 0.024 | 99 |
| | | 0.14 | 0.28 | 0.028 | 99 |
| | | 0.2 | 0.40 | 0.04 | 99 |
| | very high | 0.3 | 0.60 | 0.06 | 99 |
| 11-sheep | none | 0 | 0.00 | 0 | |
| | very low | 0.02 | 0.04 | 0.004 | 14 |
| | | 0.04 | 0.08 | 0.008 | 95 |
| | | 0.06 | 0.12 | 0.012 | 96 |
| | | 0.08 | 0.16 | 0.016 | 97 |
| | | 0.1 | 0.20 | 0.02 | 96 |
| | | 0.12 | 0.24 | 0.024 | 96 |
| | | 0.14 | 0.28 | 0.028 | 96 |
| | | 0.2 | 0.40 | 0.04 | 97 |
| | very high | 0.3 | 0.60 | 0.06 | 97 |

FIG. 17

| No. | Dose | Final bromo (mg) per vial | Final conc (g/kg DMI) | % Bioactive /DMI | % CH4 reduction |
|---|---|---|---|---|---|
| 17-cow | | 0 | 0.00 | 0 | |
| | very low | 0.02 | 0.04 | 0.004 | -8 |
| | | 0.04 | 0.08 | 0.008 | -22 |
| | | 0.06 | 0.12 | 0.012 | 7 |
| | | 0.08 | 0.16 | 0.016 | 31 |
| | | 0.1 | 0.20 | 0.02 | 29 |
| | | 0.12 | 0.24 | 0.024 | 99 |
| | | 0.14 | 0.28 | 0.028 | 99 |
| | | 0.2 | 0.40 | 0.04 | 99 |
| | very high | 0.3 | 0.60 | 0.06 | 98 |
| 17-sheep | none | 0 | 0.00 | 0 | |
| | very low | 0.02 | 0.04 | 0.004 | 97 |
| | | 0.04 | 0.08 | 0.008 | 98 |
| | | 0.06 | 0.12 | 0.012 | 98 |
| | | 0.08 | 0.16 | 0.016 | 98 |
| | | 0.1 | 0.20 | 0.02 | 98 |
| | | 0.12 | 0.24 | 0.024 | 98 |
| | | 0.14 | 0.28 | 0.028 | 98 |
| | | 0.2 | 0.40 | 0.04 | 98 |
| | very high | 0.3 | 0.60 | 0.06 | 98 |

FIG. 18

| Treatment 1 | |
|---|---|
| Average pellets consumed per day (kg) | 15.63 |
| Concentration of treatment (ml/kg pellet) | 25 |
| Masking agent | None |
| Approximate average time taken to consume pellets | 35-60 min |
| Palatability | Medium |
| Average weight gain per animal per day (kg) | 0.76 |

Pellets given (kg) | 18 | 18 | 10 | 14 | 16 | 16 | 16 | 16 | 16 | 16 | 16
Day | 1 | 2 | 3 | 4 | 5 | 6 | 7 | 8 | 9 | 10 | 11

FIG. 19a

| Treatment 2 | |
|---|---|
| Average pellets consumed per day (kg) | 11.73 |
| Concentration of treatment (ml/kg pellet) | 25 |
| Masking agent concentration (ml/kg pellet) | 2.5 |
| Approximate average time taken to consume pellets | 30-60 min |
| Palatability | Medium |
| Average weight gain per animal per day (kg) | 1.13 |

FIG. 19b

| Treatment 3 | | |
|---|---|---|
| Average pellets consumed per day (kg) | 15.28 | |
| | Day 2-4 | Day 5-14 |
| Concentration of treatment (g/kg pellet) | 10 | 6.25 |
| Concentration of flavour enhancer (g/kg pellet) | 2.5 | 1.25 |
| Approximate average time taken to consume pellets | 20 min | |
| Palatability | High | |

FIG. 19c

| Treatment 4 | |
|---|---|
| Average pellets consumed per day (kg) | 16 |
| Treatment concentration T+ (g per kg pellet) | 5.625 |
| Treatment concentration T- (g per kg pellet) | 5.625 |
| Approximate average time taken to consume pellets | 15 min |
| Palatability | High |

FIG. 19d

| Treatment 6 | |
|---|---|
| Average pellets consumed per day | 16 kg |
| Concentration | 25 ml/kg pellet |
| Approximate average time taken to consume pellets | 15 min |
| Palatability | High |
| Average weight gain per animal per day | 0.52 kg |

| Pellets given (kg) | 16 | 16 | 16 | 16 | 16 | 16 | 16 | 16 | 16 | 16 | 16 | 16 | 16 | 16 |
|---|---|---|---|---|---|---|---|---|---|---|---|---|---|---|
| Day | 1 | 2 | 3 | 4 | 5 | 6 | 7 | 8 | 9 | 10 | 11 | 12 | 13 | 14 |

FIG. 19e

COMPOSITIONS AND METHODS FOR REDUCING GREENHOUSE GAS

CROSS REFERENCE

This application claims the benefit of U.S. Provisional Application No. 63/444,066 filed Feb. 8, 2023, which is incorporated herein by reference in its entirety.

BACKGROUND

Cattle-rearing and ruminant livestock agriculture in general produces more global warming greenhouse gases, as measured in carbon dioxide (CO2) equivalents, than transportation, according to a recent UN assessment. Ruminants produce methane (CH4) as a by-product of digestion via anaerobic microbial feed fermentation in the rumen and, to a lesser extent, the large intestine. The ruminal microbial population is made up of bacteria, protozoa, fungi, and bacteriophages, all of which work together to digest ingested organic matter and produce CO2, H2, volatile fatty acids, and formates. These end-products are used by methanogenic archaea in the rumen, which produces CH4. CH4 absorbs solar infrared radiation efficiently, and has a global warming potential 25 times that of CO2. There remains an unmet need for enteric methanogenesis mitigation techniques to reduce greenhouse emissions from ruminant livestock.

SUMMARY

In one aspect, described herein is a consumable oil-based composition for methane reduction in a ruminant, comprising (i) bromoform (ii) a plant-based oil and (iii) a medium chain triglyceride (MCT), wherein the bromoform is not derived from a biomass, wherein the concentration of the bromoform in the composition is about 0.001 wt % to about 8 wt %, wherein the concentration of MCT in the composition is about 0.01 wt % to about 33 wt %.

In some embodiments, a ratio of the bromoform to the MCT is about 1:99 to about 1:1.

In some embodiments, the ratio of the bromoform to the MCT is about 10:90 to about 30:70.

In some embodiments, a ratio of the MCT to the plant-based oil is about 1:100 to about 50:100.

In some embodiments, the ratio of the MCT to the plant-based oil is about 3:97 to about 10:90.

In some embodiments, the ratio of the MCT to the plant-based oil is about 5:95.

In some embodiments, a ratio of the bromoform to the MCT is about 1:99 to about 1:1.

In some embodiments, the plant-based oil is a vegetable oil.

In some embodiments, the vegetable oil comprises a canola oil.

In some embodiments, the composition further comprises an essential oil.

In some embodiments, the composition further comprises water.

In some embodiments, a ratio of water to the plant-based oil is about 5:95.

In some embodiments, a ratio of MCT to the plant-based oil is about 5:95.

In some embodiments, the composition is a concentrate.

In some embodiments, the concentration of bromoform is about 0.1 wt % to about 1.7 Wt %.

In some embodiments, the composition comprises a feed.

In some embodiments, the feed comprises a pellet, a bolus, a total mixed ration, a salt lick, or a mineral mix.

In some embodiments, the concentration of the bromoform is about 0.001 wt % to about 0.08 wt %.

In another aspect, described herein is a method for reducing methane expelled from a ruminant, the method comprising: (a) providing a ruminant a consumable composition of the disclosure.

In some embodiments, the method further comprises combining the consumable composition with a feed prior to providing the consumable composition to the ruminant.

In some embodiments, the feed comprises a pellet, a bolus, a total mixed ration, a salt lick, or a mineral mix.

In another aspect, described herein is a consumable composition, the composition comprising (i) a haloalkane and (ii) one or more medium chain triglyceride (MCT), the haloalkane comprising 1 to 6 carbons, the MCT comprising one or more alkyl chain, and at least one of the one or more alkyl chain comprises 6 to 12 carbon atoms.

In another aspect, described herein is a consumable solid composition, the composition comprising (i) a haloalkane (ii) a medium chain triglyceride (MCT) and (iii) a protein or a milk fat, wherein the protein is a globular protein or a milk protein.

In another aspect, described herein is a consumable semi-solid composition, the composition comprising (i) a haloalkane (ii) a setting agent, and (iii) a medium chain triglyceride (MCT).

In some embodiments, the composition further comprises a setting agent.

In some embodiments, the setting agent is a gum, agar, starch, flour or gelatin.

In some embodiments, the setting agent is a gum.

In some embodiments, the setting agent comprises gelatin.

In some embodiments, the setting agent comprises an agar.

In some embodiments, the composition comprises about 20 wt % to about 40 wt % of a total setting agent.

In some embodiments, the composition comprises about 35 wt % of the setting agent.

In some embodiments, the composition comprises about 25 wt % of the setting agent.

In some embodiments, the composition comprises about 0.001 wt % to about 0.5 wt % of the setting agent.

In some embodiments, the composition comprises about 0.05 wt % to about 0.1 wt % of the setting agent.

In some embodiments, the composition further comprises a stabilizing agent.

In some embodiments, the stabilizing agent is a globular protein, a milk protein, or a milk fat.

In some embodiments, the stabilizing agent is a globular protein or a milk protein.

In some embodiments, the milk protein is casein.

In some embodiments, the globular protein, the milk protein, and/or the milk fat is derived from a mammal.

In another aspect, described herein is a consumable water-based composition, the composition comprising (i) a haloalkane (ii) a medium chain triglyceride (MCT) and (iii) water comprising a thickening agent.

In some embodiments, the thickening agent comprises a polysaccharide.

In some embodiments, the thickening agent comprises a plant-based gum.

In some embodiments, the plant-based gum is xanthan gum.

In some embodiments, the ratio of the thickening agent and the haloalkane is about 1:10 to about 1:5.

In some embodiments, the ratio of the thickening agent and the haloalkane is about 1:8 to about 1:7.

In some embodiments, the water comprising the thickening agent has a density greater than the density of a water not comprising the thickening agent.

In some embodiments, the water comprising the thickening agent has a density of about 1.01 g/mL to about 1.06 g/mL at 20 degrees Celsius.

In some embodiments, greater amount of the haloalkane is suspended throughout the water comprising the thickening agent in comparison to a water otherwise not comprising the thickening agent.

In some embodiments, at least 90% more of the haloalkane is suspended throughout the water comprising the thickening agent in comparison to a water otherwise not comprising the thickening agent.

In some embodiments, the composition further comprises one or more emulsifiers.

In some embodiments, the composition comprises two emulsifiers.

In some embodiments, an emulsifier of the one or more emulsifiers is a polysorbate.

In some embodiments, an emulsifier of the one or more emulsifier is a plant-based lecithin (e.g., soy lecithin, or sunflower lecithin).

In some embodiments, a ratio of the emulsifier to the MCT is about 1:1 to about 1:3.

In some embodiments, a ratio of the emulsifier to the MCT is about 1:2.

In another aspect, described herein is a consumable oil-based composition, the composition comprising (i) a haloalkane (ii) a plant-based oil and (iii) a medium chain triglyceride (MCT).

In some embodiments, the plant-based oil is a vegetable oil.

In some embodiments, the vegetable oil comprises a canola oil.

In some embodiments, a ratio of the MCT to the plant-based oil is about 1:100 to about 50:100.

In some embodiments, the ratio of the MCT to the plant-based oil is about 3:97 to about 10:90.

In some embodiments, the ratio of the MCT to the plant-based oil is about 5:95.

In some embodiments, the composition further comprises one or more short chain oil.

In some embodiments, the one or more short chain oil is an essential oil.

In some embodiments, the short chain oil comprises a citrus oil or a mandarin oil.

In some embodiments, the composition further comprises a bioavailability enhancing agent.

In some embodiments, the bioavailability enhancing agent is an emulsifier and/or a stabilizer.

In some embodiments, the bioavailability enhancing agent comprises a polymer of castor oil.

In some embodiments, a ratio of the bioavailability enhancing agent and the MCT is about 1:100 to about 10:100.

In some embodiments, the MCT comprises one or more alkyl chains, and at least one of the one or more alkyl chain of the MCT comprises 6 to 12 carbon atoms (e.g., 10 carbon atoms).

In some embodiments, two or more alkyl chain of the MCT comprises 6 to 12 carbon atoms (e.g., 10 carbon atoms).

In some embodiments, each alkyl chain of the MCT comprises 6 to 12 carbon atoms (e.g., 10 carbon atoms).

In some embodiments, each alkyl chain of the MCT independently comprises 8 carbon atoms, 10 carbon atoms, or 12 carbon atoms.

In some embodiments, the MCT is a capric triglyceride.

In some embodiments, the composition is a solid composition, and the composition further comprising a stabilizing agent, the stabilizing agent being a globular protein, a milk protein, or a milk fat.

In some embodiments, the composition is a non-solid (e.g., a semi-solid or a liquid) composition.

In some embodiments, the composition is a semi-solid, and wherein the semi-solid is a gel or jelly.

In some embodiments, the ratio of the MCT to the stabilizing agent is about 1:99 to about 10:90.

In some embodiments, the ratio of the MCT to the stabilizing agent is about 5:95.

In some embodiments, the ratio of the haloalkane to the MCT is about 1:99 to about 1:1.

In some embodiments, the ratio of the haloalkane to the MCT is about 10:90 to about 30:70.

In some embodiments, the concentration of MCT in the composition is about 0.01 wt % to about 33 wt %.

In some embodiments, the concentration of MCT in the composition is about 0.03 wt % to about 7 wt %.

In some embodiments, the concentration of MCT in the composition is about 0.03 wt % to about 5 wt %.

In some embodiments, the composition has at least 20% (e.g., at least 50%, or at least 100%) improvement in chemical and/or physical stability relative to an otherwise similar composition not comprising the stabilizing agent.

In some embodiments, the composition has at least 20% (e.g., at least 50%, or at least 100%) improvement in animal consumption relative to an otherwise similar composition not comprising the stabilizing agent.

In some embodiments, the composition has at least 20% (e.g., at least 50%, or at least 100%) improvement in animal consumption relative to an otherwise similar composition not comprising the plant-based oil.

In some embodiments, the composition has at least 20% (e.g., at least 50%, or at least 100%) improvement in animal consumption relative to an otherwise similar composition comprising a greater amount of the MCT.

In some embodiments, the concentration of the haloalkane in the composition is about 0.001 wt % to about 20 wt %.

In some embodiments, the concentration of the haloalkane in the composition is about 0.001 wt % to about 0.007 wt %.

In some embodiments, the concentration of the haloalkane in the composition is about 0.001 wt % to about 8 wt %.

In some embodiments, the concentration of the haloalkane in the composition is about 0.0002 wt % to about 20 wt %.

In some embodiments, the concentration of the haloalkane in the composition is about 0.0002 wt % to about 3 wt %.

In some embodiments, the concentration of the haloalkane in the composition is about 0.1 wt % to about 20 wt %.

In some embodiments, the concentration of the haloalkane in the composition is about 0.1 wt % to about 8 wt %.

In some embodiments, the concentration of the haloalkane in the composition in the composition is about 0.10 wt % to about 0.13 wt %.

In some embodiments, the concentration of the haloalkane in the composition is about 0.25 wt % to about 0.35 wt %.

In some embodiments, the concentration of the haloalkane in the composition is about 0.36 wt % to about 0.45 wt %.

In some embodiments, the concentration of the haloalkane in the composition is about 0.5 wt % to about 0.6 wt %.

In some embodiments, the concentration of the haloalkane in the composition is about 0.75 wt % to about 0.85 wt %.

In some embodiments, the concentration of the haloalkane in the composition is about 1.3 wt % to about 1.7 wt %.

In some embodiments, the concentration of the haloalkane in the composition is about 1 wt % to about 20 wt %.

In some embodiments, the concentration of the haloalkane in the composition is about 1 wt % to about 1.5 wt %.

In some embodiments, the concentration of the haloalkane in the composition is about 2.0 wt % to about 3.2 wt %.

In some embodiments, the concentration of the haloalkane in the composition is about 4.5 wt % to about 5 wt %.

In some embodiments, the concentration of the haloalkane in the composition is about 0.08 wt % to about 3 wt %.

In some embodiments, the concentration of the haloalkane in the composition is about 0.08 wt % to about 0.15 wt %.

In some embodiments, the concentration of the haloalkane in the composition is about 0.3 wt % to about 4 wt %.

In some embodiments, the concentration of the haloalkane is about 0.7 wt % to about 1 Wt %.

In some embodiments, the concentration of the haloalkane in the composition is about 1.3 wt % to about 1.7 wt %.

In some embodiments, the concentration of the haloalkane in the composition is about 0.0002 wt % to about 0.08 wt %.

In some embodiments, the concentration of the haloalkane in the composition is about 0.001 wt % to about 0.08 wt %.

In some embodiments, the concentration of the haloalkane in the composition is about 0.001 wt % to about 0.002 wt %.

In some embodiments, the concentration of the haloalkane in the composition is about 0.003 wt % to about 0.008 wt %.

In some embodiments, the concentration of the haloalkane in the composition is about 0.009 wt % to about 0.05 wt %.

In some embodiments, the concentration of the haloalkane in the composition is about 0.0005 wt % to about 0.08 wt %.

In some embodiments, the concentration of the haloalkane in the composition is about 0.0005 wt % to about 0.0009 wt %.

In some embodiments, the concentration of the haloalkane in the composition is about 0.002 wt % to about 0.005 wt %.

In some embodiments, the concentration of the haloalkane in the composition is about 0.01 wt % to about 0.03 wt %.

In some embodiments, the concentration of the haloalkane in the composition is about 0.0001 wt % to about 0.012 wt %.

In some embodiments, the concentration of the haloalkane in the composition is about 0.0001 wt % to about 0.0005 wt %.

In some embodiments, the concentration of the haloalkane in the composition is about 0.0006 wt % to about 0.0009 wt %.

In some embodiments, the concentration of the haloalkane in the composition is about 0.001 wt % to about 0.007 wt %.

In some embodiments, the haloalkane is bromoform.

In some embodiments, the bromoform is not derived from a biomass.

In another aspect, described herein is a method for preparing a consumable oil-based composition for a ruminant, the method comprising: (a) providing a first composition comprising a haloalkane and a solvent; (b) combining at least a portion of the first composition with a MCT to produce a second composition; and (c) combining at least a portion of the second composition with a plant-based oil to produce the consumable oil-based composition.

In some embodiments, the haloalkane is at least partially soluble in the solvent.

In some embodiments, the solvent comprises ethanol.

In some embodiments, the plant-based oil comprises a canola oil.

In some embodiments, prior to (b) wherein a short chain oil is combined with the first composition.

In another aspect, described herein is a method for preparing a consumable water-based composition for a ruminant, the method comprising: (a) providing a first composition comprising a haloalkane and a medium chain triglyceride (MCT); (b) combining at least a portion of the first composition and a second composition to produce a third composition, the second composition comprising (i) water and (ii) a thickening agent, an emulsifier, or both; and (c) agitating the third composition to produce the consumable water-based composition.

In some embodiments, the second composition comprises the thickening agent and the emulsifier.

In some embodiments, the emulsifier is a polysorbate.

In some embodiments, the thickening agent comprises a plant-based gum (e.g., xanthan gum).

In some embodiments, the water has a density greater than the density of a water not comprising the thickening agent.

In some embodiments, the water has a density of about 1.01 g/mL to about 1.06 g/mL at 20 degrees Celsius.

In some embodiments, a greater amount of the haloalkane is suspended throughout the water comprising the thickening agent in comparison to a water not comprising the thickening agent.

In some embodiments, at least 90% more of the haloalkane is suspended throughout the water comprising the thickening agent in comparison to a water not comprising the thickening agent.

In some embodiments, in (c) agitating comprises mixing, sonicating, or both.

In some embodiments, in (c) agitating comprises ultrasonication.

In some embodiments, the consumable water-based composition is a high energy emulsion.

In another aspect, described herein is a method for preparing a semi-solid or solid composition for a ruminant, the method comprising: (a) providing (i) a first composition comprising a haloalkane and a medium chain triglyceride (MCT), (ii) a second composition comprising a protein or a milk fat, wherein the protein is a globular protein or a milk protein, and optionally (iii) a third composition comprising a setting agent; (b) combining at least a portion of the first composition, at least a portion of the second composition, and optionally at least a portion of the third composition to produce a fourth composition; and (c) grinding the fourth composition to produce a semi-solid or solid composition.

In some embodiments, the method further comprises prior to (a) providing a composition comprising a haloalkane and a short chain oil.

In some embodiments, at least a portion of the composition comprising the haloalkane and the short chain oil is combined with the first composition.

In some embodiments, the method further comprises prior to (c) mincing the fourth composition.

In some embodiments, the method further comprises, prior to (c) evaporating at least a portion of a liquid phase from the fourth composition.

In some embodiments, at least about 95% of the aqueous phase is evaporated.

In some embodiments, evaporating comprises heating the fourth composition at a temperature of most about 130 degrees Celsius.

In some embodiments, evaporating comprises heating the fourth composition at a temperature of about 20 degrees Celsius to about 45 degrees Celsius.

In some embodiments, evaporating comprises heating comprises spray drying.

In some embodiments, at most about 10 wt % of the haloalkane is vaporized during evaporating.

In some embodiments, at most about 5 wt % of the haloalkane is vaporized during evaporating.

In some embodiments, (a) comprises providing the third composition and (b) comprises combining the third composition.

In some embodiments, the setting agent is an agar or a gelatin.

In some embodiments, the method further comprises cooling the fourth composition.

In some embodiments, the MCT comprises one or more alkyl chain, and wherein one or more alkyl chain of the MCT comprises 6 to 12 carbon atoms (e.g., 10 carbon atoms).

In some embodiments, two or more alkyl chain of the MCT comprises 6 to 12 carbon atoms (e.g., 10 carbon atoms).

In some embodiments, each alkyl chain of the MCT comprises 6 to 12 carbon atoms (e.g., 10 carbon atoms).

In some embodiments, the MCT is a capric triglyceride.

In some embodiments, the haloalkane is bromoform.

In some embodiments, the bromoform is not derived from a biomass.

In another aspect, described herein is a method for reducing methane expelled from a ruminant, the method comprising: a. providing a consumable composition of the disclosure; b. optionally diluting the consumable composition in a feed or a water for the ruminant; and c. administering the consumable composition to the ruminant, wherein a volume of methane expelled from the ruminant is reduced by about 40% or more (e.g., about 60% or more, 75% or more, 90% or more, 95% or more, 99% or more) in comparison to the volume of methane expelled from a similarly situated ruminant not administered the consumable composition.

In another aspect, described herein is a method for reducing methane expelled from a ruminant, the method comprising: a. providing a consumable composition of the disclosure; b. diluting the consumable composition in a feed or a water for the ruminant; and c. administering the consumable composition to the ruminant, wherein a volume of methane expelled from the ruminant is reduced by about 40% or more (e.g., about 60% or more, 75% or more, 90% or more, 95% or more, 99% or more) in comparison to the volume of methane expelled from a similarly situated ruminant not administered the consumable composition.

In another aspect, described herein is a method for reducing methane expelled from a ruminant, the method comprising: a. administering a consumable composition of the disclosure to the ruminant, wherein a volume of methane expelled from the ruminant is reduced by about 40% or more (e.g., about 60% or more, 75% or more, 90% or more, 95% or more, 99% or more) in comparison to the volume of methane expelled from a similarly situated ruminant not administered the consumable composition.

In some embodiments, a volume of methane expelled from the ruminant is reduced by about 75% or more in comparison to the volume of methane expelled from a similarly situated ruminant not administered the consumable composition.

In some embodiments, a volume of methane expelled from the ruminant is reduced by about 90% or more in comparison to the volume of methane expelled from a similarly situated ruminant not administered the consumable composition.

In some embodiments, a volume of methane expelled from the ruminant is reduced by about 95% or more in comparison to the volume of methane expelled from a similarly situated ruminant not administered the consumable composition.

In some embodiments, a volume of methane expelled from the ruminant is reduced by about 99% or more in comparison to the volume of methane expelled from a similarly situated ruminant not administered the consumable composition.

In some embodiments, a volume of methane expelled from the ruminant is reduced by about 40% or more in comparison to the volume of methane expelled from a similarly situated ruminant not administered the consumable composition.

In some embodiments, a volume of methane expelled from the ruminant is reduced by about 60% or more in comparison to the volume of methane expelled from a similarly situated ruminant not administered the consumable composition.

In some embodiments, a volume of methane expelled from the ruminant is reduced by about 80% or more in comparison to the volume of methane expelled from a similarly situated ruminant not administered the consumable composition.

In some embodiments, a volume of methane expelled from the ruminant is reduced by about 90% or more in comparison to the volume of methane expelled from a similarly situated ruminant not administered the consumable composition.

In some embodiments, a volume of methane expelled from the ruminant is reduced by about 95% or more in comparison to the volume of methane expelled from a similarly situated ruminant not administered the consumable composition.

In some embodiments, a volume of methane expelled from the ruminant is reduced by about 99% or more in comparison to the volume of methane expelled from a similarly situated ruminant not administered the consumable composition.

In some embodiments, a rate of the volume of methane expelled from a ruminant per day varies at most by about 60% over a period of at least 7 days, in comparison to a similarly situated ruminant not administered the consumable composition.

In some embodiments, a rate of the volume of methane expelled from a ruminant per day varies at most by about 60% over a period of at least 14 days, in comparison to a similarly situated ruminant not administered the consumable composition.

In another aspect, described herein, is a method for using a consumable oil-based composition, the method comprising: a. providing the consumable oil-based composition of the disclosure; and
  b. diluting the consumable oil-based composition in or on a feed or a water for a ruminant.

In another aspect, described herein is a method for using a consumable water-based composition, the method comprising: a. providing the consumable water-based composition of the disclosure; and
  b. diluting the consumable water-based composition in or on a feed or a water for a ruminant.

In another aspect, described herein is a method for using a consumable semi-solid composition, the method comprising: a. providing the consumable semi-solid composition of the disclosure; and
  b. diluting the consumable semi-solid composition in or on a feed or a water for a ruminant.

In another aspect, described herein is a method for using a consumable solid composition, the method comprising: a. providing the consumable solid composition of the disclosure; and
  b. diluting the consumable solid composition in or on a feed or a water for a ruminant.

In some embodiments, the method further comprises (c) administering the feed or the water comprising the consumable composition to a ruminant.

In some embodiments, the consumable composition is diluted in the feed.

In some embodiments, diluting in the feed comprises coating the feed with the consumable composition.

In some embodiments, the consumable composition is diluted with the water.

In some embodiments, the feed is a bolus.

In some embodiments, the feed is a feed pellet.

In some embodiments, the feed is a total mixed ration.

In some embodiments, the feed is a mineral mix.

In some embodiments, the mixed ration comprises a mineral mix.

In some embodiments, the feed is a salt lick.

In some embodiments, the water is comprised in a trough.

In some embodiments, the ruminant is situated in a grazing field.

In some embodiments, the ruminant is situated in a feedlot.

In some embodiments, about 0.5 g to about 250 g of the consumable composition is diluted in about 1 kg of the feed.

In some embodiments, about 0.5 g to about 25 g of the consumable composition is diluted in about 1 kg of the feed.

In some embodiments, the consumable composition is diluted in water or a gel.

In some embodiments, the consumable composition is combined with water.

In some embodiments, the composition comprises a salt lick.

In some embodiments, the composition comprises a molasses.

In some embodiments, the composition comprises a tablet.

In some embodiments, the composition comprises a feed.

The consumable composition of any one of the preceding claims, wherein the composition comprises a pellet.

In some embodiments, the composition comprises a bolus.

In some embodiments, the composition comprises a total mixed ration.

In some embodiments, the composition comprises a mineral mix.

In one aspect, described herein is a method for reducing (a volume or a mass of) methane expelled from a ruminant by about 30% or more, the method comprising: (a) providing a first composition comprising bromoform, wherein a concentration of bromoform in the first composition is about 0.01 wt % to about 20 wt %, wherein the bromoform is not derived from a biomass; (b) providing a first ingestible product (e.g., a feed, a bolus, a salt lick, or water), the first ingestible product being suitable for ingestion by the ruminant; (c) optionally placing the first ingestible product and/or the first composition in a first vessel, wherein a volume of the vessel is at least 10 mL; (d) combining a quantity of the first composition with the first ingestible product to produce a second composition such that the first composition is coated on the first ingestible product, dispersed within the first ingestible product, or a combination thereof, wherein the concentration of bromoform in the second composition is about 0.0001 wt % to about 1 wt %; (e) optionally placing the second composition in a second vessel to hold a mass of the second composition (e.g., wherein a volume of the second vessel is sufficient for provision to the ruminant); (f) providing to the ruminant a first portion of the second composition in a manner such that all or a part of the first portion of the second composition is ingested by the ruminant; (g) providing a third composition comprising bromoform, wherein a concentration of bromoform in the third composition is about 0.01 wt % to about 20 wt %, wherein the bromoform is not derived from a biomass; (h) providing a second ingestible product (e.g., a feed, a bolus, a salt lick, or water) the second ingestible product being suitable for ingestion by the ruminant; (i) optionally placing the second ingestible product and/or the third composition in a third vessel, wherein a volume of the vessel is at least 10 mL; (j) combining a quantity of the third composition with the second ingestible product to produce a fourth composition such that the third composition is coated on the second ingestible product, dispersed within the second ingestible product, or a combination thereof, wherein the concentration of bromoform in the fourth composition is about 0.0001 wt % to about 1 wt %; (k) optionally placing the fourth composition in a second vessel to hold a mass of the second composition (e.g., wherein a volume of the fourth vessel is sufficient for provision to the ruminant); (l) providing to the ruminant a first portion of the fourth composition in a manner such that all or a part of the first portion of the fourth composition is ingested by the ruminant, wherein a period of time between (f) and (l) is about 1 day to about 1 year (e.g., about 2 days, about 1 week, about 1 month, about 6 months); and (m) optionally repeating (a)-(f) or (g)-(l) one or more times, thereby reducing methane expelled from the ruminant by at about 30% or more, over a period of time (e.g., at least 1 week, at least 1 month, at least 6 months, at least 1 year).

In some embodiments, methane expelled from a ruminant is reduced by about 30% or more in comparison to a same or similarly situated ruminant provided the same or similar ingestible product (e.g., first ingestible product or second ingestible product) in the absence of the first composition or the third composition.

In some embodiments, the first composition and the third composition are the same.

In some embodiments, the first composition and the third composition are different.

In some embodiments, the second composition and the fourth composition are the same.

In some embodiments, the second composition and the fourth composition are different.

In some embodiments, the second vessel and the fourth vessel are the same.

In some embodiments, the second vessel and the fourth vessel are different.

In some embodiments, the first vessel and the third vessel are the same.

In some embodiments, the first vessel and the third vessel are different.

In some embodiments, the method further comprises providing to the ruminant a second portion of the second composition such that the second portion of the second composition is ingested by the ruminant at a second time point after administering the first portion of the second composition (e.g., about 1 day, about 2 days, about 1 week, about 1 month, about 6 months).

In some embodiments, the method further comprises providing to the ruminant a second portion of the fourth composition such that the second portion of the fourth composition is ingested by the ruminant at a second time point after administering the first portion of the fourth composition (e.g., about 1 day, about 2 days, about 1 week, about 1 month, about 6 months).

In some embodiments, (a)-(f) is repeated one or more times, thereby reducing methane expelled from the ruminant by at about 30% or more, over a period of time (e.g., at least 1 week, at least 1 month, at least 6 months, at least 1 year).

In some embodiments, (g)-(1) is repeated one or more times, thereby reducing methane expelled from the ruminant by at about 30% or more, over a period of time (e.g., at least 1 week, at least 1 month, at least 6 months, at least 1 year).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. In particular, subject matter from PCT/AU2022/050836 is incorporated herein by reference in its entirety.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein) of which:

FIG. 6 shows an example dosage form of an oil composition when coated on top of total mixed ration, coated on top of supplement pellets, and pressed inside the supplement pellet.

FIG. 7 shows an example dosage form of a solid composition when mixed over supplement pellet, mixed in existing mineral mix, and mixed with mineral mix over a total mixed ration.

FIG. 8 shows in vitro batch fermentation assay results for solid or semi-solid compositions of the disclosure.

FIG. 9 shows in vitro batch fermentation assay results at ultra-low doses for solid or semi-solid compositions of the disclosure.

FIG. 10 shows in vitro batch fermentation assay results for oil-based compositions of the disclosure.

FIG. 11 shows in vitro batch fermentation assay results at ultra-low doses for oil-based compositions of the disclosure.

FIG. 12 shows in vitro batch fermentation assay results for water-based compositions of the disclosure.

FIG. 13 shows in vitro batch Rusitec experiment results for solid or semi-solid compositions of the disclosure.

FIG. 14 shows in vitro batch Rusitec experiment results for oil-based compositions of the disclosure.

FIG. 15 shows in vitro batch Rusitec experiment results for water-based compositions of the disclosure.

FIG. 16 show an example comparison in vitro batch fermentation assay results for solid compositions of the disclosure when conducted in cow rumen and in sheep rumen.

FIG. 17 show an example comparison in vitro batch fermentation assay results for oil-based compositions of the disclosure when conducted in cow rumen and in sheep rumen.

FIG. 18 show an example comparison in vitro batch fermentation assay results for water-based compositions of the disclosure when conducted in cow rumen and in sheep rumen.

FIG. 19a shows an example of palatability test results for a treatment comprising an oil composition with 4 g/L bromoform.

FIG. 19b shows an example of palatability test results for a treatment comprising an oil composition with 8 g/L bromoform.

FIG. 19c shows an example of palatability test results for a treatment comprising an semi-solid caseous substance in chunks, granules, and powder forms.

FIG. 19d shows an example of palatability test results for a treatment comprising a solid (powder) with and without 10% MSG.

FIG. 19e shows an example of palatability test results for a treatment comprising an oil composition with 4 g/L bromoform and canola oil.

DETAILED DESCRIPTION

Figure 1:
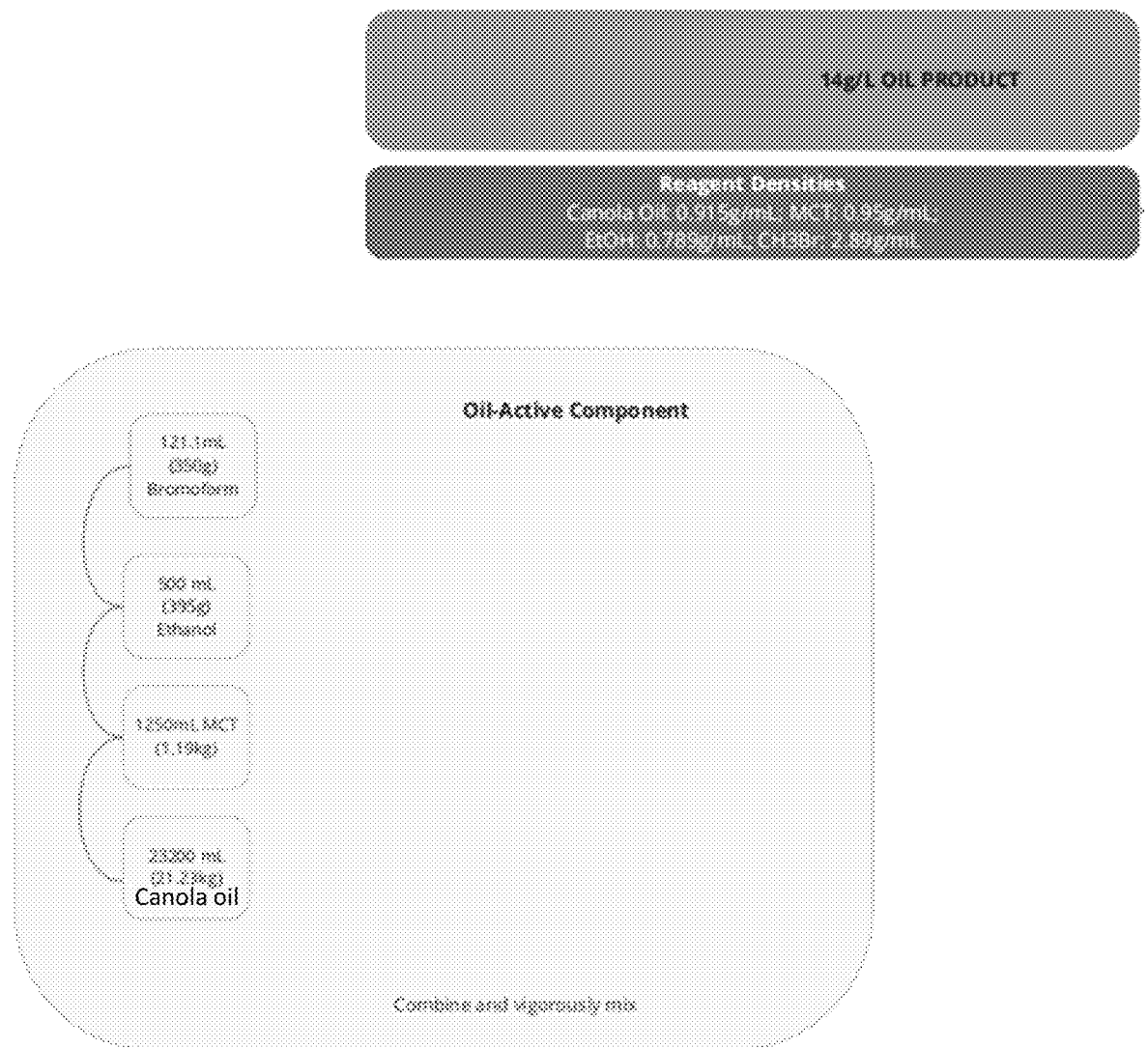
FIG. 1 illustrates an example of a schematic for the preparation of an oil-composition.

Unless defined otherwise, all technical and scientific terms used herein have the same meaning as is commonly understood by one of skill in the art to which this disclosure belongs. All patents and publications referred to herein are incorporated by reference.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "about," as used herein, means within ±10% of a value. For example, if it is stated, that "the concentration of haloalkane is about 3 wt %", it is implied that the concentration may be from 2.7 wt % to 3.3 wt %.

The term "comprise" and variations thereof, such as, "comprises" and "comprising" are to be construed in an open, inclusive sense, that is, as "including, but not limited to."

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "optional" or "optionally" denotes that a subsequently described event or circumstance can but need not occur, and that the description includes instances where the event or circumstance occurs and instances in which it does not.

The term "amount of methane" as used herein refers to "volume of methane" and/or "mass of methane."

Further, headings provided herein are for convenience only and do not interpret the scope or meaning of the claimed disclosure. The section headings used herein are for organizational purposes only and are not to be construed as limiting the subject matter described.

In some aspects, provided herein is a consumable composition comprising (i) a haloalkane and (ii) one or more medium chain triglyceride (MCT), methods of preparing, and methods of administering thereof. In some embodiments, the haloalkane comprises 1 to 6 carbons. In some embodiments, the MCT comprises one or more alkyl chain, and at least one of the one or more alkyl chain comprises 6 to 12 carbon atoms.

In some aspects, provided herein is a consumable composition comprising (i) bromoform and (ii) one or more medium chain triglyceride (MCT), at least one of one or more alkyl chain comprising 6 to 12 carbon atoms, the consumable composition comprising a solid composition, a semi-solid composition, an oil-based composition, or a water-based composition, the solid composition further comprising a protein or a milk fat, and the protein being a globular protein or a milk protein.

In some aspects, the consumable composition is a solid composition.

In some aspects, the consumable composition is a non-solid composition, e.g, a semi-solid composition, an oil-based composition, or a water-based composition. In some embodiments, the composition is a semi-solid, where the semi-solid is a gel (e.g., aqueous gel) or a jelly.

In some embodiments, the consumable composition further comprises one or more stabilizing agents, emulsifiers, setting agents, thickening agents, and/or taste enhancing agents.

In some embodiments, the consumable composition is comprises a concentrated form, such as a concentrated oil-based composition, a concentrated water based composition, or a concentrated solid or semi-solid composition (e.g., a powder).

Any composition of the disclosure may be combined or diluted with a feed for a ruminant. Any composition of the disclosure may be combined or diluted with water for a ruminant. A feed may comprise a pellet (e.g., a lucerne pellet). Any composition of the disclosure may be combined with a pellet such that the composition is inside of the pellet. Any composition of the disclosure may be combined with a pellet such that the composition is coated on the surface of a pellet.

Any composition of the disclosure may further comprise a starch (e.g., corn starch) and/or a releasing agent (e.g., calcium carbonate). The starch or the releasing agent may encourage the feed (e.g., a pellet) to break down and liberate the composition in the rumen. Once the composition at least partially liberated from the feed, the rumen may utilize the haloalkane to reduce methane expelled from the ruminant.

In some embodiments, any consumable composition of the disclosure can be diluted in a feed or water. In some embodiments, the consumable composition is comprised in a diluted form. In some embodiments, the consumable composition is diluted in or on a feed. In some embodiments, the consumable composition is diluted in (e.g., within or throughout) a feed. In some embodiments, the consumable composition is diluted on (e.g., coated) a feed. In some embodiments, the consumable composition is diluted in water. In some embodiments, water is referred to as an ingestible product herein.

In some embodiments, the consumable composition is comprised in a feed for a ruminant. In some embodiments, a feed is referred to as an ingestible product herein. In some embodiments, the feed is any one of a bolus, a feed pellet, a mixed ration, a mineral ration, a mineral mix, a mixed ration comprising a mineral mix, molasses or a salt lick. In some embodiments, the feed is a bolus. In some embodiments, the feed is a feed pellet. In some embodiments, the feed is a mixed ration. In some embodiments, the feed is a mineral ration. In some embodiments, the feed is a mineral mix. In some embodiments, the feed is a mixed ration comprising a mineral mix. In some embodiments, the feed is a salt lick. In some embodiments, the feed is molasses. In some embodiments, the feed comprises a tablet.

Haloalkanes

In some aspects, the consumable compositions provided herein comprise a haloalkane.

In some embodiments, the haloalkane comprises chlorine. In some embodiments, the haloalkane comprises iodine. In some embodiments, the haloalkane comprises 1 to 6 carbon atoms. In some embodiments, the haloalkane is bromoform (CHBr3).

Supplementing the diet of a ruminant with the red seaweed macroalgae (e.g., Asparagopsis taxiformis) has shown promise in reducing methanogenesis. Inhibition of methanogenesis in ruminants via supplementation of their feed with Asparagopsis taxiformis is largely attributed to the compound bromoform, which is present in the essential oil of the seaweed. However, the biological activity from sample to sample is inconsistent, and may further be influenced by variations in phenotype and/or chemotype from samples obtained from differing locations and environmental conditions. Such variability introduces significant uncertainties surrounding safe and effective dosage regimes in these plant-based solutions to limiting methanogenesis in ruminants. Accordingly, in some aspects, the consumable compositions described herein comprise a synthetic bromoform. In some embodiments, the consumable compositions described herein comprise bromoform not derived from a biomass.

The compositions provided herein can comprise any suitable concentration of haloalkane. In some embodiments, the concentration of the haloalkane is about 0.0002 percent weight (wt %) to about 20 wt % of the consumable composition. In some embodiments, the concentration of the haloalkane is about 0.0002 wt % to about 50 wt % of the consumable composition. In some embodiments, the concentration of the haloalkane is about 0.0002 wt % to about 0.001 wt %. In some embodiments, the concentration of the haloalkane is about 0.001 wt % to about 0.1 wt %. In some embodiments, the concentration of the haloalkane is about 0.1 wt % to about 1 wt %. In some embodiments, the concentration of the haloalkane is about 1 wt % to about 3 wt %. In some embodiments, the concentration of the haloalkane is about 3 wt % to about 5 wt %. In some embodiments, the concentration of the haloalkane is about 5 wt % to about 8 wt %. In some embodiments, the concentration of the haloalkane is about 8 wt % to about 20 wt % of the consumable composition.

In some embodiments, the concentration of the haloalkane in the composition is about 0.001 wt % to about 20 wt %. In some embodiments, the concentration of the haloalkane in the composition is about 0.001 wt % to about 0.007 wt %. In some embodiments, the concentration of the haloalkane in the composition is about 0.001 wt % to about 8 wt %. In some embodiments, the concentration of the haloalkane in the composition is about 0.0002 wt % to about 20 wt %. In some embodiments, the concentration of the haloalkane in the composition is about 0.0002 wt % to about 3 wt %. In some embodiments, the concentration of the haloalkane in the composition is about 0.1 wt % to about 20 wt %. In some embodiments, the concentration of the haloalkane in the composition is about 0.1 wt % to about 8 wt %. In some embodiments, the concentration of the haloalkane in the composition in the composition is about 0.10 wt % to about 0.13 wt %. In some embodiments, the concentration of the haloalkane in the composition is about 0.25 wt % to about 0.35 wt %. In some embodiments, the concentration of the haloalkane in the composition is about 0.36 wt % to about 0.45 wt %. In some embodiments, the concentration of the haloalkane in the composition is about 0.5 wt % to about 0.6 wt %. In some embodiments, the concentration of the haloalkane in the composition is about 0.75 wt % to about 0.85 wt %. In some embodiments, the concentration of the haloalkane in the composition is about 1.3 wt % to about 1.7 wt %. In some embodiments, the concentration of the haloalkane in the composition is about 1 wt % to about 20 wt %. In some embodiments, the concentration of the haloalkane in the composition is about 1 wt % to about 1.5 wt %. In some embodiments, the concentration of the haloalkane in the composition is about 2.0 wt % to about 3.2 wt %. In some embodiments, the concentration of the haloalkane in the composition is about 4.5 wt % to about 5 wt %. In some embodiments, the concentration of the haloalkane in the composition is about 0.08 wt % to about 3 wt %. In some embodiments, the concentration of the haloalkane in the composition is about 0.08 wt % to about 0.15 wt %. In some embodiments, the concentration of the haloalkane in the composition is about 0.3 wt % to about 4 wt %. In some embodiments, the concentration of the haloalkane is about 0.7 wt % to about 1 wt %. In some embodiments, the concentration of the haloalkane in the composition is about 1.3 wt % to about 1.7 wt %. In some embodiments, the concentration of the haloalkane in the composition is about 0.0002 wt % to about 0.08 wt %. In some embodiments, the concentration of the haloalkane in the composition is about 0.001 wt % to about 0.08 wt %. In some embodiments, the concentration of the haloalkane in the composition is about 0.001 wt % to about 0.002 wt %. In some embodiments, the concentration of the haloalkane in the composition is about 0.003 wt % to about 0.008 wt %. In some embodiments, the concentration of the haloalkane in the composition is about 0.009 wt % to about 0.05 wt %. In some embodiments, the concentration of the haloalkane in the composition is about 0.0005 wt % to about 0.08 wt %. In some embodiments, the concentration of the haloalkane in the composition is about 0.0005 wt % to about 0.0009 wt %. In some embodiments, the concentration of the haloalkane in the composition is about 0.002 wt % to about 0.005 wt %. In some embodiments, the concentration of the haloalkane in the composition is about 0.01 wt % to about 0.03 wt %. In some embodiments, the concentration of the haloalkane in the composition is about 0.0001 wt % to about 0.012 wt %. In some embodiments, the concentration of the haloalkane in the composition is about 0.0001 wt % to about 0.0005 wt %. In some embodiments, the concentration of the haloalkane in the composition is about 0.0006 wt % to about 0.0009 wt %. In some embodiments, the concentration of the haloalkane in the composition is about 0.001 wt % to about 0.007 wt %.

The compositions provided herein can comprise any suitable concentration of haloalkane prior to diluting with a feed or water. In some embodiments, the concentration of the haloalkane in a consumable composition prior to diluting with a feed or water for a ruminant is about 0.0002 wt % to about 20 wt %. In some embodiments, the concentration of the haloalkane in a consumable composition prior to diluting with a feed or water for a ruminant is about 0.05 wt % to about 8 wt %. In some embodiments, the concentration of the haloalkane in a consumable composition prior to diluting with a feed or water for a ruminant is about 0.1 wt % to about 8 wt %. In some embodiments, the concentration of the haloalkane in a consumable composition prior to diluting with a feed or water for a ruminant is about 1 wt % to about 20 wt %. In some embodiments, the concentration of the haloalkane in a consumable composition prior to diluting with a feed or water for a ruminant is about 0.08 wt % to about 3 wt %.

The compositions provided herein can comprise any suitable concentration of haloalkane after diluting with a feed or water. In some embodiments, the concentration of the haloalkane in a consumable composition after diluting with a feed or water for a ruminant is about 0.0002 wt % to about 0.1 wt %. In some embodiments, the concentration of the haloalkane in a consumable composition after diluting with a feed or water for a ruminant is about 0.0002 wt % to about 0.08 wt %. In some embodiments, the concentration of the haloalkane in a consumable composition after diluting with a feed or water for a ruminant is about 0.001 wt % to about 0.08 wt %. In some embodiments, the concentration of the haloalkane in a consumable composition after diluting with a feed or water for a ruminant is about 0.0005 wt % to about 0.08 wt %. In some embodiments, the concentration of the haloalkane in a consumable composition after diluting with a feed or water for a ruminant is about 0.0001 wt % to about 0.015 wt %.

The compositions provided herein can comprise any suitable ratio of haloalkane to medium chain triglyceride (MCT). In some embodiments, the ratio of the haloalkane to the MCT is about 1:99 to about 1:1. In some embodiments, the ratio of the haloalkane to the MCT is about 10:90 to about 20:80. In some embodiments, the ratio of the haloalkane to the MCT is about 10:90 to about 30:70.

In some embodiments, a composition comprises a varying concentration of bromoform (i.e., the same composition can comprise any suitable concentration of bromoform). In some embodiments, bromoform is carried in MCT, while the concentration of MCT in the composition remains substantially the same (e.g., changes within 1%). In some instances, a composition may comprise about 0.003 wt % to about 5 wt % MCT and a varying amounts of bromoform may be added to the MCT to yield a desired concentration of bromoform in the composition, while the concentration of the MCT in the composition remains about the same.

Medium Chain Triglyceride (MCT)

In some aspects, the consumable compositions provided herein comprise a medium chain triglyceride (MCT). In some aspects, the MCT improves the stability of the haloalkane in the consumable composition. In some aspects, the MCT improves the methane reducing properties of the consumable composition in a ruminant. For example, as shown in FIG. 12, Formulation No. 18 does not comprise MCT in comparison to Formulation No. 19, which is otherwise similar except that it comprises MCT. Formulation No. 19 consistently reduces methane production by at least 90% at a dose of bromoform of at least 0.12 g/kg Dry Matter Intake (DMI), while Formulation No. 18 only reaches about 20% methane reduction at the highest dose of 0.60 g/kg DMI.

In some embodiments, a consumable composition comprising MCT stabilizes a haloalkane in a greater quantity than a consumable composition not comprising MCT. In some embodiments, a composition comprising stabilized haloalkane reduces (an amount of) methane production by about 30% or more (e.g., 50% or more, 70% or more, 90% or more) in comparison to a composition comprising a lesser quantity of stabilized haloalkane. In some embodiments, a composition comprising stabilized haloalkane reduces (an amount of) methane production by about 50% or more in comparison to a composition comprising a lesser quantity of stabilized haloalkane. In some embodiments, a composition comprising stabilized haloalkane reduces (an amount of) methane production by about 70% or more in comparison to a composition comprising a lesser quantity of stabilized haloalkane. In some embodiments, a composition comprising stabilized haloalkane reduces (an amount of) methane production by about 90% or more in comparison to a composition comprising a lesser quantity of stabilized haloalkane. In some embodiments, a composition comprising stabilized haloalkane reduces (an amount of) methane production by about 95% or more in comparison to a composition comprising a lesser quantity of stabilized haloalkane.

In some aspects, the MCT may act as a carrier and/or stabilizing agent for the haloalkane of the consumable composition. For example, a greater quantity of bromoform is observed phase separated from a composition (e.g., at the bottom of a vessel) when the composition does not comprise MCT in comparison to a composition comprising MCT.

In some aspects, the MCT in the composition may also prevent a greater quantity of the haloalkane from vaporizing during processing (e.g., during mincing, drying, and grinding). For example, a stronger odor of bromoform was observed when processing a composition not comprising MCT in comparison to processing a composition comprising MCT.

In some aspects, the MCT may also impart a lubricating effect on the mixture during the mincing and/or grinding step to yield a more uniform solid composition.

In some instances, a lower concentration of MCT may encourage a ruminant to ingest (e.g., intake) a greater mass of feed or water (comprising a composition of the disclosure) in comparison to a (feed or water comprising an otherwise similar) composition comprising a higher concentration of MCT.

In some embodiments, the taste of the composition may be improved through reducing the concentration of MCT in the composition. In some embodiments, rate of consumption of a feed or water comprising a composition of the disclosure is a proxy for palatability of the composition. In some embodiments, rate of body weight gain of a ruminant ingesting a feed or water comprising a composition of the disclosure is a proxy for palatability of the composition.

In some embodiments, two or more alkyl chains of the MCT comprise 6 to 12 carbon atoms, e.g., 6, 7, 8, 9, 10, 11, or 12 carbon atoms.

In some embodiments, each alkyl chain of the MCT comprise 6 to 12 carbon atoms, e.g, 6, 7, 8, 9, 10, 11, or 12 carbon atoms. In some embodiments, each alkyl chain comprises 8 carbon atoms. In some embodiments, each alkyl chain comprises 10 carbon atoms. In some embodiments, each alkyl chain comprises 12 carbon atoms.

In some embodiments, the source of the MCT is coconut oil and/or palm oil. In some embodiments, the source of the MCT is a mixture of coconut oil and palm oil.

In some embodiments, the MCT comprises one or more of lauric acid, caprylic acid, and/or capric acid. In some embodiments, the MCT is a mixture of lauric acid, caprylic acid, and capric acid.

In some embodiments, the MCT is between about 50 wt % to about 80 wt % caprylic acid. In some embodiments, the MCT is between about 50 wt % and about 60 wt %. In some embodiments, the MCT is between about 60 wt % and about 70 wt %. In some embodiments, the MCT is between about 70 wt % and about 80 wt %. In some embodiments, the MCT is between about 55 wt % and about 65 wt %. In some embodiments, the MCT is between about 65 wt % and about 75 wt % caprylic acid.

In some embodiments, the MCT is between about 20 wt % and about 50 wt % capric acid. In some embodiments, the MCT is between about 20 wt % and about 30 wt %. In some embodiments, the MCT is between about 30 wt % and about 40 wt %. In some embodiments, the MCT is between about 40 wt % and about 50 wt %. In some embodiments, the MCT is between about 25 wt % and about 35 wt %. In some embodiments, the MCT is between about 35 wt % and about 45 wt % capric acid.

In some embodiments, the MCT comprises a capric triglyceride.

A composition provided herein can comprise any suitable concentration of MCT. In some embodiments, the concentration of MCT in the composition is about 0.001 wt % to about 33 wt %. In some embodiments, the concentration of MCT in the composition is about 0.01 wt % to about 0.05 wt. %. In some embodiments, the concentration of MCT in the composition is about 0.05 wt % to about 0.1 wt %. In some embodiments, the concentration of MCT in the composition is about 0.1 wt % to about 0.5 wt %. In some embodiments, the concentration of MCT in the composition is about 0.5 wt % to about 1 wt %. In some embodiments, the concentration of MCT in the composition is about 1 wt % to about 2 wt %. In some embodiments, the concentration of MCT in the composition is about 2 wt % to about 3 wt %. In some embodiments, the concentration of MCT in the composition is about 3 wt % to about 4 wt %. In some embodiments, the concentration of MCT in the composition is about 4 wt % to about 5 wt %. In some embodiments, the concentration of MCT in the composition is about 5 wt % to about 6 wt %. In some embodiments, the concentration of MCT in the composition is about 6 wt % to about 7 wt %. In some embodiments, the concentration of MCT in the composition is about 7 wt % to about 8 wt %. In some embodiments, the concentration of MCT in the composition is about 8 wt % to about 9 wt %. In some embodiments, the concentration of MCT in the composition is about 9 wt % to about 10 wt %. In some embodiments, the concentration of MCT in the composition is about 10 wt % to about 40 wt %. In some embodiments, the concentration of MCT in the composition is about 10 wt % to about 33 wt %. In some embodiments, the concentration of MCT in the composition is about 10 wt % to about 20 wt %. In some embodiments, a composition of the disclosure may comprise about 0.01 wt % to about 10 wt % MCT. In some embodiments, a composition of the disclosure may comprise about 0.01 wt % to about 5 wt % MCT. In some embodiments, the concentration of MCT in the composition is about 2 wt % to about 5 wt % of the consumable composition. In some embodiments, the concentration of MCT in a composition of the disclosure is about 2 wt % to about 5 wt % prior to combining with a feed or water. In some embodiments, the concentration of MCT in a composition of the disclosure is about 4 wt % to about 6 wt % prior to combining with a feed or water.

In some instances, a composition comprising MCT provided herein can provide improved stability (chemical or physical) of the composition (e.g., resulting in improved shelf life of the composition).

In some instances, a composition comprising MCT provided herein can provide improved palatability of the composition (e.g., resulting in improved ingestion of the composition by a ruminant).

Stabilizing Agents

In some aspects, the consumable compositions provided herein comprise one or more stabilizing agents. A composition provided herein can comprise any suitable stabilizing agent.

In some aspects, a composition of the disclosure comprises improved chemical stability (e.g., improved stability of the haloalkane) in comparison to an otherwise similar composition not comprising a stabilizing agent. In some embodiments, a stabilizing agent imparts chemical stability to a composition. In some embodiments, the stabilizing agent, imparts chemical stability of bromoform in a composition.

In some embodiments, the stabilizing agent is a globular protein and/or a milk protein. In some embodiments, the milk protein is casein.

In some embodiments, the globular protein, the milk protein, and/or the milk fat is derived from a mammal.

Milk protein or milk fat can be derived from any suitable source. In some embodiments, the milk protein and/or milk fat is derived from a milk-based material (e.g., full cream milk, fresh milk, milk powder, infant formula, whey powder). In some embodiments, the milk protein and/or milk fat is derived from full cream milk. In some embodiments, the milk protein and/or milk fat is derived from fresh pasteurized milk. In some embodiments, the milk protein and/or milk fat is derived from milk powder. In some embodiments, the milk protein and/or milk fat is derived from infant formula. In some embodiments, the milk protein and/or milk fat is derived from whey powder.

A source of a stabilizing agent can comprise any suitable concentration of the stabilizing agent. In some embodiments, the concentration of the stabilizing agent (e.g., a globular protein, a milk protein, a milk fat) in a milk-based material is about 10 wt % to about 50 wt %. In some embodiments, the concentration of the stabilizing agent in a milk-based material is about 10 wt % to about 40 wt %. In some embodiments, the concentration of the stabilizing agent in a milk-based material is about 10 wt % to about 30 wt %. In some embodiments, the concentration of the stabilizing agent in a milk-based material is about 15 wt % to about 30 wt %.

A composition provided herein can comprise any suitable concentration of a stabilizing agent. In some embodiments, the concentration of the stabilizing agent in the composition is about 5 wt % to about 45 wt %. In some embodiments, the concentration of the stabilizing in the composition is about 5 wt % to about 30 wt %. In some embodiments, the concentration of the stabilizing agent in the composition is about 10 wt % to about 40 wt %. In some embodiments, the concentration of the stabilizing agent in the composition is about 15 wt % to about 30 wt %.

A composition of the disclosure can have any suitable ratio of MCT to stabilizing agent. In some embodiments, the ratio of the MCT to the stabilizing agent is about 1:99 to about 10:90. In some embodiments, the ratio of the MCT to the stabilizing agent is about 1:99 to about 7:93. In some embodiments, the ratio of the MCT to the stabilizing agent is about 5:95.

A composition of the disclosure can have an improvement in chemical or physical stability relative to any otherwise similar composition not comprising a stabilizing agent. In some embodiments, the composition has at least a 20% (e.g., at least 50%, or at least 100%) improvement in chemical and/or physical stability relative to an otherwise similar composition not comprising the stabilizing agent. In some embodiments, the composition has at least a 30% improvement in chemical and/or physical stability relative to an otherwise similar composition not comprising the stabilizing agent. In some embodiments, the composition has at least a 40% improvement in chemical and/or physical stability relative to an otherwise similar composition not comprising the stabilizing agent. In some embodiments, the composition has at least a 50% improvement in chemical and/or physical stability relative to an otherwise similar composition not comprising the stabilizing agent. In some embodiments, the composition has at least a 60% improvement in chemical and/or physical stability relative to an otherwise similar composition not comprising the stabilizing agent. In some embodiments, the composition has at least a 70% improvement in chemical and/or physical stability relative to an otherwise similar composition not comprising the stabilizing agent. In some embodiments, the composition has at least a 80% improvement in chemical and/or physical stability relative to an otherwise similar composition not comprising the stabilizing agent. In some embodiments, the composition has at least a 90% improvement in chemical and/or physical stability relative to an otherwise similar composition not comprising the stabilizing agent. In some embodiments, the composition has at least a 100% improvement in chemical and/or physical stability relative to an otherwise similar composition not comprising the stabilizing agent.

A composition of the disclosure provided herein comprising a stabilizing agent can improve consumption by an animal (used interchangeably with "ruminant" herein) relative to an otherwise similar composition not comprising the stabilizing agent. In some embodiments, a composition comprising a stabilizing agent has at least 20% (e.g., at least 50%, or at least 100%) improvement in consumption by an animal (used interchangeably herein with "animal consumption") relative to an otherwise similar composition not comprising the stabilizing agent. In some embodiments, the composition has at least 30% improvement in consumption by an animal relative to an otherwise similar composition not comprising the stabilizing agent. In some embodiments, the composition has at least 40% improvement in consumption by an animal relative to an otherwise similar composition not comprising the stabilizing agent. In some embodiments, the composition has at least 50% improvement in consumption by an animal relative to an otherwise similar composition not comprising the stabilizing agent. In some embodiments, the composition has at least 60% improvement in consumption by an animal relative to an otherwise similar composition not comprising the stabilizing agent. In some embodiments, the composition has at least 70% improvement in consumption by an animal relative to an otherwise similar composition not comprising the stabilizing agent. In some embodiments, the composition has at least 80% improvement in consumption by an animal relative to an otherwise similar composition not comprising the stabilizing agent. In some embodiments, the composition has at least 90% improvement in consumption by an animal relative to an otherwise similar composition not comprising the stabilizing agent. In some embodiments, the composition has at least 100% improvement in consumption by an animal relative to an otherwise similar composition not comprising the stabilizing agent.

In some instances, a composition comprising a stabilizing agent provided herein can provide improved palatability (e.g., resulting in improved consumption of the composition by the animal).

Emulsifiers

A composition provided herein can comprise any suitable emulsifier. In some aspects, the consumable composition comprises one or more emulsifiers. A composition may comprise an emulsifier to improve bioavailability of the haloalkane in a ruminant. For example, an emulsifier may be added to a composition of the disclosure to improve bioavailability of bromoform in the rumen. For example, in an oil-based composition of the disclosure, the emulsifier may further emulsify the oil component while in the rumen and make the bromoform more available in the rumen.

In some embodiments, an emulsifier improves the stability (e.g., chemical and/or physical stability) of the consumable composition.

In some aspects, then emulsifier may be added to the mixture and the mixture may be emulsified through agitating the mixture (e.g., ultrasonication) to create a stable composition. In some embodiments, agitating the mixture comprises ultrasonication. In some embodiments, agitating the mixture comprises mixing the composition sufficiently to create an emulsion.

In some embodiments, the composition comprises two emulsifiers. In some embodiments, the one or more emulsifiers is a polysorbate. In some embodiments, at least one of the one or more emulsifiers is a plant-based-lecithin. In some embodiments, the plant-based lecithin is soy lecithin or sunflower lecithin.

In some embodiments, the emulsifier is a Tween. In some embodiments, the Tween is a Tween 20. In some embodiments, the Tween is a Tween 40. In some embodiments, the Tween is a Tween 60. In some embodiments, the Tween is a Tween 80. In some embodiments, a ratio of the emulsifier to the MCT is about 1:1 to about 1:3. In some embodiments, a ratio of the emulsifier to the MCT is about 1:2.

A composition provided herein can comprise any suitable concentration of an emulsifier. In some embodiments, the concentration of an emulsifier in a composition of the disclosure is about 0.005 wt % to about 3 wt %. In some embodiments, the concentration of an emulsifier in a composition of the disclosure is about 0.005 wt % to about 2 wt %. In some embodiments, the concentration of an emulsifier in a composition of the disclosure is about 0.005 wt % to about 1 wt %. In some embodiments, the concentration of an emulsifier in a composition of the disclosure is about 0.05 wt % to about 2 wt %. In some embodiments, the concentration of an emulsifier in a composition of the disclosure is about 0.5 wt % to about 2 wt %.

In some instances, a composition comprising an emulsifier provided herein can provide improved stability (chemical or physical) (e.g., resulting in improved shelf life of the composition).

In some instances, a composition comprising an emulsifier provided herein can provide improved bioavailability (e.g., resulting in an improved release rate of the haloalkane in the rumen of an animal). In some embodiments, release rate of the haloalkane in the rumen is a proxy for efficacy in methane abatement.

Setting Agents

A composition provided herein can comprise any suitable setting agent. In some aspects, the consumable composition comprises one or more setting agents. A setting agent may be added to the composition to impart homogenous dispersion of the haloalkane through the composition. Mixing a composition comprising the setting agent until it a higher viscosity of the liquid phase is reached (e.g., until the liquid phase is set, or just about set) may stabilize a homogenous dispersion of the haloalkane throughout the mixture prior to subsequent steps of the method. The composition comprising a setting agent may also be directly dried, optionally with the use elevated temperatures, from a liquid, or gel phase, to a dry solid. Solid compositions not comprising a setting agent (e.g., gelatin or agar) may require spray drying at elevated temperatures to evaporate the liquid (e.g., aqueous) phase and yield a dry solid composition.

In some embodiments, a setting agent improves the processability of a consumable composition.

In some embodiments, the setting agent is a gum, agar, starch, flour or gelatin. In some embodiments, the setting agent comprises gelatin. In some embodiments, the setting agent comprises an agar. In some embodiments, the setting agent comprises a gum. In some embodiments, the gum is xanthan gum. In some embodiments, the setting agent is corn starch. In some embodiments, the setting agent is corn flour. In some embodiments, the setting agent is a combination of agar and corn flour.

A composition provided herein can comprise any suitable concentration of a setting agent. In some embodiments, the composition further comprises about 20 wt % to about 40 wt % of the setting agent. In some embodiments, the composition comprises about 20 wt % to about 30 wt % of the setting agent. In some embodiments, the composition comprises about 30 wt % to about 40 wt % of the setting agent. In some embodiments, the composition comprises about 25 wt % to about 35 wt % of the setting agent. In some embodiments, the composition comprises about 35 wt % of the setting agent. In some embodiments, the composition comprises about 25 wt % of the setting agent.

In some embodiments, a setting agent can also serve as thickening agent as described elsewhere herein. In some embodiments, a setting agent and a thickening agent in a composition are different compounds. In some embodiments, a setting and a thickening agent in a composition are the same compound.

In some instances, a composition comprising a setting agent provided herein can provide improved processability of the composition (e.g., resulting in improved homogeneity of the composition).

Thickening Agents

A composition provided herein can comprise any suitable thickening agent. In some aspects, the consumable composition comprises a thickening agent. In some embodiments, the thickening agent comprises a polysaccharide. In some embodiments, the thickening agent comprises a plant-based gum. In some embodiments, the plant-based gum is guar gum. In some embodiments, the plant-based gum is xanthan gum. In some embodiments, the thickening agent comprises cornstarch or corn flour. In some embodiments, a thickening agent is a compound that imparts thickening of an aqueous phase (e.g., through increasing the viscosity). In some embodiments, a thickening agent comprises gelatin. In some embodiments, a thickening agent is a material sufficient to create a network of a long-chain compound (e.g., a polymer) in an aqueous phase. In some embodiments, a thickening agent is a setting agent.

A ratio of the thickening agent to the haloalkane can be any suitable ratio. In some embodiments, the ratio of the thickening agent to the haloalkane is about 1:10 to about 1:5. In some embodiments, the ratio of the thickening agent to the haloalkane is about 1:8 to about 1:7.

A composition of the disclosure can comprise any suitable concentration of a thickening agent. In some embodiments, the concentration of the thickening agent in the composition is about 0.01 wt % to about 5 wt %. In some embodiments, the concentration of the thickening agent in the composition is about 0.05 wt % to about 2 wt %. In some embodiments, the concentration of the thickening agent in the composition is about 0.1 wt % to about 1 wt %.

In some aspects, compositions comprising a thickening agent comprise a greater amount of the haloalkane is suspended throughout the composition, than a composition otherwise not comprising the thickening agent. For example, a water-based composition comprising a thickening agent has a greater amount of haloalkane suspended throughout the aqueous phase than a water-based composition not comprising the thickening agent. In some embodiments, at least 80 wt % or more of the haloalkane is suspended throughout the composition comprising the thickening agent, as compared to a composition otherwise not comprising the thickening agent. In some embodiments, at least 85 wt % or more of the haloalkane is suspended throughout the composition comprising the thickening agent, as compared to a composition otherwise not comprising the thickening agent. In some embodiments, at least 90 wt % or more of the haloalkane is suspended throughout the composition comprising the thickening agent, as compared to a composition otherwise not comprising the thickening agent. In some embodiments, at least 95 wt % or more of the haloalkane is suspended throughout the composition comprising the thickening agent, as compared to a composition otherwise not comprising the thickening agent. In some embodiments, at least 99 wt % or more of the haloalkane is suspended throughout the composition comprising the thickening agent, as compared to a composition otherwise not comprising the thickening agent.

In some instances, a composition comprising a thickening agent provided herein can provide improved processability (e.g., resulting in improved homogenous dispersion of the haloalkane in the composition).

Taste Enhancing Agents

A composition provided herein can comprise any suitable taste enhancing agent. In some aspects, the consumable composition comprises one or more taste enhancing agents. In some aspects, use of such agents may impart taste enhancement to the composition and contribute to increased consumption of the composition by a ruminant. In some aspects, use of such agents may mask the taste and/or odor of the bromoform by stabilizing the bromoform and may also be a contributing factor to increased consumption of the composition by a ruminant.

In some embodiments, a taste enhancing agent can also serve as a stabilizing agent as described elsewhere herein. In some embodiments, a taste enhancing agent can also serve as a setting agent as described elsewhere herein. In some embodiments, a taste enhancing agent can also serve as a thickening agent as described elsewhere herein. In some embodiments, the taste enhancing agent and the stabilizing agent are the same compound. In some embodiments, the taste enhancing agent and the setting agent the same compound. In some embodiments, the taste enhancing agent and the thickening agent are the same compound. In some embodiments, the taste enhancing agent and the stabilizing agent are different compounds. In some embodiments, the taste enhancing agent and the setting agent are different compounds. In some embodiments, the taste enhancing agent and the thickening agent are different compounds.

In some embodiments, the taste enhancing agent is a plant-based oil or a short chain oil (e.g., an essential oil). In some embodiments, the taste enhancing agent is monosodium glutamate (MSG). In some embodiments, the taste enhancing agent is a plant-based oil. In some embodiments, the taste enhancing agent is a short chain oil.

In some embodiments, the plant-based oil is a vegetable oil. In some embodiments, the plant-based oil comprises a canola oil. In some embodiments, the plant-based oil is coconut oil. In some embodiments, the plant-based oil is peanut oil.

In some instances, a composition comprising a taste enhancing agent provided herein can provide improved palability (e.g., resulting in improved consumption of the composition by an animal).

In some aspects, the use of a plant-based oil, e.g, canola oil, may enhance the taste and/or palatability of the composition, thereby increasing consumption of the composition by a ruminant.

A ratio of MCT to plant-based oil can be any suitable ratio. In some embodiments, a ratio of the MCT to the plant-based oil is about 1:100 to about 50:100. In some embodiments, the ratio of the MCT to the plant-based oil is about 3:97 to about 10:90. In some embodiments, the ratio of the MCT to the plant-based oil is about 5:95. In some embodiments, the taste enhancing agent is a short chain oil. In some embodiments, the one or more short chain oil is an essential oil. The essential oil can be any suitable oil. Illustrative essential oils include, but are not limited to, Bush balm oil, lemon myrtle oil, Mandarin oil, Nerolina, Palmarosa, Rosalina, Cedarwood, Bergamot, Clove bud, *Eucalyptus*, Cinnamon bark. In some embodiments, the short chain oil comprises a citrus oil or a mandarin oil.

In some aspects, use of an essential oil may mask the taste and/or odor of the bromoform by stabilizing the bromoform in the composition. In some aspects, use of an essential oil may increase consumption of the composition by a ruminant.

In some embodiments, the taste enhancing agent is MSG. In some embodiments, the taste enhancing agent is a plant-based oil.

Any composition provided herein comprise a taste enhancing agent can improve the consumption by an animal relative to any other similar composition not comprising the taste enhancing agent. In some aspects, the composition has an at least 20% (e.g., at least 50%, or at least 100%) improvement in consumption by an animal (used interchangeably with "animal consumption" herein), relative to an otherwise similar composition not comprising a taste enhancing agent. In some aspects, the composition has an at least 30% improvement in consumption by an animal, relative to an otherwise similar composition not comprising a taste enhancing agent. In some aspects, the composition has an at least 40% improvement in consumption by an animal, relative to an otherwise similar composition not comprising a taste enhancing agent. In some aspects, the composition has an at least 50% improvement in consumption by an animal, relative to an otherwise similar composition not comprising a taste enhancing agent. In some aspects, the composition has an at least 60% improvement in consumption by an animal, relative to an otherwise similar composition not comprising a taste enhancing agent. In some aspects, the composition has an at least 70% improvement in consumption by an animal, relative to an otherwise similar composition not comprising a taste enhancing agent. In some aspects, the composition has an at least 80% improvement in consumption by an animal, relative to an otherwise similar composition not comprising a taste enhancing agent. In some aspects, the composition has an at least 90% improvement in consumption by an animal, relative to an otherwise similar composition not comprising a taste enhancing agent. In some aspects, the composition has an at least 100% improvement in consumption by an animal, relative to an otherwise similar composition not comprising a taste enhancing agent.

In some embodiments, the rate of consumption of a composition of the disclosure comprising a taste enhancing agent (by a ruminant) is about 100% improved or more (e.g., 200% or more, 300% or more, 400% or more) in comparison to an otherwise similar composition not comprising the taste enhancing agent. In some embodiments, the rate of consumption of a composition of the disclosure comprising a taste enhancing agent (by a ruminant) is about 200% improved or more in comparison to an otherwise similar composition not comprising the taste enhancing agent. In some embodiments, the rate of consumption of a composition of the disclosure comprising a taste enhancing agent (by a ruminant) is about 300% improved or more in comparison to an otherwise similar composition not comprising the taste enhancing agent. In some embodiments, the rate of consumption of a composition of the disclosure comprising a taste enhancing agent (by a ruminant) is about doubled in comparison to an otherwise similar composition not comprising the taste enhancing agent. In some embodiments, the rate of consumption of a composition of the disclosure comprising a taste enhancing agent (by a ruminant) is about tripled in comparison to an otherwise similar composition not comprising the taste enhancing agent. In some instances, the rate of consumption of a composition of the disclosure comprising a taste enhancing agent (by a ruminant) is about the same in comparison to an otherwise similar composition not comprising the taste enhancing agent.

In some embodiments, the form of a composition may improve the rate of consumption of feed comprising the composition. In some embodiments, a feed or water comprising a powder form of a solid composition is consumed (by a ruminant) at a rate about 3 times faster than a feed comprising granules or chunks of an otherwise similar solid composition. In some embodiments, a feed comprising a composition of the disclosure comprising a plant-based oil is consumed by ruminant at a rate about 3 times faster than a feed comprising a composition not comprising a plant-based oil. For example, a feed comprising a composition of the disclosure comprising a plant-based oil is consumed by ruminants in about 15 minutes, whereas a feed comprising a composition not comprising a plant-based oil is consumed by ruminants in about 35-60 minutes.

In some embodiments, a composition comprising a taste enhancing agent is more palatable to a ruminant. In some embodiments, a composition comprising a lower concentration of MCT is more palatable to a ruminat. In some embodiments, a composition comprising a a smaller ratio of MCT to a taste enhancing agent is more palatable than a composition comprising a higher ratio of MCT to a taste enhancing agent. For example, a blend comprising MCT and a plant-based oil with 5% MCT is more palatable than a blend comprising 50% MCT.

Solid Compositions

In some aspects, the consumable composition is a solid composition.

In some embodiments, the consumable composition is a solid composition comprising (i) a haloalkane (ii) a medium chain triglyceride (MCT) and (iii) a stabilizing agent.

In some embodiments, the consumable composition is a solid composition comprising (i) a haloalkane (ii) a medium chain triglyceride (MCT) and (iii) a protein or a milk fat. In some embodiments, the protein is a globular protein or a milk protein.

In some embodiments, the consumable composition further comprises a setting agent. In some embodiments, the setting agent is a gum, agar, starch, flour or gelatin. In some embodiments, the setting agent comprises gelatin. In some embodiments, the setting agent comprises an agar. In some embodiments, the setting agent comprises a gum. In some embodiments, the gum is xanthan gum. In some embodiments, the gum is guar gum. In some embodiments, the solid composition comprise gelatin. In some embodiments, the solid composition comprises agar.

In some embodiments, the solid composition further comprises about 20 wt % to about 40 wt % of the setting agent. In some embodiments, the solid composition comprises about 20 wt % to about 30 wt % of the setting agent. In some embodiments, the solid composition comprises about 30 wt % to about 40 wt % of the setting agent. In some embodiments, the solid composition comprises about 25 wt % to about 35 wt % of the setting agent. In some embodiments, the composition comprises about 35 wt % of the setting agent. In some embodiments, the composition comprises about 25 wt % of the setting agent.

In some embodiments, the solid composition comprises a stabilizing agent. In some embodiments, the stabilizing agent is a globular protein, a milk protein, or a milk fat. In some embodiments, the stabilizing agent is a globular protein and/or a milk protein. In some embodiments, the milk protein is casein.

In some embodiments, the globular protein, the milk protein, and/or the milk fat is derived from a mammal.

In some embodiments, the solid composition further comprises one or more emulsifiers. In some embodiments, the composition comprises two emulsifiers. In some embodiments, the one or more emulsifiers is a polysorbate. In some embodiments, the one or more emulsifiers is a Tween. In some embodiments, at least one of the one or more emulsifiers is a plant-based-lecithin. In some embodiments, the plant-based lecithin is soy lecithin or sunflower lecithin.

In some embodiments, a ratio of the emulsifier to the MCT is about 1:1 to about 1:3. In some embodiments, a ratio of the emulsifier to the MCT is about 1:2.

In some embodiments, the haloalkane is bromoform. In some embodiments, the concentration of the bromoform is about 0.0002 wt % to about 20 wt % of the solid composition. In some embodiments, the concentration of the bromoform is about 0.0003 wt % to about 0.0005 wt %. In some embodiments, the concentration of the bromoform is about 0.0005 wt % to about 0.001 wt %. In some embodiments, the concentration of the bromoform is about 0.001 wt % to about 0.005 wt %. In some embodiments, the concentration of the bromoform is about 0.005 wt % to about 0.01 wt %. In some embodiments, the concentration of the bromoform is about 0.01 wt % to about 0.05 wt %. In some embodiments, the concentration of the bromoform is about 0.05 wt % to about 0.1 wt %. In some embodiments, the concentration of the bromoform is about 0.1 wt % to about 0.5 wt %. In some embodiments, the concentration of the bromoform is about 0.5 wt % to about 1 wt %. In some embodiments, the concentration of the bromoform is about 1 wt % to about 2 wt %. In some embodiments, the concentration of the bromoform is about 2 wt % to about 3 wt %. In some embodiments, the concentration of the bromoform is about 3 wt % to about 4 wt %. In some embodiments, the concentration of the bromoform is about 4 wt % to about 5 wt %. In some embodiments, the concentration of the bromoform is about 5 wt % to about 6 wt %. In some embodiments, the concentration of the bromoform is about 6 wt % to about 7 wt %. In some embodiments, the concentration of the bromoform is about 7 wt % to about 8 wt %. In some embodiments, the concentration of the bromoform is about 8 wt % to about 9 wt %. In some embodiments, the concentration of the bromoform is about 9 wt % to about 10 wt %. In some embodiments, the concentration of the bromoform is about 10 wt % to about 12 wt %. In some embodiments, the concentration of the bromoform is about 12 wt % to about 14 wt %. In some embodiments, the concentration of the bromoform is about 14 wt % to about 16 wt %. In some embodiments, the concentration of the bromoform is about 16 wt % to about 18 wt %. In some embodiments, the concentration of the bromoform is about 18 wt % to about 20 wt % of the solid composition. In some embodiments, the concentration of the bromoform is about 20 wt % to about 50 wt % of the solid composition.

In some embodiment, the concentration of the bromoform is about 0.0005 wt % to about 0.0015 wt %. In some embodiments, the concentration of the bromoform is about 0.0015 wt % to about 0.0025 wt %. In some embodiments, the concentration of the bromoform is about 0.0025 wt % to about 0.004 wt %. In some embodiments, the concentration of the bromoform is about 0.004 wt % to about 0.005 wt %. In some embodiments, the concentration of the bromoform is about 0.005 wt % to about 0.015 wt %. In some embodiments, the concentration of the bromoform is about 0.015 wt % to about 0.025 wt %. In some embodiments, the concentration of the bromoform is about 0.025 wt % to about 1 wt %. In some embodiments, the concentration of the bromoform is about 1 wt % to about 2.5 wt %. In some embodiments, the concentration of the bromoform is about 2.5 wt % to about 5 wt %.

In some embodiments, the consumable composition is a solid composition comprising (i) a haloalkane (ii) a medium chain triglyceride (MCT) and (iii) a protein or a milk fat. In some embodiments, the protein is a globular protein or a milk protein. In some embodiments, the globular protein or the milk protein is derived from fresh milk. In some embodiments, the haloalkane is bromoform and the concentration of the bromoform is about 0.0002 wt % to about 50 wt % (e.g., about 0.0005 wt % to about 20 wt %, about 0.0005 wt % to about 8 wt %) of the solid composition.

In some embodiments, the consumable composition is a solid composition comprising (i) a haloalkane (ii) a medium chain triglyceride (MCT) and (iii) a protein or a milk fat. In some embodiments, the protein is a globular protein or a milk protein. In some embodiments, the globular protein or the milk protein is derived from milk powder. In other specific embodiments, the haloalkane is bromoform and the concentration of the bromoform is about 0.0002 wt % to about 50 wt % (e.g., about 0.0005 wt % to about 20 wt %, about 0.0005 wt % to about 8 wt %) of the solid composition.

In some embodiments, the consumable composition is a solid composition comprising (i) a haloalkane (ii) a medium chain triglyceride (MCT) and (iii) a protein or a milk fat. In some embodiments, the protein is a globular protein or a milk protein. In some embodiments, the globular protein or the milk protein is derived from infant formula. In some embodiments, the haloalkane is bromoform and the concentration of the bromoform is about 0.0002 wt % to about 50 wt % (e.g., about 0.0005 wt % to about 20 wt %, about 0.0005 wt % to about 8 wt %) of the solid composition.

In some embodiments, the consumable composition is a solid composition comprising (i) a haloalkane (ii) a medium chain triglyceride (MCT) and (iii) a protein or a milk fat. In some embodiments, the protein is a globular protein or a milk protein. In some embodiments, the haloalkane is bromoform and the concentration of the bromoform is about 0.0002 wt % to about 50 wt % (e.g., about 0.0005 wt % to about 20 wt %, about 0.0005 wt % to about 8 wt %) of the solid composition. In some embodiments, the composition further comprises MSG.

In some embodiments, the consumable composition is a solid composition comprising (i) a haloalkane (ii) a medium chain triglyceride (MCT) and (iii) a protein or a milk fat. In some embodiments, the protein is a globular protein or a milk protein. In some embodiments, the haloalkane is bromoform and the concentration of the bromoform is about 0.0002 wt % to about 50 wt % (e.g., about 0.0005 wt % to about 20 wt %, about 0.0005 wt % to about 8 wt %) of the solid composition. In some embodiments, the composition further comprises lecithin.

In some embodiments, the consumable composition is a solid composition comprising (i) a haloalkane (ii) a medium chain triglyceride (MCT) and (iii) a protein or a milk fat. In some embodiments, the protein is a globular protein or a milk protein. In some embodiments, the milk protein is casein. In some embodiments, the haloalkane is bromoform and the concentration of the bromoform is about 0.0002 wt % to about 50 wt % (e.g., about 0.0005 wt % to about 20 wt %, about 0.0005 wt % to about 8 wt %) of the solid composition. In some embodiments, the composition further comprises lecithin.

In some embodiments, the consumable composition is a solid composition. In some embodiments a solid composition is diluted (e.g., combined with a feed, water, or and ingestible product for a ruminant). In some embodiments, a solid composition comprises about 0.05 wt % to about 2.5 wt % MCT prior to dilution with a feed for a ruminant. In some embodiments, a solid composition comprises about 0.05 wt % to about 0.25 wt % MCT (e.g., about 0.1 wt % to about 0.2 wt % MCT) prior to dilution with a feed for a ruminant. In some embodiments, a solid composition comprises about 1.5 wt % to about 2.5 wt % MCT (about 1.8 wt % to about 2.1 wt % MCT) prior to dilution with a feed for a ruminant.

In some embodiments, the consumable composition is a solid composition. In some embodiments a solid composition is diluted (e.g., combined with a feed, water, or ingestible product for a ruminant). In some embodiments, a solid composition comprises about 10 wt % to about 50 wt % of a setting agent (e.g., gelatin or agar) prior to dilution with a feed for a ruminant. In some embodiments, a solid composition comprises about 20 wt % to about 40 wt % of a setting agent (e.g., gelatin or agar) prior to dilution with a feed for a ruminant. In some embodiments, a solid composition comprises about 25 wt % to about 35 wt % of a setting agent (e.g., gelatin or agar) prior to dilution with a feed for a ruminant.

Water-Based Compositions

In some aspects, the consumable composition is a water-based composition.

In some embodiments, the consumable composition is a water-based composition comprising (i) a haloalkane (ii) a medium chain triglyceride (MCT) (iii) a thickening agent and (iv) water.

In some embodiments, the consumable composition is a water-based composition comprising (i) a haloalkane (ii) a medium chain triglyceride (MCT) and (iii) water comprising a thickening agent.

In some embodiments, the water-based composition comprises a thickening agent. In some embodiments, the thickening agent comprises a polysaccharide. In some embodiments, the thickening agent comprises a plant-based gum. In some embodiments, the plant-based gum is xanthan gum.

In some embodiments, the haloalkane is bromoform. In some embodiments, the concentration of the bromoform is about 0.0002 wt % to about 3 wt % of the water-based composition. In some embodiments, the concentration of the bromoform is about 0.0002 wt % to about 0.0005 wt % of the water-based composition. In some embodiments, the concentration of the bromoform is about 0.0005 wt % to about 0.001 wt % of the water-based composition. In some embodiments, the concentration of the bromoform is about 0.001 wt % to about 0.005 wt % of the water-based composition. In some embodiments, the concentration of the bromoform is about 0.005 wt %, to about 0.01 wt % of the water-based composition. In some embodiments, the concentration of the bromoform is about 0.01 wt % to about 0.05 wt % of the water-based composition. In some embodiments, the concentration of the bromoform is about 0.05 wt % to about 0.1 wt % of the water-based composition. In some embodiments, the concentration of the bromoform is about 0.1 wt % to about 0.5 wt % of the water-based composition. In some embodiments, the concentration of the bromoform is about 0.5 wt % to about 1 wt % of the water-based composition. In some embodiments, the concentration of the bromoform is about 1 wt % to about 2 wt % of the water-based composition. In some embodiments, the concentration of the bromoform is about 2 wt % to about 3 wt % of the water-based composition. In some embodiment, the concentration of the bromoform is about 0.0002 wt % to about 0.0005 wt %. In some embodiment, the concentration of the bromoform is about 0.08 wt % to about 0.15 wt %. In some embodiments, the concentration of the bromoform is about 0.15 wt % to about 0.3 wt %. In some embodiments, the concentration of the bromoform is about 0.3 wt % to about 1 wt %. In some embodiments, the concentration of the bromoform is about 1 wt % to about 2 wt %.

In some embodiments, the ratio of the thickening agent and the haloalkane is about 1:10 to about 1:5. In some embodiments, the ratio of the thickening agent and the haloalkane is about 1:8 to about 1:7.

In some embodiments, the concentration of the thickening agent in the composition is about 0.01 wt % to about 5 wt %. In some embodiments, the concentration of the thickening agent in the composition is about 0.05 wt % to about 2 wt %. In some embodiments, the concentration of the thickening agent in the composition is about 0.1 wt % to about 1 wt %.

In some embodiments the water comprising the thickening agent has a density greater than the density of a water not comprising the thickening agent. In some embodiments, the water comprising the thickening agent has a density of about 1.01 g/mL to about 1.06 g/mL at 20 degrees Celsius.

In some embodiments, the water has a greater viscosity than the viscosity of a water not comprising the thickening agent. In some embodiments, the water comprises a gel consistency.

In some embodiments, a greater amount of the haloalkane is suspended throughout the water comprising the thickening agent in comparison to a water otherwise not comprising the thickening agent. In some embodiments, at least 90% more of the haloalkane is suspended throughout the water comprising the thickening agent in comparison to a water otherwise not comprising the thickening agent.

In some embodiments, the water-based composition further comprises one or more emulsifiers. In some embodiments, the composition comprises two emulsifiers. In some embodiments, the one or more emulsifiers is a polysorbate. In some embodiments, the one or more emulsifiers is a Tween. In some embodiments, at least one of the one or more emulsifiers is a plant-based-lecithin. In some embodiments, the plant-based lecithin is soy lecithin, or sunflower lecithin.

In some embodiments, a ratio of the emulsifier to the MCT is about 1:1 to about 1:3. In some embodiments, a ratio of the emulsifier to the MCT is about 1:2.

In some embodiments, the consumable composition is a water-based composition comprising (i) a haloalkane (ii) a medium chain triglyceride (MCT) and (iii) water comprising a thickening agent. In some embodiments, the haloalkane is bromoform, and the concentration of the bromoform is about 0.0002 wt % to about 3 wt % of the water-based composition. In some embodiments, the ratio of the thickening agent and the haloalkane is about 1:10 to about 1:5. In some embodiments, the composition further comprises lecithin. In some embodiments, the composition further comprises xanthan gum. In some embodiments, ratio of lecithin to gum is about 5:1. In some embodiments, the ratio of lecithin to gum is about 3.5:1.5.

In some embodiments, the consumable composition is a water-based composition comprising (i) a haloalkane (ii) a medium chain triglyceride (MCT) and (iii) water comprising a thickening agent. In some embodiments, the haloalkane is bromoform, and the concentration of the bromoform is about 0.0002 wt % to about 3 wt % of the water-based composition. In some embodiments, the ratio of the thickening agent and the haloalkane is about 1:10 to about 1:5. In some embodiments, the composition further comprises Tween. In some embodiments, Tween comprises about 0.5%/v of the composition.

In some embodiments, the consumable composition is a water-based composition comprising (i) a haloalkane (ii) a medium chain triglyceride (MCT) and (iii) water comprising a thickening agent. In some embodiments, the haloalkane is bromoform, and the concentration of the bromoform is about 0.0002 wt % to about 3 wt % of the water-based composition. In some embodiments, the ratio of the thickening agent and the haloalkane is about 1:10 to about 1:5. In some embodiments, the composition further comprises xantham gum. In some embodiments, xantham gum comprises about 1% to about 5% of the composition. In some embodiments, the composition further comprises Tween. In some embodiments, Tween comprises about 0.1%/v of the composition.

In some embodiments, the consumable composition is a water-based composition comprising (i) a haloalkane (ii) a medium chain triglyceride (MCT) and (iii) water comprising a thickening agent. In some embodiments, the haloalkane is bromoform, and the concentration of the bromoform is about 0.0002 wt % to about 0.005 wt % of the water-based composition. In some embodiments, the ratio of the thickening agent and the haloalkane is about 1:10 to about 1:5. In some embodiments, the composition further comprises xanthan gum. In some embodiments, xantham gum comprises about 0.1 wt % to about 3 wt % of the composition. In some embodiments, the composition further comprises Tween. In some embodiments, Tween comprises about 0.1%/v of the composition.

In some embodiments, a water-based composition is a semi-solid composition. In some embodiments, a water-based composition is a gel.

In some embodiments, a water-based composition comprises about 5 wt % to about 80 wt % water. In some embodiments, a water-based composition comprises about 20 wt % to about 80 wt % water. In some embodiments, a water-based composition comprises about 30 wt % to about 60 wt % water. In some embodiments, a water-based composition comprises about 40 wt % to about 60 wt % water. In some embodiments, a water-based composition comprises about 5 wt % to about 15 wt % water. In some embodiments, a water-based composition comprises about 5 wt % to about 30 wt % water.

In some embodiments, a water-based semi-solid comprises a thickening agent as described elsewhere herein.

In some embodiments, a water-based semi-solid comprises a setting agent as described elsewhere herein.

In some embodiments, a consumable composition is a water-based composition. In some embodiments, a water-based composition is diluted with a feed or water for a ruminant (e.g., ingestible product). In some embodiments, a composition comprises about 0.05 wt % to about 5 wt % MCT prior to dilution with a feed or water for a ruminant. In some embodiments, a composition comprises about 1 wt % to about 5 wt % MCT prior to dilution with a feed or water for a ruminant. In some embodiments, a composition comprises about 1 wt % to about 2 wt % MCT prior to dilution with a feed or water for a ruminant. In some embodiments, a water-based composition comprises about 0.5 wt % to about 3 wt % lecithin prior to dilution with a feed or water for a ruminant.. In some embodiments, a water-based composition comprises about 0.5 wt % to about 1.5 wt % lecithin (e.g., about 1 wt %) prior to dilution with a feed or water for a ruminant.

In some embodiments, a water-based composition comprises about 0.01% to about 0.5% of a plant-based gum prior to dilution with a feed or water for a ruminant. In some embodiments, a water-based composition comprises about 0.03% to about 0.2% of a plant-based gum prior to dilution with a feed or water for a ruminant.

Semi-Solid Compositions

In some aspects, the consumable composition is a semi-solid composition. In some embodiments, the consumable composition is a semi-solid composition comprising (i) a haloalkane (ii) a medium chain triglyceride (MCT).

In some embodiments, the semi-solid composition is an aqueous gel. In some embodiments, the semi-solid composition can be diluted with a feed or a water for a ruminant. In some embodiments, an aqueous gel is diluted with water.

In some instances, a semi-solid composition may reduce resources required for transporting the composition (e.g., shipping costs, fuel needs).

In some embodiments, the semi-solid composition further comprises a setting agent. In some embodiments, the setting agent is a gum, agar, starch, flour or gelatin. In some embodiments, the setting agent comprises gelatin. In some embodiments, the setting agent comprises an agar. In some embodiments, the setting agent comprises a gum. In some embodiments, the gum is xanthan gum. In some embodiments, the setting agent comprises agar and corn flour.

In some embodiments, the semi-solid composition comprises about 20 wt % to about 40 wt % of the setting agent. In some embodiments, the composition comprises about 35 wt % of the setting agent. In some embodiments, the composition comprises about 25 wt % of the setting agent.

In some embodiments, the semi-solid composition further comprises a stabilizing agent. In some embodiments, the stabilizing agent is a globular protein, a milk protein, or a milk fat. In some embodiments, the globular protein, the milk protein, and/or the milk fat is derived from a mammal. In some embodiments, the stabilizing agent is a globular protein or a milk protein. In some embodiments, the milk protein is casein.

In some embodiments, the milk protein and/or milk fat is derived from full cream milk. In some embodiments, the milk protein and/or milk fat is derived from fresh pasteurized milk. In some embodiments, the milk protein and/or milk fat is derived from milk powder. In some embodiments, the milk protein and/or milk fat is derived from infant formula.

In some embodiments, a semi-solid composition comprises about 5 wt % to about 80 wt % water. In some embodiments, a semi-solid composition comprises about 20 wt % to about 80 wt % water. In some embodiments, a semi-solid composition comprises about 30 wt % to about 60 wt % water. In some embodiments, a semi-solid composition comprises about 40 wt % to about 60 wt % water. In some embodiments, a semi-solid composition comprises about 5 wt % to about 15 wt % water.

In some embodiments, a semi-solid composition comprises about 5 wt % to about 30 wt % water. In some embodiments, the consumable composition is a semi-solid composition comprising (i) a haloalkane (ii) a medium chain triglyceride (MCT). In some embodiments, the haloalkane is bromoform and the concentration of the bromoform is about 0.0002 wt % to about 50 wt % (e.g., about 0.0005 wt % to about 20 wt %, about 0.0005 wt % to about 8 wt %) of the semi-solid composition. In some embodiments, the composition further comprises gelatin. a protein or a milk fat. In some embodiments, the protein is a globular protein or a milk protein. In some embodiments, the globular protein or the milk protein is derived from a milk powder.

In some embodiments, the consumable composition is a semi-solid composition comprising (i) a haloalkane (ii) a medium chain triglyceride and (iii) a thickening agent. In some embodiments, the semi-solid composition comprises an emulsifier (e.g., a polysorbate). In some embodiments, the semi-solid composition comprises water.

Oil-Based Compositions

In some aspects, the consumable composition is an oil-based composition. In some embodiments, the oil-based composition comprises (i) a haloalkane (ii) a plant-based oil and (iii) a medium chain triglyceride (MCT).

In some embodiments, the plant-based oil is a vegetable oil. In some embodiments, the vegetable oil comprises a canola oil.

In some instances, the use of a vegetable oil, e.g, canola oil, may enhance the taste and/or palatability of the composition, thereby increasing consumption of the composition by a ruminant.

In some embodiments, a ratio of the MCT to the plant-based oil is about 1:100 to about 50:100. In some embodiments, the ratio of the MCT to the plant-based oil is about 3:97 to about 10:90. In some embodiments, the ratio of the MCT to the plant-based oil is about 5:95.

In some embodiments, the oil-based composition further comprises one or more short chain oil. In some embodiments, the one or more short chain oil is an essential oil. Illustrative essential oils include, but are not limited to, Bush balm oil, lemon myrtle oil, Mandarin oil, Nerolina, Palmarosa, Rosalina, Cedarwood, Bergamot, Clove bud, *Eucalyptus*, Cinnamon bark. In some embodiments, the short chain oil comprises a citrus oil or a mandarin oil. In some aspects, use of an essential oil may mask the taste and/or odor of the bromoform by stabilizing the bromoform in the composition. In some aspects, use of an essential oil may increase consumption of the composition by a ruminant. In some embodiments, palatability of a composition comprising short chain oil may be assessed in an identical fashion as palatability of a composition comprising a plant-based oil.

In some embodiments, the oil-based composition further comprises a bioavailability enhancing agent. In some aspects, the bioavailability enhancing agent improve the bioavailability of the haloalkane in a ruminant. For example, in some aspects, the emulsifier may further emulsify the oil component of the oil-based composition in the rumen thereby making the bromoform more available in the rumen. In some embodiments, the bioavailability enhancing agent is an emulsifier and/or a stabilizer. In some embodiments, the bioavailability enhancing agent comprises a polymer of castor oil. In some embodiments, the bioavailability enhancing agent is Koliphor®.

In some embodiments, a ratio of the bioavailability enhancing agent and the MCT is about 1:100 to about 10:100.

In some embodiments, the concentration of the haloalkane in the oil-based composition is about 0.001 percent weight (wt %) to about 8 wt % of the oil-based composition. In some embodiments, the concentration of the bromoform is about 0.001 wt % to about 0.005 wt % of the oil-based composition. In some embodiments, the concentration of the bromoform is about 0.005 wt %, to about 0.01 wt % of the oil-based composition. In some embodiments, the concentration of the bromoform is about 0.01 wt % to about 0.05 wt % of the oil-based composition. In some embodiments, the concentration of the bromoform is about 0.05 wt % to about 0.1 wt % of the oil-based composition. In some embodiments, the concentration of the bromoform is about 0.1 wt % to about 0.5 wt % of the oil-based composition. In some embodiments, the concentration of the bromoform is about 0.5 wt % to about 1 wt % of the oil-based composition. In some embodiments, the concentration of the bromoform is about 1 wt % to about 2 wt % of the oil-based composition. In some embodiments, the concentration of the bromoform is about 2 wt % to about 3 wt % of the oil-based composition. In some embodiments, the concentration of the bromoform is about 3 wt % to about 4 wt % of the oil-based composition. In some embodiments, the concentration of the bromoform is about 4 wt % to about 5 wt % of the oil-based composition. In some embodiments, the concentration of the bromoform is about 5 wt % to about 6 wt % of the oil-based composition. In some embodiments, the concentration of the bromoform is about 6 wt % to about 7 wt % of the oil-based composition. In some embodiments, the concentration of the bromoform is about 7 wt % to about 8 wt % of the oil-based composition.

In some embodiments, the concentration of the haloalkane in the oil-based composition is about 0.10 wt % to about 0.25 wt %. In some embodiments, the concentration of the haloalkane in the oil-based composition is about 0.25 wt % to about 0.35 wt %. In some embodiments, the concentration of the haloalkane in the oil-based composition is about 0.35 wt % to about 0.45 wt %. In some embodiments, the concentration of the haloalkane in the oil-based composition is about 0.45 wt % to about 0.50 wt %. In some embodiments, the concentration of the haloalkane in the oil-based composition is about 0.50 wt % to about 0.75 wt %. In some embodiments, the concentration of the haloalkane in the oil-based composition is about 0.75 wt % to about 0.85 wt %. In some embodiments, the concentration of the haloalkane in the oil-based composition is about 0.85 wt % to about 1.3 wt %. In some embodiments, the concentration of the haloalkane in the oil-based composition is about 1.3 wt % to about 1.7 wt %.

In some embodiments, the consumable composition is an oil based composition comprising (i) a haloalkane (ii) a plant-based oil and (iii) a medium chain triglyceride (MCT). In some embodiments, the haloalkane is bromoform and the concentration of the bromoform is about 0.0002 wt % to about 8 wt % of the solid composition.

In some embodiments, the composition further comprises Kolipher. In some embodiments, the concentration of Koliphor® is about 1 wt % of the composition.

In some embodiments, the consumable composition is a oil based composition comprising (i) a haloalkane (ii) a plant-based oil and (iii) a medium chain triglyceride (MCT). In some embodiments, the haloalkane is bromoform and the concentration of the bromoform is about 0.001 percent weight (wt %) to about 8 wt % of the oil-based composition. In some embodiments, a ratio of the MCT to the plant-based oil is about 1:100 to about 50:100. In some embodiments, the composition comprises blending 5 wt % MCT in canola oil.

In some embodiments, the composition further comprises Koliphor®. In some embodiments, the concentration of Koliphor® is about 1 wt % of the composition.

In some embodiments, the consumable composition is a oil based composition comprising (i) a haloalkane (ii) a plant-based oil and (iii) a medium chain triglyceride (MCT). In some embodiments, the haloalkane is bromoform and the concentration of the bromoform is about 0.001 percent weight (wt %) to about 8 wt % of the oil-based composition. In some embodiments, a ratio of the MCT to the plant-based oil is about 1:100 to about 50:100. In some embodiments, the composition comprises blending 5 wt % MCT and 5 wt % water in canola oil.

In some embodiments, a consumable composition is a water-based composition. In some embodiments, a water-based composition is diluted with a feed or water for a ruminant (e.g., ingestible product). In some embodiments, a composition comprises about 0.03% to about 7% MCT prior to dilution with a feed or water for a ruminant. In some embodiments, a composition comprises about 0.03% to about 1% MCT prior to dilution with a feed or water for a ruminant. In some embodiments, a composition comprises about 3% to about 6% MCT (about 5% MCT) prior to dilution with a feed or water for a ruminant.

Chemical Stability

In some aspects, chemical stability comprises the stability of the haloalkane in any of the compositions of the disclosures. In some embodiments, a composition may have improved chemical stability if a smaller quantity (e.g., wt %) of the haloalkane vaporizes in comparison to an otherwise similar composition in a same period of time. In some embodiments, an otherwise similar composition is a composition that has the same components as a composition of the disclosure, but in a different ratio. In some embodiments, an otherwise similar composition is a composition that has fewer components than a composition of the disclosure. In some embodiments, an otherwise similar composition is a composition that has the same components as a composition of the disclosure, but further comprises one or more additional components.

In some embodiments, the haloalkane in a composition of the disclosure evaporates from the composition at most about 50 weight % (wt %). In some embodiments, haloalkane in a composition of the disclosure evaporates at most about 30 wt %. In some embodiments, haloalkane in a composition of the disclosure evaporates at most about 20 wt %. In some embodiments, haloalkane in a composition of the disclosure evaporates at most about 10 wt %. In some embodiments, haloalkane in a composition of the disclosure evaporates at most about 5 wt %.

In some embodiments, haloalkane in a composition of the disclosure remains stabilized for a period of time while stored in at various temperatures. In some embodiments, at most about 10 wt % of the haloalkane vaporizes when stored for a period of time of at most about 12 months (e.g., about 10 months, about 9 months, about 6 months, about 3 months, about 2 months, about 1 month, about 2 weeks, about 1 day). In some embodiments, at most about 10 wt % of the haloalkane vaporizes when stored at a temperature of about −15° C. to about 65° C. In some embodiments, at most about 20 wt % of the haloalkane vaporizes during a period of time while stored in at a temperature of about 0° C. to about 50° C. In some embodiments, a greater quantity of the haloalkane remains stabilized for a longer period of time when subjected to relatively cooler temperatures (e.g., −15° C. to about 20° C.). In some embodiments, at least 90 wt % of a haloalkane in a composition remains stabilized for a period of time of up to 3 years at a temperature of about −15° C. to about 0° C. In some embodiments, at least 90 wt % of a haloalkane in a composition remains stabilized for up to 2 years at a temperature of about 15° C. to about 10° C. In some embodiments, at least 90 wt % of a haloalkane in a composition remains stabilized for up to 1 year at a temperature of about −15° C. to about 50° C. In some embodiments, at least 90 wt % of a haloalkane in a composition remains stabilized for up to 1 year at a temperature of about −15° C. to about 30° C. In some embodiments, at least 90 wt % of a haloalkane in a composition remains stabilized for up to 1 year at a temperature of about 5° C. to about 50° C. In some embodiments, at least 90 wt % of a haloalkane in a composition remains stabilized for up to 1 year at a temperature of about 8° C. to about 50° C. In some embodiments, at least 90 wt % of a haloalkane in a composition remains stabilized for up to 6 months at a temperature of about −15° C. to about 50° C.

In some embodiments, a composition of the disclosure comprises improved chemical stability (e.g., improved stability of the haloalkane) in comparison to an otherwise similar composition not comprising a stabilizing agent, medium-chain triglyceride, or short chain oil. In some embodiments, a stabilizing agent imparts chemical stability to a composition. In some embodiments, a medium-chain triglyceride imparts chemical stability to a composition. In some embodiments, a short chain oil (e.g., an essential oil) imparts chemical stability to a composition. In some embodiments, one or more of a stabilizing agent, medium-chain triglyceride, or short chain oil impart chemical stability of bromoform in a composition.

For example, in the preparation of a solid composition, during a drying step of the preparation, about 30 wt % to about 50 wt % of the bromoform vaporizes. In another example, a solid-composition may be prepared comprising MCT; in such examples, at most about 5 wt % of the bromoform vaporizes during the drying step. In some embodiments, a solid composition comprising MCT may have about 10-fold greater stability of bromoform than an otherwise similar solid composition not comprising MCT.

In another example, a solid-composition is prepared using MCT and a short chain oil; in such examples, at most about 2 wt % of the bromoform vaporizes during the drying step. In some embodiments, a composition comprising one or both of MCT and a short chain oil imparts improved stability to the haloalkane in the composition.

Physical Stability

In some aspects, physical stability comprises the homogeneity of a composition of the disclosure over a period of time. In some embodiments, a composition comprises improved physical stability if a smaller quantity of the haloalkane phase separates from other components in the composition over a period of time in comparison to an otherwise similar composition not comprising a component that imparts physical stability. In some embodiments, a composition comprises improved physical stability if a longer period of time is required for a composition to phase separate over a period of time in comparison to an otherwise similar composition not comprising a component that imparts physical stability. In some embodiments, a composition may have improved physical stability if an aqueous and a non-aqueous phase of the composition (e.g., a water component and an oil component) require a longer period of time to phase separate in comparison to an otherwise similar composition not comprising a component that imparts physical stability.

In some embodiments, a component that imparts physical stability comprises a surfactant, an emulsifier, a stabilizing agent, a thickening agent, a gum, or a setting agent. In some embodiments, a component that imparts physical stability to a composition is an emulsifier (e.g., a polysorbate or a milk powder). In some embodiments, a component that imparts physical stability to a composition is a stabilizing agent (e.g., milk powder). In some embodiments, a component that imparts physical stability to a composition is a thickening agent (e.g., a plant-based gum). In some embodiments, a component that imparts physical stability to a composition is a setting agent (e.g., gelatin or agar).

In some embodiments, in a composition comprising a component that imparts physical stability, at most about 30 wt % of the haloalkane will phase separate from the composition (e.g., due to density differences or low solubility). In some embodiments, in a composition comprising a component that imparts physical stability, at most about 20 wt % of the haloalkane will phase separate from the composition (e.g., due to density differences or low solubility). In some embodiments, in a composition comprising a component that imparts physical stability, at most about 10 wt % of the haloalkane will phase separate from the composition (e.g., due to density differences or low solubility).

For example, a solid-composition is prepared comprising bromoform and milk powder in an aqueous phase. In such an example, bromoform phase-separates due to the high density of bromoform. In such an example, gelatin is added to the composition to reduce phase separation of the bromoform and aqueous phase. In such an example, mixing (e.g., stirring, agitating) the aqueous composition comprising bromoform, milk powder, and gelatin until the composition is almost set (i.e., the gelatin forms a gel-like structure, like a network), creates a homogenized composition where at least 30% less bromoform phase separates from the composition in comparison to a similar composition not comprising gelatin. In some embodiments, the bromoform is prevented from phase separating (e.g., sinking in aqueous phase) due to dispersion throughout the gelatin network. In some instances, a stabilizing agent may reduce phase separation of the bromoform and aqueous phase. In some instances, a stabilizing agent may be used to emulsify the aqueous phase and reduce phase separation of bromoform and the aqueous phase.

For example, a water-based composition is prepared comprising bromoform and water, however, bromoform phase-separates due to the high density of bromoform and/or low solubility in water. In some embodiments, about 0.1 wt % to about 2 wt % of a plant-based gum (e.g., xanthan gum) is added to the composition to reduce phase separation of bromoform and aqueous phase. In some embodiments, the plant-based gum increases the density of the water through thickening the water composition (e.g., increasing the viscosity of the water composition). In such a composition comprising the plant-based gum, at least 30% less bromoform may phase separate from the composition in comparison to a similar composition not comprising the plant-based gum.

In some embodiments, shelf-life of a composition of the disclosure is the length of time the composition remains efficacious for reducing methane expelled from a ruminant. For example, a composition has a shelf-life of as long (e.g., length of time) as the concentration of bromoform in the composition is sufficient to reduce the volume of methane expelled from a ruminant by at least 30% (e.g., at least 40%, at least 50%, at least 60%). In some embodiments, shelf-life of a composition of the disclosure is determined as a factor of physical and/or chemical stability. In some embodiments, shelf-life of a composition is determined as a factor of the amount (e.g., wt %) of bromoform vaporized over a set period of time. In some embodiments, shelf-life of a composition if determined as a factor of the longevity of the homogeneity of a composition. In some embodiments, a composition of the disclosure comprises a shelf-life of a period of time as specified under a combination of one or more storage conditions (e.g., temperature, packaging material). For example, a composition of the disclosure comprises a shelf-life of at least 6 months when stored at a temperature of about 0° C. to about 50° C. For example, a composition of the disclosure comprises a shelf-life of at least 1 year when stored at a temperature of about 0° C. to about 50° C. For example, a composition of the disclosure comprises a shelf-life of at least 6 months when stored at a temperature of about 15° C. to about 25° C. For example, a composition of the disclosure comprises a shelf-life of at least 1 year when stored at a temperature of about 15° C. to about 25° C.

Methods of Preparing Oil-Based Compositions

In some aspects, described herein is a method for preparing a consumable oil-based composition for a ruminant. In some embodiments, the method comprises: a. providing a first composition comprising a haloalkane and a solvent; b. combining at least a portion of the first composition with a MCT to produce a second composition; c. combining at least a portion of the second composition with a plant-based oil to produce the consumable oil-based composition.

In some embodiments, the haloalkane is at least partially soluble in the solvent. In some embodiments, the haloalkane is miscible with the solvent. In some embodiments, the solvent comprises an alcohol (e.g., ethanol). In some embodiments, the solvent comprises an oil in which the haloalkane in miscible with.

In some embodiments, prior to (b) a short chain oil is combined with the first composition. In some embodiments, the short chain oil is described elsewhere herein. In some embodiments, the short chain oil is an essential oil. In some embodiments, the composition comprises about 0.01 wt % to about 5 wt % of the short chain oil. In some embodiments, the composition comprises about 0.01 wt % to about 3 wt % of the short chain oil. In some embodiments, the composition comprises about 0.01 wt % to about 2 wt % of the short chain oil. In some embodiments, the composition comprises about 1 wt % to about 2 wt % of the short chain oil.

In some embodiments, subsequent to (b) the short chain oil is combined with the second composition. In some embodiments, the short chain oil is described elsewhere herein. In some embodiments, the short chain oil is an essential oil. In some embodiments, the composition comprises about 0.01 wt % to about 5 wt % of the short chain oil. In some embodiments, the composition comprises about 0.01 wt % to about 3 wt % of the short chain oil. In some embodiments, the composition comprises about 0.01 wt % to about 2 wt % of the short chain oil. In some embodiments, the composition comprises about 1 wt % to about 2 wt % of the short chain oil.

In some embodiments, the plant-based oil is a plant-based oil as described elsewhere herein. In some embodiments, the plant-based oil is an edible oil. In some embodiments, the plant-based oil is an edible oil selected to enhance the palatability (e.g., uptake) of the composition to a ruminant. In some embodiments, the plant-based oil is a mixture of two or more plant-based oil. In some embodiments, the plant-based oil comprises canola oil. In some embodiments, the plant based oil comprises vegetable oil.

In some embodiments, the method is carried out at room temperature. In some embodiments, the method requires subjecting the first composition to an elevated temperature (e.g., a temperature greater than 30° C.). In some embodiments, the method requires subjecting the second composition to an elevated temperature (e.g., a temperature greater than 30° C.). In some embodiments, the method requires subjecting the oil-based composition to an elevated temperature (e.g., a temperature greater than 30° C.).

In some embodiments, combining comprises adding two or more components together. In some embodiments, combining comprises mixing. In some embodiments, combining comprises mixing until each of the added components are dispersed. In some embodiments, combining comprises mixing until each of the added components are homogenously dispersed.

As shown in FIG. 1, an exemplary oil-based composition of the disclosure is prepared by dissolving bromoform in ethanol, followed by combining with MCT. In some embodiments, the bromoform carried in MCT is diluted to a volume using canola oil.

Methods of Preparing Water-Based Compositions

In some aspects, some aspects, described herein is a method for preparing a consumable water-based composition for a ruminant. In some embodiments, the method comprises: (a) providing a first composition comprising a haloalkane and a medium chain triglyceride (MCT); (b) combining at least a portion of the first composition and a second composition to produce a third composition, the second composition comprising (i) water and (ii) a thickening agent, an emulsifier, or both; and (c) agitating the third composition to produce the consumable water-based composition.

In some embodiments, the second composition comprises the thickening agent and the emulsifier. In some embodiments, the emulsifier is a polysorbate. In some embodiments, the thickening agent comprises a plant-based gum (e.g., xanthan gum). In some embodiments, the thickening agent comprises xanthan gum. In some embodiments, the thickening agent comprises a compound that increases the density of the aqueous phase.

In some embodiments, the water has a density greater than the density of a water not comprising the thickening agent. In some embodiments, the water has a density of about 1.01 g/mL to about 1.06 g/mL at 20 degrees Celsius. In some embodiments, the water has a density of about 1.01 g/mL to about 1.05 g/mL at 20 degrees Celsius.

In some embodiments, the water has a greater viscosity than the viscosity of a water not comprising the thickening agent. In some embodiments, the water comprises a gel-like consistency.

In some embodiments, the water comprises a polymer network. In some embodiments, the water comprises a polymer network as a result of combining with a thickening agent.

In some embodiments, a greater amount of the haloalkane is suspended throughout the water comprising the thickening agent in comparison to a water not comprising the thickening agent. In some embodiments, at least about 90% more of the haloalkane is suspended throughout the water comprising the thickening agent in comparison to a water not comprising the thickening agent. In some embodiments, at least about 80% more of the haloalkane is suspended throughout the water comprising the thickening agent in comparison to a water not comprising the thickening agent. In some embodiments, at least about 90% more of the haloalkane is suspended throughout the water comprising the thickening agent in comparison to a water not comprising the thickening agent. In some embodiments, at least about 95% more of the haloalkane is suspended throughout the water comprising the thickening agent in comparison to a water not comprising the thickening agent.

In some embodiments, agitating comprises mixing, sonicating, shaking, rolling, blending or a combination thereof.

In some embodiments, the sonicating comprises ultrasonication. In some embodiments, agitating comprises mixing. In some embodiments, agitating comprising shaking. In some embodiments, agitating comprises rolling. In some embodiments, agitating comprising a vortex mixer. In some embodiments, agitating comprises a blade stirrer. In some embodiments, agitating comprises subjecting the composition to ultrasonic waves. In some embodiments, agitating comprises vigorous mixing. In some embodiments, vigorous mixing comprises agitating (e.g., mixing) sufficiently to form an emulsion. In some embodiments, vigorous mixing comprises mixing a composition at a speed of at least 60 rotations per minute (rpm). In some embodiments, vigorous mixing comprises mixing a composition at a speed of at least 500 rpm. In some embodiments, vigorous mixing comprises mixing a composition at a speed of at least 1000 rpm In some embodiments, vigorous mixing comprise the use of a vortex mixer. In some embodiments, vigorous mixing comprises mixing a composition at a speed of at least 5000 rpm. In some embodiments, vigorous mixing comprises mixing a composition at a speed of at least 10000 rpm.

In some embodiments, the consumable water-based composition is a high energy emulsion. In some embodiments, a high energy emulsion is a result of subjection a composition to ultrasonic waves.

When combining the haloalkane (e.g., bromoform) with water, the haloalkane may tend to phase separate and sink to the bottom of a vessel. The phase separation of bromoform and water may be due to the higher density of bromoform (2.89 g/cm3). The phase separation of bromoform and water may be due to the higher density of bromoform in combination with the low solubility of bromoform in water (e.g., 3.2 g/L at 30° C.). By first combining the haloalkane with a medium-chain triglyceride (MCT) prior to combining with water may improve the dispersion of the haloalkane within the MCT phase, however, the haloalkane may sink in the aqueous phase. Homogenous suspension of the haloalkane within an aqueous phase may be improved through combining a plant-based gum (e.g., xanthan gum) with water. The plant-based gum may impart thickening of the aqueous phase through reducing the viscosity of the water and creating a network within the aqueous phase. The haloalkane may have improved dispersity (e.g., less phase separation) in an aqueous phase comprising a plant-based gum.

A mixture of the haloalkane, MCT, and water comprising the thickening agent (e.g., plant based gum) may phase separate over a period of time. The phase separation may be accelerated if the mixture of the haloalkane, MCT, and water comprising the thickening agent is not agitated (e.g., stirred). An emulsifier (e.g., a polysorbate like Tween) may be added to the mixture and the mixture may be emulsified through agitating the mixture (e.g., ultrasonication) to create a stable water-based composition.

A water-composition may be prepared through combining about 5 wt % water with the MCT phase. In such embodiments, the water may be an interface to disperse the MCT phase through the aqueous phase.

Figure 2:
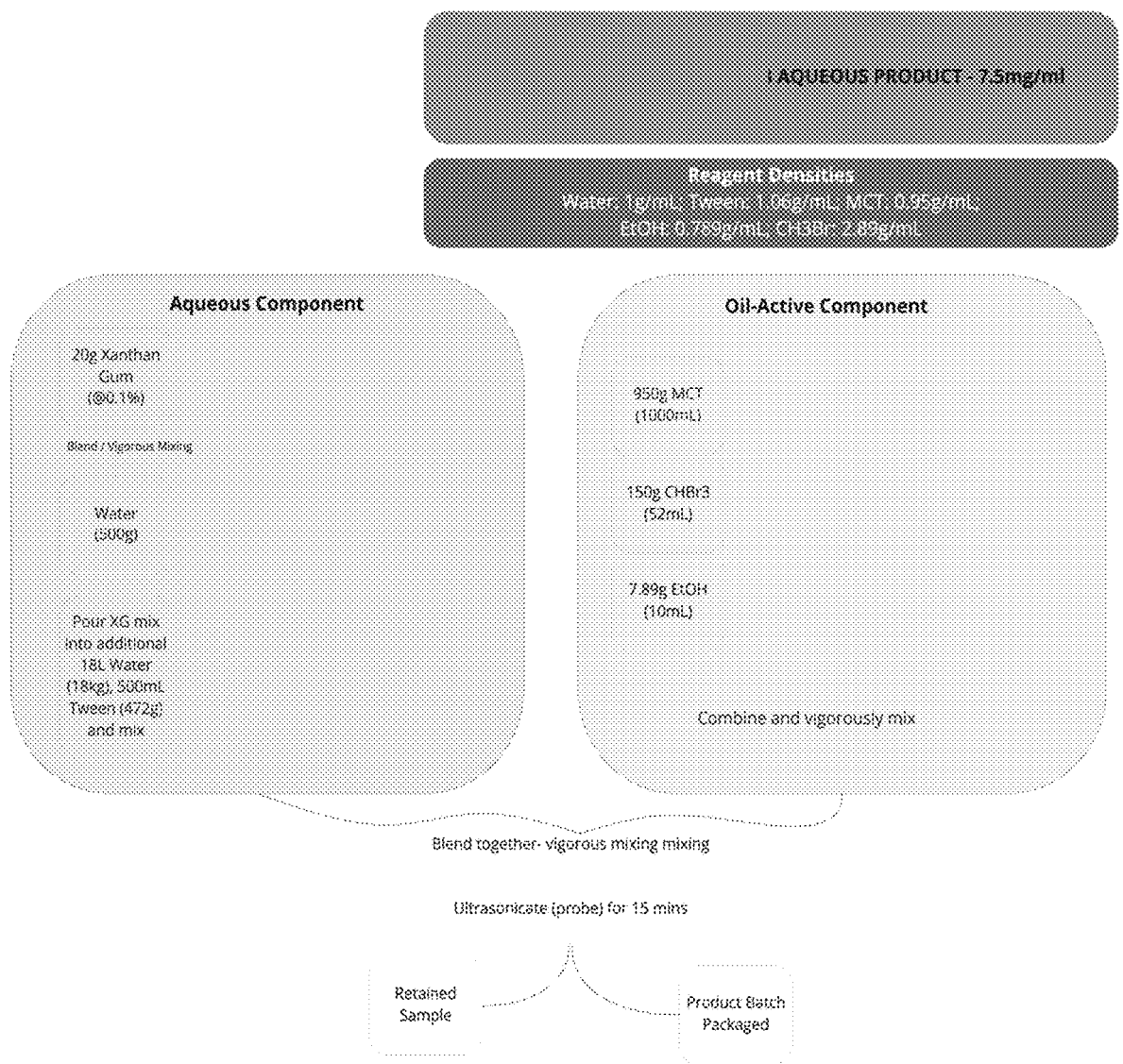
FIG. 2 illustrates an example of a schematic for the preparation of a water-based composition.

As exemplified in FIG. 2, a water-based composition is prepared by separately preparing an aqueous component comprising xanthan gum, water, and a polysorbate (e.g., Tween) and an oil-active component comprising MCT, bromoform, and ethanol. In some embodiments, the aqueous component and the oil-active components are blended and mixed together prior to subjecting the mixture to ultrasonication for a period of time.

Figure 5:
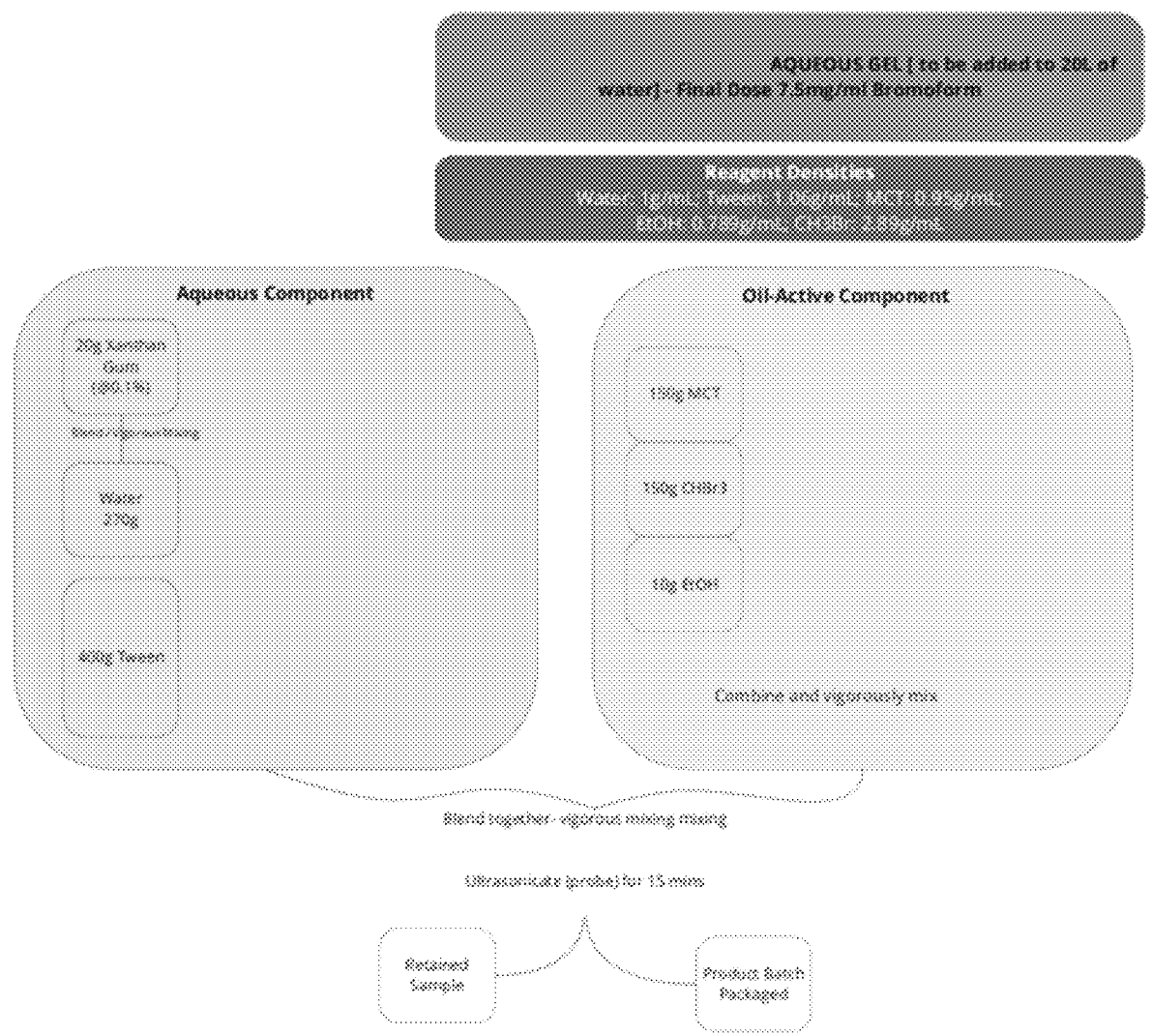
FIG. 5 illustrates an example of a schematic for the preparation of a semi-solid composition.

As exemplified in FIG. 5, a semi-solid composition is prepared as an aqueous gel through preparing an aqueous component comprising xanthan gum, water, and a polysorbate (e.g., Tween) and an oil-active component comprising MCT, bromoform, and ethanol. In some embodiments, the aqueous component and the oil-active components are blended and mixed together prior to subjecting the mixture to ultrasonication for a period of time. In some embodiments, a semi-solid composition is further diluted with water.

In some embodiments, a water-based composition is a semi-solid composition (e.g., aqueous gel). In some embodiments, a water-based semi-solid composition comprises a lower concentration of water in comparison to a water-based composition.

Methods of Preparing Solid-Based Composition

In some aspects, described herein is a method for preparing a consumable solid or semi-solid composition for a ruminant. In some embodiments, the method comprises: (a) providing a first composition comprising a haloalkane and a medium chain triglyceride (MCT), (ii) a second composition comprising a protein or a milk fat, wherein the protein is a globular protein or a milk protein, and optionally (iii) a third composition comprising a setting agent; (b) combining at least a portion of the first composition, at least a portion of the second composition, and optionally at least a portion of the third composition to produce a fourth composition; and (c) grinding the fourth composition to produce a semi-solid or solid composition.

In some embodiments, the method comprises: (a) providing a first composition comprising a haloalkane and a medium chain triglyceride (MCT), (ii) a second composition comprising a protein or a milk fat, wherein the protein is a globular protein or a milk protein, and optionally (iii) a third composition comprising a setting agent; and (b) combining at least a portion of the first composition, at least a portion of the second composition, and optionally at least a portion of the third composition to produce a fourth composition.

In some embodiments, the method comprises providing (iii) the third composition comprising a setting agent and combining at least a portion of the third composition to produce a fourth composition.

In some embodiments, the method comprises: (a) providing a first composition comprising a haloalkane and a medium chain triglyceride (MCT), (ii) a second composition comprising a protein or a milk fat, wherein the protein is a globular protein or a milk protein, and (iii) a third composition comprising a setting agent; and (b) combining at least a portion of the first composition, at least a portion of the second composition, and at least a portion of the third composition to produce a fourth composition.

In some embodiments, the method comprises: (a) providing a first composition comprising a haloalkane and a medium chain triglyceride (MCT), (ii) a second composition comprising a protein or a milk fat, wherein the protein is a globular protein or a milk protein, and (iii) a third composition comprising a setting agent; (b) combining at least a portion of the first composition, at least a portion of the second composition, and at least a portion of the third composition to produce a fourth composition; and (c) grinding the fourth composition to produce a semi-solid or solid composition.

In some embodiments, the setting agent is gelatin. In some embodiments, the setting agent is agar. In some embodiments, the setting agent comprises agar and corn flour.

In some embodiments, the method comprises: (a) providing a first composition comprising a haloalkane and a medium chain triglyceride (MCT), and (ii) a second composition comprising a protein or a milk fat, wherein the protein is a globular protein or a milk protein and (b) combining at least a portion of the first composition, at least a portion of the second composition.

In some embodiments, the method comprises: (a) providing a first composition comprising a haloalkane and a medium chain triglyceride (MCT), and (ii) a second composition comprising a protein or a milk fat, wherein the protein is a globular protein or a milk protein (b) combining at least a portion of the first composition, at least a portion of the second composition and (c) grinding the third composition to produce a semi-solid or solid composition.

In some embodiments, the method comprises, prior to (a) providing a composition comprising a haloalkane and a short chain oil. In some embodiments, the short chain oil is an essential oil. In some embodiments, at least a portion of the composition comprising the haloalkane and the short chain oil is combined with the first composition. In some embodiments, the haloalkane is combined with a short chain oil prior to being combined with MCT.

In some embodiments, the method further comprises, prior to (c) mixing the fourth composition. In some embodiments, the method further comprises mixing the fourth composition until the fourth composition is almost set. In some embodiments, the fourth compositing being almost set comprises the fourth composition having an increased viscosity.

In some embodiments, the method further comprises, prior to (c) pouring the fourth composition into a tray or mold. In some embodiments, the method further comprises, prior to (c) setting the fourth composition in a cool environment (e.g., a temperature below 15° C.). In some embodiments, the fourth composition is stored in a cool environment until the mixture has fully set.

In some embodiments, the method further comprises, prior to (c) mincing the fourth composition. In some embodiments, mincing comprises breaking a larger portion of the fourth composition to smaller portions. In some embodiments, mincing generates heat from the composition. In some embodiments, heat generated through mincing the composition is minimized through the presence of a lubricating agent. In some embodiments, a lubricating agent is MCT.

In some embodiments, the method further comprises, prior to (c) evaporating at least a portion of a liquid phase from the fourth composition. In some embodiments, evaporating at least a portion of a liquid phase from the fourth composition comprises evaporating an aqueous phase from the fourth composition. In some embodiments, about 80 wt % to about 100 wt % of the aqueous phase is evaporated from the fourth composition. In some embodiments, about 80 wt % to about 95 wt % of the aqueous phase is evaporated from the fourth composition. In some embodiments, about 90 wt % to about 100 wt % of the aqueous phase is evaporated from the fourth composition. In some embodiments, about 90 wt % to about 95 wt % of the aqueous phase is evaporated from the fourth composition. In some embodiments, evaporating comprises subjecting the fourth composition to a source of heat. In some embodiments, evaporating comprises subjecting the fourth composition to an elevated temperature. In some embodiments, an elevated temperature is about 50° C. to about 130° C. In some embodiments, an elevated temperature is about 20° C. to about 45° C. In some embodiments, an elevated temperature is at most about 130° C. In some embodiments, evaporating comprise spray drying.

In some embodiments, during an evaporating step, a minimal quantity of haloalkane may be vaporized. In some embodiments, at most about 20 wt % of the haloalkane is vaporized during evaporation. In some embodiments, about 0.1 wt % to about 15 wt % of the haloalkane is vaporized during evaporated. In some embodiments, about 0.1 wt % to about 10 wt % of the haloalkane is vaporized during evaporation. In some embodiments, about 0.1 wt % to about 5 wt % of the haloalkane is vaporized during evaporation. In some embodiments, the presence of a stabilizing agent minimizes the bromoform vaporized during evaporation. In some embodiments, the stabilizing agent is MCT.

In some embodiments, grinding comprises breaking a size of the composition to a smaller size. In some embodiments, the fourth composition can be grinded to yield a powder with an average particle size of about 0.1 micrometers to about 1000 micrometers. In some embodiments, the fourth composition can be grinded to yield a powder with an average particle size of about 0.1 micrometers to about 500 micrometers. In some embodiments, the fourth composition is grinded to yield a powder with an average particle size of about 0.1 micrometers to about 250 micrometers. For example, particles with a size greater than about 250 micrometers can be separated using a screen (e.g., mesh) and further subjected to grinding to yield a particle less than about 250 micrometers. In some embodiments, grinding generates heat from the composition. In some embodiments, heat generated through grinding the composition is minimized through the presence of a lubricating agent. In some embodiments, a lubricating agent is MCT. In some embodiments, grinding comprises subjecting the composition to a processor. In some embodiments, grinding comprises processing the composition. In some embodiments, grinding comprises blending the composition. In some embodiments, grinding comprises the use of a mortar and pestle. In some embodiments, grinding comprises the use of a ball mill, jet mill, pin mill or other mill.

In some embodiments, a semi-solid composition is prepared. In some embodiments, the method comprises evaporating a portion of the aqueous phase from the composition. In some embodiments, about 10 wt % to about 80 wt % of the aqueous phase is evaporated to yield a semi-solid composition. In some embodiments, about 10 wt % to about 60 wt % of the aqueous phase is evaporated to yield a semi-solid composition. In some embodiments, about 10 wt % to about 40 wt % of the aqueous phase is evaporated to yield a semi-solid composition. In some embodiments, none of the aqueous phase is evaporated from the composition. In some embodiments, the semi-solid composition is a gel. In some embodiments, the semi-solid composition is a jelly.

In some embodiments, a solid composition is prepared. In some embodiments, about 80 wt % to about 100 wt % of the aqueous phase is evaporated from the fourth composition. In some embodiments, about 80 wt % to about 95 wt % of the aqueous phase is evaporated from the fourth composition. In some embodiments, about 90 wt % to about 100 wt % of the aqueous phase is evaporated from the fourth composition. In some embodiments, about 90 wt % to about 95 wt % of the aqueous phase is evaporated from the fourth composition. In some embodiments, the fourth composition is subjected to grinding. In some embodiments, the method comprises grinding the composition. In some embodiments, the method comprises grinding the composition to yield a powder. In some embodiments, the fourth composition is not subjected to grinding. In some embodiments, the solid composition is a powder. In some embodiments, the composition comprises larger pieces of the solid composition (e.g., chunks, granules, pellets, chips, noodles, slabs).

When combining the haloalkane (e.g., bromoform) with a solution of milk powder (e.g., milk powder in water), phase partitioning may be observed where the haloalkane sinks to the bottom of the vessel. Phase partitioning of the bromoform and aqueous phase may occur due to the higher density of bromoform. Phase partitioning of the water and aqueous phase may occur due to the higher density of bromoform in combination with a lower solubility of the bromoform in water.

Figure 3:
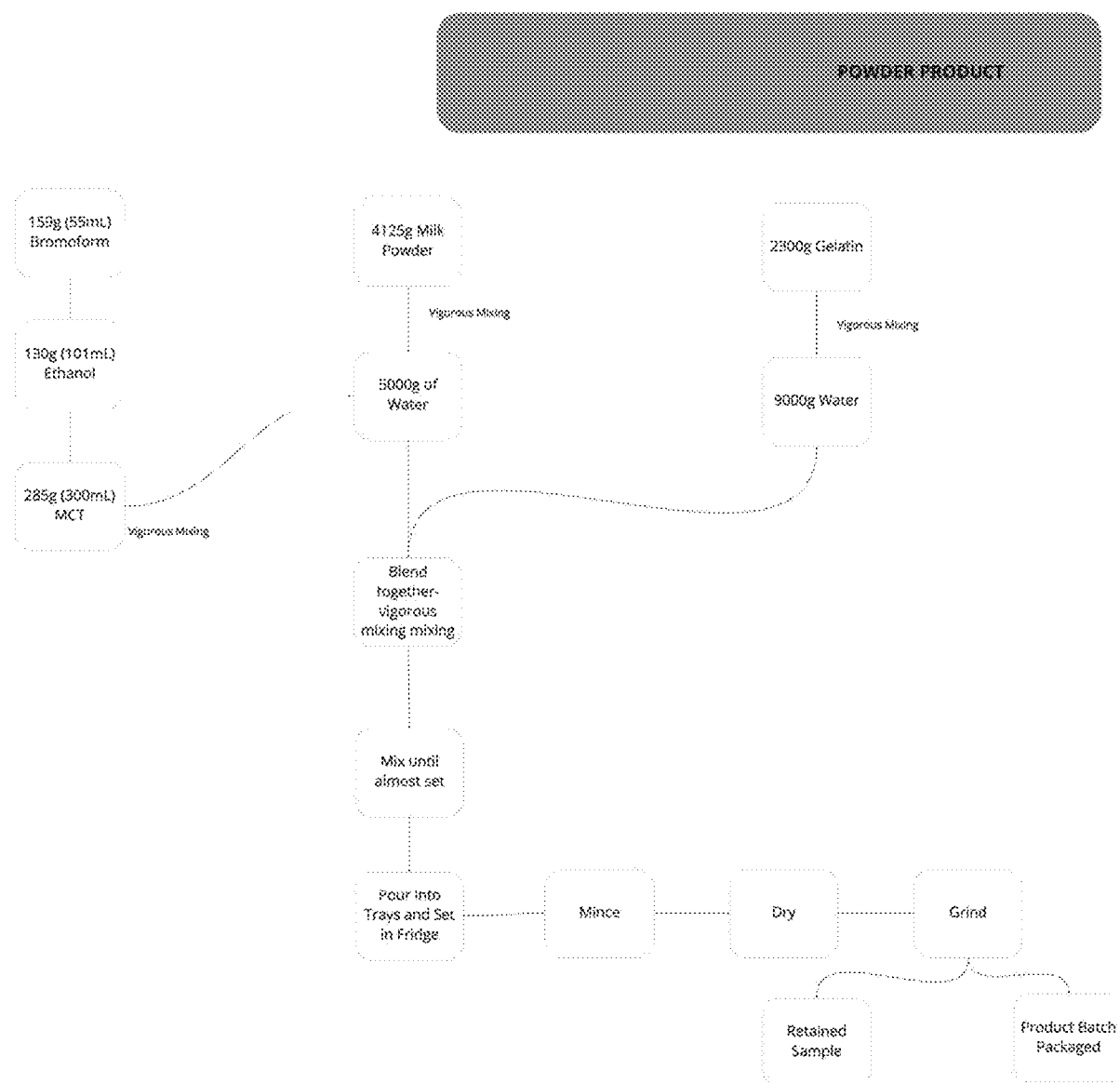
FIG. 3 illustrates an example of a schematic for the preparation of a solid composition, using gelatin.

As exemplified in FIG. 3, a solid composition can be prepared using gelatin. In some embodiments, bromoform is dissolved into ethanol and combined with MCT. In some embodiments, milk powder is mixed in with water separately, and gelatin is mixed in with water, separately. In some embodiments, the milk powder mixture and gelatin mixture are combined with the bromoform in MCT mixture. In some embodiments, the mixture is agitated (e.g., mixed) until the gelatin is almost set. In some embodiments, the mixture is poured into moulds or a tray. In some embodiments, the mixture is cooled until it is fully set. In some embodiments, the mixture is minced into smaller pieces. In some embodiments, the mixture is dried (e.g., water is evaporated). In some embodiments, the mixture is grinded to yield a powder like composition.

Figure 4:
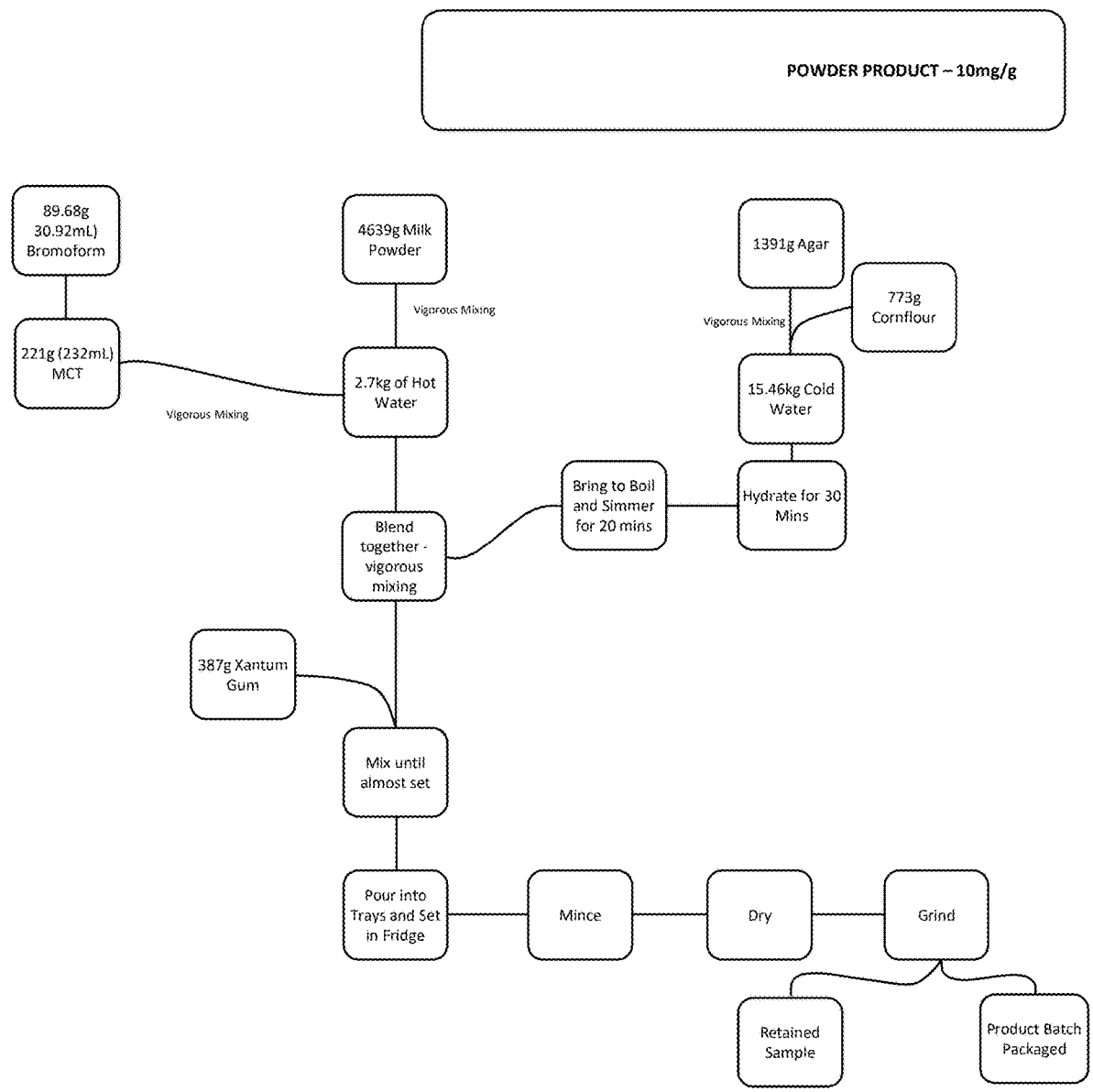
FIG. 4 illustrates an example of a schematic for the preparation of a solid composition, using agar.

As exemplified in FIG. 4, a solid composition can be prepared using agar. In some embodiments, bromoform is combined with MCT. In some embodiments, milk powder is mixed with hot water. In some embodiments, hot water is water at a temperature of about 60° C. to about 100° C. In some embodiments, hot water is water at a temperature of about 60° C. to about 80° C. In some embodiments, agar is mixed with corn flour and cold water. In some embodiments, cold water is water at a temperature of about 0° C. to about 25° C. In some embodiments, the agar mixture is hydrated for a period of time. In some embodiments, the hydrated agar mixture is brought to a boil and simmered for a period of time. In some embodiments, the bromoform mixture is combined with the milk powder mixture. In some embodiments, the bromoform mixture is combined with the agar mixture. In some embodiments, the bromoform mixture, the milk powder mixture, and the agar mixture are combined. In some embodiments, a plant-based gum (e.g., xanthan gum) is added to the mixture comprising bromoform, MCT, milk powder, and agar. In some embodiments, the mixture is agitated (e.g., mixed) until the agar is almost set. In some embodiments, the mixture is poured into moulds or a tray. In some embodiments, the mixture is cooled until it is fully set. In some embodiments, the mixture is minced into smaller pieces. In some embodiments, the mixture is dried (e.g., water is evaporated). In some embodiments, the mixture is grinded to yield a powder like composition.

In some embodiments, a semi-solid can be prepared for use following the schematic provided in FIG. 3 or FIG. 4 by omitting, at least, a drying step. In some embodiments, a semi-solid of the composition can be prepared by not evaporating water from the composition. In some embodiments, a semi-solid of the composition can be prepared by evaporating a portion of the water from the composition. In some embodiments, a semi-solid is prepared by evaporating at most about 95 wt % of water. In some embodiments, a semi-solid is prepared by evaporating at most 80 wt % of water. In some embodiments, a semi-solid is prepared by evaporating at most 70 wt % of water. In some embodiments, a semi-solid is prepared by evaporating at most 60 wt % of water. In some embodiments, a semi-solid is prepared by evaporating at most 50 wt % of water. In some embodiments, a semi-solid is prepared by evaporating at most 40 wt % of water. In some embodiments, a semi-solid is prepared by evaporating at most 30 wt % of water. In some embodiments, a semi-solid is prepared by evaporating at most 20 wt % of water. In some embodiments, a semi-solid is prepared by evaporating at most 10 wt % of water. In some embodiments, a semi-solid is prepared by evaporating at most 5 wt % of water.

Methane Reduction

The compositions of the disclosure may be used for reducing methane expelled from a ruminant. In some embodiments, ingestion of a composition of the disclosure by a ruminant reduces methane expelled from the ruminant.

In some embodiments, the compositions of the disclosure consistently reduce an amount of methane expelled from a ruminant when ingested daily. In some embodiments, the compositions of the disclosure consistently reduce an amount of methane expelled from a ruminant when ingested every other day. In some embodiments, the compositions of the disclosure consistently reduce an amount of methane expelled from a ruminant when ingested weekly. In some embodiments, the compositions of the disclosure consistently reduce an amount of methane expelled from a ruminant when ingested biweekly. In some embodiments, the compositions of the disclosure consistently reduce an amount of methane expelled from a ruminant when ingested monthly. In some embodiments, the compositions of the disclosure consistently reduce an amount of methane expelled from a ruminant when ingested semi-annually. In some embodiments, the compositions of the disclosure consistently reduce an amount of methane expelled from a ruminant when ingested annually.

In some embodiments, the amount of methane expelled by a ruminant is consistently at a reduced amount in between administration and ingestion of the composition. For example, a ruminant ingesting a composition may have reduced methane expulsion by about 30% on the day of ingesting the composition, and the reduction of methane expulsion stays at about 30% until the next administration and ingestion of the composition by the ruminant.

In some embodiments, the amount of methane expelled by a ruminant is non-uniform in between administration and ingestion of the composition. For example, a ruminant ingesting a composition may have reduced methane expulsion by about 30% on the day of ingestion the composition, and the reduction of methane expulsion may be at 10% 7 days after the initial ingestion of the composition.

In some aspects, described herein is a method for reducing methane expelled from a ruminant comprising (a) providing a consumable composition of the disclosure; (b) optionally diluting the consumable composition in a feed or a water for the ruminant; and (c) administering the consumable composition to the ruminant, wherein an amount (e.g., volume or mass) of methane expelled from the ruminant is reduced by about 40% or more (e.g., about 60% or more, 75% or more, 90% or more, 95% or more, 99% or more) in comparison to the volume of methane expelled from a similarly situated ruminant not administered the consumable composition.

In another aspect, described herein is a method for reducing methane expelled from a ruminant comprising (a) providing a consumable composition of the disclosure; (b) diluting the consumable composition in a feed or a water for the ruminant; and (c) administering the consumable composition to the ruminant, wherein an amount (e.g., volume or mass) of methane expelled from the ruminant is reduced by about 40% or more (e.g., about 60% or more, 75% or more, 90% or more, 95% or more, 99% or more) in comparison to the volume of methane expelled from a similarly situated ruminant not administered the consumable composition.

In another aspect, described herein is a method for reducing methane expelled from a ruminant comprising (a) administering a consumable composition to the ruminant, wherein an amount (e.g., volume or mass) of methane expelled from the ruminant is reduced by about 40% or more (e.g., about 60% or more, 75% or more, 90% or more, 95% or more, 99% or more) in comparison to the amount (e.g., volume or mass) of methane expelled from a similarly situated ruminant not administered the consumable composition.

In some embodiments, an amount (e.g., volume or mass) of methane expelled is reduced over a period of time. In some embodiments, an amount of methane expelled is reduced over a period of time of at least 1 day. In some embodiments, an amount of methane expelled is reduced over a period of time of at least 1 week. In some embodiments, an amount of methane expelled is reduced over a period of time of at least 2 weeks. In some embodiments, an amount of methane expelled is reduced over a period of time of at least 1 month. In some embodiments, an amount of methane expelled is reduced over a period of time of at least 2 months. In some embodiments, an amount of methane expelled is reduced over a period of time of at least 3 months. In some embodiments, an amount of methane expelled is reduced over a period of time of at least 6 months. In some embodiments, an amount of methane expelled is reduced over a period of time of at least 1 year.

In some embodiments, the amount (e.g., volume or mass) of methane expelled from a ruminant (e.g., receiving any consumable composition provided herein) is reduced by about 60% or more in comparison to the amount of methane expelled from a similarly situated ruminant not receiving (e.g., ingesting or administered or fed) the consumable composition. In some embodiments, the amount of methane expelled from a ruminant(e.g., receiving any consumable composition provided herein) is reduced by about 75% or more in comparison to the amount of methane expelled from a similarly situated ruminant not administered the consumable composition. In some embodiments, the amount of methane expelled from a ruminant(e.g., receiving any consumable composition provided herein) is reduced by about 90% or more in comparison to the amount of methane expelled from a similarly situated ruminant not administered the consumable composition. In some embodiments, the amount of methane expelled from a ruminant(e.g., receiving any consumable composition provided herein) is reduced by about 95% or more in comparison to the amount of methane expelled from a similarly situated ruminant not administered the consumable composition. In some embodiments, the amount of methane expelled from a ruminant (e.g., receiving any consumable composition provided herein) is reduced by about 99% or more in comparison to the amount of methane expelled from a similarly situated ruminant not administered the consumable composition.

In some embodiments, a similarly situated ruminant is a ruminant that is provided the consumable composition in a same or similar setting (e.g., field or feedlot). In some embodiments, a similarly situated ruminant is a ruminant that is of the same species (e.g., cattle or sheep). In some embodiments, a similarly situated ruminant is a ruminant that is of the same or substantially similar (e.g., within 5%) body weight. In some embodiments, a similarly situated ruminant is a ruminant that is of the same or substantially similar (e.g., within 1 year) age. In some embodiments, a similarly situated ruminant is a ruminant that has a same or substantially same diet. In some embodiments, a similarly situated ruminant is a ruminant that has a same or substantially same (e.g., within 5 kg) intake of feed. In some embodiments, a similarly situated ruminant is a ruminant that has a same or substantially same (e.g., within 5 L) intake of water. In some embodiments, a similarly situated ruminant is a ruminant that has a same or substantially similar health (e.g., a disease or lack thereof).

In some embodiments, methane produced from a ruminant (e.g., in vivo measurements) is measured using techniques known in art. In some embodiments, methane produced from a ruminant is measured using a respiration chamber. In some embodiments, methane produced from a ruminant is measured using a greenfed breath analyzer station. In some embodiments, methane produced from a ruminant is measured using sulfur hexafluoride tracer techniques. In some embodiments, methane produced from a ruminant is measured using a laser. In some embodiments, methane produced from a ruminant is measured using a breath analyzer (e.g., NDIR or FTIR). In some embodiments, methane produced from a ruminant is measured using a sensor in the stomach of a ruminant. In some aspects, in vitro experiment results are a proxy for determining methane production achieved in vivo.

In one aspect, described herein is a method for reducing an amount of methane expelled from a ruminant by about 30% or more, the method comprising: (a) providing a first composition comprising bromoform, wherein a concentration of bromoform in the first composition is about 0.01 wt % to about 20 wt %, wherein the bromoform is not derived from a biomass; (b) providing a first ingestible product (e.g., a feed, a bolus, a salt lick, or water), the first ingestible product being suitable for ingestion by the ruminant; (c) optionally placing the first ingestible product and/or the first composition in a first vessel, wherein a volume of the vessel is at least 10 mL; (d) combining a quantity of the first composition with the first ingestible product to produce a second composition such that the first composition is coated on the first ingestible product, dispersed within the first ingestible product, or a combination thereof, wherein the concentration of bromoform in the second composition is about 0.0001 wt % to about 1 wt %; (e) optionally placing the second composition in a second vessel to hold a mass of the second composition (e.g., wherein a volume of the second vessel is sufficient for provision to the ruminant); (f) providing to the ruminant a first portion of the second composition in a manner such that all or a part of the first portion of the second composition is ingested by the ruminant; (g) providing a third composition comprising bromoform, wherein a concentration of bromoform in the third composition is about 0.01 wt % to about 20 wt %, wherein the bromoform is not derived from a biomass; (h) providing a second ingestible product (e.g., a feed, a bolus, a salt lick, or water) the second ingestible product being suitable for ingestion by the ruminant; (i) optionally placing the second ingestible product and/or the third composition in a third vessel, wherein a volume of the vessel is at least 10 mL; (j) combining a quantity of the third composition with the second ingestible product to produce a fourth composition such that the third composition is coated on the second ingestible product, dispersed within the second ingestible product, or a combination thereof, wherein the concentration of bromoform in the fourth composition is about 0.0001 wt % to about 1 wt %; (k) optionally placing the fourth composition in a second vessel to hold a mass of the second composition (e.g., wherein a volume of the fourth vessel is sufficient for provision to the ruminant); (l) providing to the ruminant a first portion of the fourth composition in a manner such that all or a part of the first portion of the fourth composition is ingested by the ruminant, wherein a period of time between (f) and (l) is about 1 day to about 1 year (e.g., about 2 days, about 1 week, about 1 month, about 6 months); and (m) optionally repeating (a)-(f) or (g)-(l) one or more times, thereby reducing methane expelled from the ruminant by at about 30% or more, over a period of time (e.g., at least 1 week, at least 1 month, at least 6 months, at least 1 year).

In one aspect, described herein is a method for reducing an amount of methane expelled from a ruminant by about 30% or more, the method comprising: (a) providing a first composition comprising bromoform, wherein a concentration of bromoform in the first composition is about 0.01 wt % to about 20 wt %, wherein the bromoform is not derived from a biomass; (b) providing a first ingestible product (e.g., a feed, a bolus, a salt lick, or water), the first ingestible product being suitable for ingestion by the ruminant; (c) placing the first ingestible product and/or the first composition in a first vessel, wherein a volume of the vessel is at least 10 mL; (d) combining a quantity of the first composition with the first ingestible product to produce a second composition such that the first composition is coated on the first ingestible product, dispersed within the first ingestible product, or a combination thereof, wherein the concentration of bromoform in the second composition is about 0.0001 wt % to about 1 wt %; (e) placing the second composition in a second vessel to hold a mass of the second composition (e.g., wherein a volume of the second vessel is sufficient for provision to the ruminant); (f) providing to the ruminant a first portion of the second composition in a manner such that all or a part of the first portion of the second composition is ingested by the ruminant; (g) providing a third composition comprising bromoform, wherein a concentration of bromoform in the third composition is about 0.01 wt % to about 20 wt %, wherein the bromoform is not derived from a biomass; (h) providing a second ingestible product (e.g., a feed, a bolus, a salt lick, or water) the second ingestible product being suitable for ingestion by the ruminant; (i) placing the second ingestible product and/or the third composition in a third vessel, wherein a volume of the vessel is at least 10 mL; (j) combining a quantity of the third composition with the second ingestible product to produce a fourth composition such that the third composition is coated on the second ingestible product, dispersed within the second ingestible product, or a combination thereof, wherein the concentration of bromoform in the fouth composition is about 0.0001 wt % to about 1 wt %; (k) placing the fourth composition in a second vessel to hold a mass of the second composition (e.g., wherein a volume of the fourth vessel is sufficient for provision to the ruminant); (l) providing to the ruminant a first portion of the fourth composition in a manner such that all or a part of the first portion of the fourth composition is ingested by the ruminant, wherein a period of time between (f) and (l) is about 1 day to about 1 year (e.g., about 2 days, about 1 week, about 1 month, about 6 months); and (m) optionally repeating (a)-(f) or (g)-(l) one or more times, thereby reducing methane expelled from the ruminant by at about 30% or more, over a period of time (e.g., at least 1 week, at least 1 month, at least 6 months, at least 1 year).

In one aspect, described herein is a method for reducing an amount of methane expelled from a ruminant by about 30% or more, the method comprising: (a) providing a first composition comprising bromoform, wherein a concentration of bromoform in the first composition is about 0.01 wt % to about 20 wt %, wherein the bromoform is not derived from a biomass; (b) providing a first ingestible product (e.g., a feed, a bolus, a salt lick, or water), the first ingestible product being suitable for ingestion by the ruminant; (c) optionally placing the first ingestible product and/or the first composition in a first vessel, wherein a volume of the vessel is at least 10 mL; (d) combining a quantity of the first composition with the first ingestible product to produce a second composition such that the first composition is coated on the first ingestible product, dispersed within the first ingestible product, or a combination thereof, wherein the concentration of bromoform in the second composition is about 0.0001 wt % to about 1 wt %; (e) optionally placing the second composition in a second vessel to hold a mass of the second composition (e.g., wherein a volume of the second vessel is sufficient for provision to the ruminant); and (f) providing to the ruminant a first portion of the second composition in a manner such that all or a part of the first portion of the second composition is ingested by the ruminant.

In one aspect, described herein is a method for reducing an amount of methane expelled from a ruminant by about 30% or more, the method comprising: (a) providing a first composition comprising bromoform, wherein a concentration of bromoform in the first composition is about 0.01 wt % to about 20 wt %, wherein the bromoform is not derived from a biomass; (b) providing a first ingestible product (e.g., a feed, a bolus, a salt lick, or water), the first ingestible product being suitable for ingestion by the ruminant; (c) placing the first ingestible product and/or the first composition in a first vessel, wherein a volume of the vessel is at least 10 mL; (d) combining a quantity of the first composition with the first ingestible product to produce a second composition such that the first composition is coated on the first ingestible product, dispersed within the first ingestible product, or a combination thereof, wherein the concentration of bromoform in the second composition is about 0.0001 wt % to about 1 wt %; (e) placing the second composition in a second vessel to hold a mass of the second composition (e.g., wherein a volume of the second vessel is sufficient for provision to the ruminant); and (f) providing to the ruminant a first portion of the second composition in a manner such that all or a part of the first portion of the second composition is ingested by the ruminant.

In some embodiments, the method for reducing an amount of methane expelled from a ruminant further comprises (g) providing a third composition comprising bromoform, wherein a concentration of bromoform in the third composition is about 0.01 wt % to about 20 wt %, wherein the bromoform is not derived from a biomass; (h) providing a second ingestible product (e.g., a feed, a bolus, a salt lick, or water) the second ingestible product being suitable for ingestion by the ruminant; (i) optionally placing the second ingestible product and/or the third composition in a third vessel, wherein a volume of the vessel is at least 10 mL; (j) combining a quantity of the third composition with the second ingestible product to produce a fourth composition such that the third composition is coated on the second ingestible product, dispersed within the second ingestible product, or a combination thereof, wherein the concentration of bromoform in the fourth composition is about 0.0001 wt % to about 1 wt %; (k) optionally placing the fourth composition in a second vessel to hold a mass of the second composition (e.g., wherein a volume of the fourth vessel is sufficient for provision to the ruminant); (l) providing to the ruminant a first portion of the fourth composition in a manner such that all or a part of the first portion of the fourth composition is ingested by the ruminant, wherein a period of time between (f) and (1) is about 1 day to about 1 year (e.g., about 2 days, about 1 week, about 1 month, about 6 months); and (m) optionally repeating (a)-(f) or (g)-(1) one or more times, thereby reducing methane expelled from the ruminant by at about 30% or more, over a period of time (e.g., at least 1 week, at least 1 month, at least 6 months, at least 1 year).

In some embodiments, the method for reducing an amount of methane expelled from a ruminant further comprises (g) providing a third composition comprising bromoform, wherein a concentration of bromoform in the third composition is about 0.01 wt % to about 20 wt %, wherein the bromoform is not derived from a biomass; (h) providing a second ingestible product (e.g., a feed, a bolus, a salt lick, or water) the second ingestible product being suitable for ingestion by the ruminant; (i) placing the second ingestible product and/or the third composition in a third vessel, wherein a volume of the vessel is at least 10 mL; (j) combining a quantity of the third composition with the second ingestible product to produce a fourth composition such that the third composition is coated on the second ingestible product, dispersed within the second ingestible product, or a combination thereof, wherein the concentration of bromoform in the fourth composition is about 0.0001 wt % to about 1 wt %; (k) placing the fourth composition in a second vessel to hold a mass of the second composition (e.g., wherein a volume of the fourth vessel is sufficient for provision to the ruminant); (l) providing to the ruminant a first portion of the fourth composition in a manner such that all or a part of the first portion of the fourth composition is ingested by the ruminant, In some embodiments, a period of time between providing a composition to the ruminant such that a portion of the composition is ingestible by the ruminant is about 1 day to about 1 year. In some embodiments the time period between providing a composition to the ruminant is about 1 day. In some embodiments the time period between providing a composition to the ruminant is about 1 year. In some embodiments the time period between providing a composition to the ruminant is about 2 days. In some embodiments the time period between providing a composition to the ruminant is about 1 week. In some embodiments the time period between providing a composition to the ruminant is about 1 month. In some embodiments the time period between providing a composition to the ruminant is about 6 months.

In some embodiments, the method further comprises repeating (a)-(f) one or more times, thereby reducing methane expelled from the ruminant by at about 30% or more, over a period of time. In some embodiments, the method further comprises repeating (g)-(1) one or more times, thereby reducing methane expelled from the ruminant by at about 30% or more, over a period of time. In some embodiments, a period of time is at least 1 week. In some embodiments, a period of time is at least 1 month. In some embodiments, a period of time is at least 6 months. In some embodiments, a period of time is at least 1 year.

In some embodiments, repeating comprises providing the same composition to the ruminant for ingestion. For example, a batch of a composition comprising bromoform and the feed or water is prepared and the ruminant is periodically provided portions of the batch for ingestion.

In some embodiments, repeating comprises providing a different composition to the ruminant for ingestion. For example, a composition comprising bromoform and feed or water is prepared and provided to the ruminant for ingestion and after a period of time, a different composition comprising bromoform and feed or water is provided to the ruminant for ingestion. In such examples, the composition comprising bromoform (e.g., first composition or third composition), the feed or water (e.g., first ingestible product or second ingestible product), or both are different between the first providing to the ruminant for ingestion and the second providing to the ruminant for ingestion.

In some embodiments, methane expelled from a ruminant is reduced by about 30% or more in comparison to a same or similarly situated ruminant provided the same or similar ingestible product (e.g., first ingestible product or second ingestible product) in the absence of the first composition or the third composition (e.g., in the absence of bromoform or in the absence of the same mass of bromoform).

In some embodiments, a first composition and a third composition are provided from a same stock (e.g., batch) of a composition comprising bromoform. In some embodiments, the first composition and the third composition are the same.

In some embodiments, a first composition and a third composition are different.

In some embodiments, a first ingestible composition and a second ingestible composition are the same. In some embodiments, a first ingestible composition and a second ingestible composition are different. In some embodiments, an ingestible product is a feed (e.g., feed of the disclosure) or water.

In some embodiments, the second composition and the fourth composition are the same. In some embodiments, the second composition and the fourth composition are different.

In some embodiments, the second vessel and the fourth vessel are the same. In some embodiments, the second vessel and the fourth vessel are different. In some embodiments, the first vessel and the third vessel are the same. In some embodiments, the first vessel and the third vessel are different.

In some embodiments, the method further comprises providing to the ruminant a second portion of the second composition such that the second portion of the second composition is ingested by the ruminant at a second time point after administering the first portion of the second composition (e.g., about 1 day, about 2 days, about 1 week, about 1 month, about 6 months).

In some embodiments, the method further comprises providing to the ruminant a second portion of the fourth composition such that the second portion of the fourth composition is ingested by the ruminant at a second time point after administering the first portion of the fourth composition (e.g., about 1 day, about 2 days, about 1 week, about 1 month, about 6 months).

Longevity of Methane Reduction

In some embodiments, the amount (e.g., volume or mass) of methane produced stays consistently below a threshold in between a first administration of a composition of the disclosure and a second administration of a composition of the disclosure. In some embodiments, the amount (e.g., volume or mass) of methane produced stays consistently below a threshold for a period of time upon at least a daily (e.g., at least an every other day, at least a weekly, at least a monthly) administration of a composition of the disclosure. In some embodiments, the amount of (e.g., volume or mass) of methane produced stays consistently below a threshold, in comparison to a control not comprising haloalkane, over the course of at least 2 days. In some embodiments, the amount of (e.g., volume or mass) of methane produced stays consistently below a threshold over the course of at least 5 days. In some embodiments, the amount of (e.g., volume or mass) of methane produced stays consistently below a threshold over the course of at least 1 week. In some embodiments, the amount of (e.g., volume or mass) of methane produced stays consistently below a threshold over the course of at least 2 weeks. In some embodiments, the amount of (e.g. volume or mass) of methane produced stays consistently below a threshold over the course of at least 3 weeks. In some embodiments, the amount of (e.g., volume or mass) of methane produced stays consistently below a threshold over the course of at least 1 month. In some embodiments, the amount of (e.g., volume or mass) of methane produced stays consistently below a threshold over the course of at least 2 months.

In some embodiments, the amount (e.g., volume or mass) of methane produced is consistently at least 40% less than a control (e.g., not comprising bromoform) over the course of about 2 weeks when a composition of the disclosure is administered on day 1. In some embodiments, the amount (e.g., volume or mass) of methane produced is consistently at least 40% less than a control (e.g., not comprising bromoform) over the course of about 2 weeks when a composition of the disclosure is administered each day of the about 2 weeks. In some embodiments, the amount (e.g., volume or mass) of methane produced is consistently at least 40% less than a control (e.g., not comprising bromoform) over the course of about 2 weeks when a composition of the disclosure is administered on day 1 and about day 7.

In some embodiments, the amount (e.g., volume or mass) of methane expelled by a ruminant is consistently at a reduced amount (e.g., volume or mass) in between administration and ingestion of the composition. For example, a ruminant ingesting a composition may have reduced methane expulsion by about 30% on the day of ingesting the composition, and the reduction of methane expulsion stays at about 30% until the next administration and ingestion of the composition by the ruminant.

In some embodiments, a rate of the amount (e.g., volume or mass) of methane expelled from a ruminant per day varies at most by about 60% over a period of at least 7 days, in comparison to a similarly situated ruminant not administered the consumable composition. In some embodiments, a rate of the amount (e.g., volume or mass) of methane expelled from a ruminant per day varies at most by about 60% over a period of at least 14 days, in comparison to a similarly situated ruminant not administered the consumable composition. For example, the amount (e.g., volume or mass) of methane expelled from a ruminant may be about 2 L on day one after administration of a consumable composition of the disclosure, and the amount (e.g., volume or mass) of methane expelled from the ruminant may be about 2.6 L on day seven after administration of the consumable composition.

In some embodiments, the amount (e.g., volume or mass) of methane expelled by a ruminant is non-uniform in between administration and ingestion of the composition. For example, a ruminant ingesting a composition may have reduced methane expulsion by about 30% on the day of ingestion the composition, and the reduction of methane expulsion may be at 10% 7 days after the initial ingestion of the composition.

Methods of Measuring Methane Production

In some embodiments, a composition of the disclosure is utilized for reducing the volume of methane expelled from a ruminant. In some embodiments, the composition of the disclosure is administered to a ruminant and the volume of methane reduction is determined in comparison to an otherwise similarly situated ruminant not administered the composition. Methane production can be measured using any suitable method.

In some instances, the results of an in vitro experiment to measure methane production can be used as a proxy for in vivo methane production.

In some embodiments, the efficacy of a composition of the disclosure in reducing methane production is evaluated through in vitro methods known in the art. In some embodiments, methane production is measured using an in vitro batch fermentation (IVFT) assay. In some embodiments, methane production is measured using an in vitro Rusitec experiment. In vitro determination of the reduction of methane production in comparison to a control sample may follow a procedure known in the art.

In some embodiments, the IVFT assay relies on simulating conditions and processes of the rumen. In some embodiments, ruminal inoculum is combined with a feed comprising a composition of the disclosure in a fermentation vessel. In some embodiments, the feed is fermented by rumen microbes over a period of time and microbial activity is assessed by measuring fermentation end-products. In some embodiments, fermentation end-products comprise microbial gas (e.g., total gas or methane), volatile fatty acids, and ammonia. In some embodiments, IVFT is used to screen the efficacy of reducing methane of a composition of the disclosure.

In some embodiments the Rusitec experiment provides a more comprehensive investigation of fermentation characteristics in comparison to the IVFT assay. In some embodiments, the Rusitec experiment relies on simulating conditions and processes of the rumen. In some embodiments, ruminal inoculum is combined with a feed comprising a composition of the disclosure in a fermentation vessel. In some embodiments, the feed is fermented by rumen microbes over a period of time and microbial activity is assessed by measuring fermentation end-products. In some embodiments, fermentation end-products comprise microbial gas (e.g., total gas or methane), volatile fatty acids, and ammonia. In some embodiments, the Rusitec experiment is used to screen the efficacy of reducing methane of a composition of the disclosure. In some embodiments, the Rusitec experiment closely replicates an in vivo process. In some embodiments, the Rusitec experiment comprises adding a fresh feed each day of the experiment. In some embodiments, the Rusitec experiment comprises removing undigested residue each day of the experiment. In some embodiments, the Rusitec experiment comprises a continuous flow of artificial saliva (e.g., buffer) in to the reaction. In some embodiments, the Rusitec experiment comprises a continuous flow of end-products (e.g., gas, VFA, ammonia) out of the reaction. In some embodiments, the Rusitec experiment provides efficacy of a composition of the disclosure over the course of up to two weeks. In some embodiments, persistence of an effect (e.g., reduced methane production) or any negative effect on fermentation may be discovered for a composition of the disclosure.

In some embodiments, the efficacy of a composition of the disclosure in reducing methane production is evaluated through in vivo methods known in the art. In some embodiments, an instrument to analyze in vivo expulsion of methane from a ruminant is used to measure methane production from a ruminant. In some embodiments, a laser is used to measure methane production from a ruminant. In some embodiments, a non-dispersive infrared (NDIR) breath analyzer is installed in a feed bin may be used to determined methane production from a ruminant. In some embodiments, a Fourier-transform infrared FTIR) breath analyzer is installed in a feed bin may be used to determined methane production from a ruminant.

In some embodiments, in vivo methane production is measured using an open-circuit respiration chamber as known in the art. In some embodiments, in vivo methane production is measured using a greenfed breath analyzer station as known in the art. In some embodiments, in vivo methane production is measured using a sulfur hexafluoride ($SF_6$) tracer technique as known in the art.

Efficacy of Compositions for Methane Reduction

Provided in FIGS. 8-12 are methane abatement (% $CH_4$ reduction) results of the IVFT assay for compositions of the disclosure at a dose of bromoform of 0.03 g/kg (g bromoform per kg of dry matter intake), 0.15 g/kg, and 0.3 g/kg. In some embodiments, additional doses of bromoform are measured for efficacy towards methane abatement for select compositions of the disclosure. In some embodiments, a composition investigates methane abatement at a bromoform dose of 0.04 g/kg DMI, 0.08 g/kg, 0.12 g/kg, 0.16 g/kg, 0.20 g/kg, 0.24 g/kg, 0.28 g/kg, 0.40 g/kg, and 0.60 g/kg. In some embodiments, doses of bromoform below 0.03 g/kg are investigated for select compositions of the disclosure. In some embodiments, a composition investigates methane abatement at a bromoform dose of 0.002 g/kg, 0.004 g/kg, 0.008 g/kg, 0.12 g/kg, 0.016 g/kg, and 0.02 g/kg.

FIG. 8 provides methane abatement results for the solid compositions of the disclosure. In some embodiments, methane production is reduced by at least 40% with a bromoform concentration of about 0.04 g/kg DMI. In some embodiments, methane production is reduced by at least 40% with a bromoform concentration of about 0.04 g/kg DMI. In some embodiments, methane production is reduced by at least 40% with a bromoform concentration of about 0.04 g/kg DMI. In some embodiments, methane production is reduced by at least 90% with a bromoform concentration of about 0.04 g/kg DMI. In some embodiments, methane production is reduced by at least 15% with a bromoform concentration of about 0.08 g/kg DMI. In some embodiments, methane production is reduced by at least 90% with a bromoform concentration of about 0.08 g/kg DMI. In some embodiments, a formulation comprising at least about 0.12 g/kg of bromoform in a composition comprising bromoform, MCT, and milk powder reduces methane production by at least 90%. FIG. 9 provides methane abatement results for solid compositions (e.g., Formulation No. 27 and 28) at doses of 0.004 g/kg, 0.016 g/kg, 0.04 g/kg, and 0.08 g/kg. In some embodiments, a dose of about 0.004 g/kg, 0.016 g/kg, 0.04 g/kg, or 0.08 g/kg bromoform for solid compositions are not efficacious towards methane abatement.

FIG. 10 provides methane abatement results for the oil-based compositions of the disclosure. In some embodiments, methane production is reduced by at least 10% with a bromoform concentration of about 0.04 g/kg DMI. In some embodiments, methane production is reduced by at least 85 wt % with a bromoform concentration of about 0.04 g/kg DMI. In some embodiments, methane production is reduced by at least 90 wt % with a bromoform concentration of about 0.08 g/kg DMI. FIG. 11 provides methane abatement results for solid compositions (e.g., Formulation No. 31 and 32) at doses of 0.004 g/kg, 0.016 g/kg, 0.04 g/kg, and 0.08 g/kg. In some embodiments, a dose of at least about 0.04 g/kg of bromoform for oil-based compositions is efficacious towards methane reduction of at least 85 wt %.

FIG. 12 provides methane abatement results for the water-based compositions of the disclosure. In some embodiments, methane production is reduced by at least 90 wt % with a bromoform concentration of at least about 0.12 g/kg DMI. In some embodiments, methane production is reduced by at least 90 wt % with a bromoform concentration of at least about 0.15 g/kg DMI. In some embodiments, methane production is reduced by at least 90 wt % with a bromoform concentration of at least about 0.3 g/kg DMI.

FIGS. 13-15 provide methane abatement and persistence results for compositions of the disclosure as determined through a Rusitec experiment over the course of 14 days of treatment.

FIG. 13 provides methane abatement and persistence results for solid compositions of the disclosure. In some embodiments, a solid composition reduces methane production by about 100 wt % with a bromoform concentration of about 0.03 g/kg DMI, when administered daily. In some embodiments, a solid composition reduces methane production by about 75 wt % with a bromoform concentration of about 0.03 g/kg DMI, when administered every other day. In some embodiments, the efficacy of methane reduction persists (e.g., change is within 10 wt %) over the course of at least 7 days. In some embodiments, the efficacy of methane reduction persists (e.g., change is within 10 wt %) over the course of at least 14 days. In some embodiments, a powdered form a composition results in a higher reduction of methane in comparison to a slow release form of the composition. In some embodiments, a powdered form a composition results in a higher reduction of methane in comparison to a slow release form of the composition by about 2-fold. In some embodiments, administering a double dose (e.g., double concentration of bromoform) results in greater methane abatement than a single dose In some embodiments, administering a double dose (e.g., double concentration of bromoform) results in greater methane abatement than a single dose by about 3-fold.

FIG. 14 provides methane abatement and persistence results for the oil-based compositions of the disclosure. In some embodiments, a dose of about 0.04 g/kg DMI results in at least 95 wt % reduction of methane over the course of at least 14 days. In some embodiments, a dose of about 0.04 g/kg DMI results in about 100 wt % reduction of methane over the course of at least 14 days. In some embodiments, a dose of about 0.08 g/kg DMI results in about 100 wt % reduction of methane over the course of at least 14 days. In some embodiments, a dose of about 0.12 g/kg DMI results in about 100 wt % reduction of methane over the course of at least 14 days.

FIG. 15 provides methane abatement results for the water-based compositions of the disclosure. In some embodiments, a dose of about 0.12 g/kg DMI results in about 100 wt % reduction of methane over the course of at least 2 days. In some embodiments, a dose of about 0.12 g/kg DMI results in about 100 wt % reduction of methane over the course of at least 2 days. In some embodiments, a dose of about 0.02 g/kg DMI results in about 99 wt % reduction of methane over the course of at least 14 days. In some embodiments, a dose of about 0.11 g/kg DMI results in about 99 wt % reduction of methane over the course of at least 14 days. In some embodiments, a dose of about 0.0.002 g/kg DMI results in about 99 wt % reduction of methane over the course of at least 14 days. In some embodiments, a dose of about 0.0.002 g/kg DMI results in about 100 wt % reduction of methane over the course of at least 14 days. In some embodiments, a water-based composition can result in greater methane reduction (e.g., complete methane abatement) at a dose of bromoform of about 0.0002 g/kg DMI.

In some embodiments, as shown in FIGS. 8-18, Formulation No., No. or ID refers to the Formulation number of a composition as provided in Table 1. In some embodiments, as shown in FIGS. 8-18, dose refers to a category of a bromoform concentration being classified as ultra low, very low, low, medium, or high. In some embodiments, as shown in FIGS. 8-18, dose/frequency refers to a category of a bromoform concentration being classified as ultra low, very low, low, medium or high in addition to a variable of frequency of administering the dose.

In some embodiments, as shown in FIGS. 8-18, Final Bromo (mg) per vial refers to the mass of bromoform in an assay; for an IVFT assay, the vial is about 50 mL while for a Rusitec experiment, the vial is about 500 mL. In some embodiments, as shown in FIGS. 8-18, Final Conc (g/kg DMI) refers to the concentration of bromoform as expressed grams per kilogram of dry matter intake. In some embodiments, Dry Matter Intake is the total weight of feed the bromoform is added to. In some embodiments, Dry Matter Intake is the total weight of water the bromoform is added to. In some embodiments, as shown in FIGS. 8-18, % bioactive/DMI refers to a concentration of bioactive (e.g., bromoform) as an expression of percentage in a total amount of dry matter intake.

In some embodiments, as shown in FIGS. 8-18, % CH4 reduction refers to the percentage of methane reduced in comparison to a control comprising no bromoform. For example, if a % CH4 reduction is 0%, it means that no methane was reduced as a result of administering a composition comprising bromoform. For example, if a % CH4 reduction is 100%, it means that no methane was detected as a result of administering a composition comprising bromoform. For example, if a % CH4 reduction is 50%, it means that half the methane detected from the control study was detected as a result of administering a composition comprising bromoform. For example, if a % CH4 reduction is 90%, it means that one-tenth the methane detected from the control study was detected as a result of administering a composition comprising bromoform.

Effect of Rumen Source

FIGS. 16-18 provide in vitro fermentation batch assay results for solid, oil-based, and water-based compositions of the disclosure, respectively when conducted using cow rumen and using sheep rumen. FIG. 16 provides IVFT assay results for solid compositions of the disclosure at a range of bromoform dosing of about 0.04 g/kg to about 0.60 g/kg. FIG. 17 provides IVFT assay results for oil-based compositions of the disclosure at a range of bromoform dosing of about 0.04 g/kg to about 0.60 g/kg. FIG. 18 provides IVFT assay results for solid compositions of the disclosure at a range of bromoform dosing of about 0.04 g/kg to about 0.60 g/kg. In some embodiments, differences between methane abatement in a cow rumen and a sheep rumen are caused from differences in preparing the sample for the IVFT assay (e.g., not mixing sufficiently). In some embodiments, methane abatement is consistent between sheep rumen and cow rumen. In some embodiments, methane abatements results can be extrapolated from a sheep rumen to a cow rumen. In some embodiments, methane abatements results measured from a sheep rumen are used to predict methane abatement results for a cow rumen. In some embodiments, methane abatements results measured from a cow rumen are used to predict methane abatement results for a sheep rumen.

Methods of Administration

In some aspects, provided herein are methods of administering the consumable compositions of the present application.

In some aspects, the method comprises (a) providing any one of the consumable compositions described herein, and (b) diluting the consumable composition in or on a feed or a water for a ruminant. In some embodiments, the method further comprises (c) administering the feed or the water comprising the consumable composition to a ruminant. In some embodiments, the consumable composition is diluted in the feed. In some embodiments, diluting in the feed comprises coating the feed with the consumable composition. In some embodiments, the consumable composition is diluted with the water.

In some embodiments, the method comprises (a) providing the consumable oil-based composition of any one of the preceding claims; and (b) diluting the consumable oil-based composition in or on a feed or a water for a ruminant. In some embodiments, the method further comprises (c) administering the feed or the water comprising the consumable composition to a ruminant. In some embodiments, the consumable composition is diluted in the feed. In some embodiments, diluting in the feed comprises coating the feed with the consumable composition. In some embodiments, the consumable composition is diluted with the water.

In some embodiments, the method comprises: (a) providing the consumable water-based composition of any one of the preceding claims; and (b) diluting the consumable water-based composition in or on a feed or a water for a ruminant. In some embodiments, the method further comprises (c) administering the feed or the water comprising the consumable composition to a ruminant. In some embodiments, the consumable composition is diluted in the feed. In some embodiments, diluting in the feed comprises coating the feed with the consumable composition. In some embodiments, the consumable composition is diluted with the water.

In some embodiments, the method comprises: (a) providing the consumable semi-solid composition of any one of the preceding claims; and (b) diluting the consumable semi-solid composition in or on a feed or a water for a ruminant. In some embodiments, the method further comprises (c) administering the feed or the water comprising the consumable composition to a ruminant. In some embodiments, the consumable composition is diluted in the feed. In some embodiments, diluting in the feed comprises coating the feed with the consumable composition. In some embodiments, the consumable composition is diluted with the water.

In some embodiments, the method comprises: (a) providing the consumable solid composition of any one of the preceding claims; and (b) diluting the consumable solid composition in or on a feed or a water for a ruminant. In some embodiments, the method further comprises (c) administering the feed or the water comprising the consumable composition to a ruminant. In some embodiments, the consumable composition is diluted in the feed. In some embodiments, diluting in the feed comprises coating the feed with the consumable composition. In some embodiments, the consumable composition is diluted with the water.

Any feed suitable for administration to a ruminant may be used in the methods described herein. In some embodiments, the feed is any one of a bolus, a feed pellet, a mixed ration, a mineral ration, a mineral mix, a mixed ration comprising a mineral mix, or a salt lick. In some embodiments, the feed is a bolus. In some embodiments, the feed is a feed pellet. In some embodiments, the feed is a mixed ration. In some embodiments, the feed is a mineral ration. In some embodiments, the feed is a mineral mix. In some embodiments, the feed is a mixed ration comprising a mineral mix. In some embodiments, the feed is a salt lick.

In some embodiments, in some embodiments, the equivalent of about 0.1 g to about 250 g of the consumable composition is diluted in about 1 kg of feed. In some embodiments, the equivalent of about 0.1 g to about 0.5 g of the consumable composition is diluted in about 1 kg of the feed. In some embodiments, in some embodiments, the equivalent of about 0.5 g to about 5 g of the consumable composition is diluted in about 1 kg of the feed. In some embodiments, in some embodiments, the equivalent of about 5 g to about 10 g of the consumable composition is diluted in about 1 kg of the feed. In some embodiments, in some embodiments, the equivalent of about 10 g to about 25 g of the consumable composition is diluted in about 1 kg of the feed. In some embodiments, in some embodiments, the equivalent of about 25 g to about 50 g of the consumable composition is diluted in about 1 kg of the feed. In some embodiments, in some embodiments, the equivalent of about 50 to about 100 g of the consumable composition is diluted in about 1 kg of the feed. In some embodiments, in some embodiments, the equivalent of about 100 g to about 150 g of the consumable composition is diluted in about 1 kg of the feed. In some embodiments, in some embodiments, the equivalent of about 150 g to about 200 g of the consumable composition is diluted in about 1 kg of the feed. In some embodiments, in some embodiments, the equivalent of about 200 g to about 250 g of the consumable composition is diluted in about 1 kg of the feed. In some embodiments, in some embodiments, the equivalent of about 0.1 g to about 25 g of the consumable composition is diluted in about 1 kg of the feed. In some embodiments, in some embodiments, the equivalent of about 0.5 g to about 25 g of the consumable composition is diluted in about 1 kg of the feed. In some embodiments, in some embodiments, the equivalent of about 0.1 g to about 10 g of the consumable composition is diluted in about 1 kg of the feed. In some embodiments, in some embodiments, the equivalent of about 0.5 g to about 10 g of the consumable composition is diluted in about 1 kg of the feed. In some embodiments, in some embodiments, the equivalent of about 10 g to about 25 g of the consumable composition is diluted in about 1 kg of the feed. In some embodiments, about 1 mL to about 50 mL of a composition of the disclosure is coated on per (kilogram) kg of pellet. In some embodiments, about 10 mL to about 40 mL of a composition of the disclosure is coated on per kg of pellet. In some embodiments, about 12 mL to about 25 mL of a composition of the disclosure is coated on per kg of pellet. In some embodiments, about 1 mL to about 50 mL of a composition of the disclosure is pressed in per kg of pellet. In some embodiments, about 10 mL to about 40 mL of a composition of the disclosure is pressed in per kg of pellet. In some embodiments, about 12 mL to about 25 mL of a composition of the disclosure is pressed in per kg of pellet.

In some embodiments, the consumable composition is diluted in water. In some embodiments, the water is comprised in a trough.

In some embodiments, the equivalent of about 0.5 g to about 30 g of the consumable composition is diluted in about 1 L of water. In some embodiments, the equivalent of about 0.5 g to about 1 g of the consumable composition is diluted in about 1 L of water. In some embodiments, the equivalent of about 1 g to about 2.5 g of the consumable composition is diluted in about 1 L of water. In some embodiments, the equivalent of about 2.5 g to about 5 g of the consumable composition is diluted in about 1 L of water. In some embodiments, the equivalent of about 5 g to about 10 g of the consumable composition is diluted in about 1 L of water. In some embodiments, the equivalent of about 10 g to about 15 g of the consumable composition is diluted in about 1 L of water. In some embodiments, the equivalent of about 15 g to about 20 g of the consumable composition is diluted in about 1 L of water. In some embodiments, the equivalent of about 20 g to about 30 g of the consumable composition is diluted in about 1 L of water.

In some embodiments, the total amount of bromoform administered to a ruminant is about 50 mg to about 1600 mg per day. In some embodiments the total amount of bromoform administered to a ruminant is about 50 mg to about 100 mg per day. In some embodiments the total amount of bromoform administered to a ruminant is about 100 mg to about 150 mg per day. In some embodiments the total amount of bromoform administered to a ruminant is about 150 mg to about 200 mg per day. In some embodiments the total amount of bromoform administered to a ruminant is about 250 mg to about 300 mg per day. In some embodiments the total amount of bromoform administered to a ruminant is about 300 mg to about 350 mg per day. In some embodiments the total amount of bromoform administered to a ruminant is about 350 to about 400 mg per day. In some embodiments the total amount of bromoform administered to a ruminant is about 400 mg to about 450 mg per day. In some embodiments the total amount of bromoform administered to a ruminant is about 450 mg to about 500 mg per day. In some embodiments the total amount of bromoform administered to a ruminant is about 500 mg to about 550 mg per day. In some embodiments the total amount of bromoform administered to a ruminant is about 550 mg to about 600 mg per day. In some embodiments the total amount of bromoform administered to a ruminant is about 650 mg to about 700 mg per day. In some embodiments the total amount of bromoform administered to a ruminant is about 700 mg to about 750 mg per day. In some embodiments the total amount of bromoform administered to a ruminant is about 750 mg to about 800 mg per day. In some embodiments the total amount of bromoform administered to a ruminant is about 800 mg to about 850 mg per day. In some embodiments the total amount of bromoform administered to a ruminant is about 850 mg to about 900 mg per day. In some embodiments the total amount of bromoform administered to a ruminant is about 900 mg to about 950 mg per day. In some embodiments the total amount of bromoform administered to a ruminant is about 950 mg to about 1000 mg per day. In some embodiments the total amount of bromoform administered to a ruminant is about 1000 mg to about 1100 mg per day. In some embodiments the total amount of bromoform administered to a ruminant is about 1100 mg to about 1200 mg per day. In some embodiments the total amount of bromoform administered to a ruminant is about 1200 mg to about 1300 mg per day. In some embodiments the total amount of bromoform administered to a ruminant is about 1300 mg to about 1400 mg per day. In some embodiments the total amount of bromoform administered to a ruminant is about 1400 mg to about 1600 mg per day.

In some embodiments, the consumable composition is diluted in a bolus. In some embodiments, the consumable composition is concentrated in a bolus. In some embodiments, the consumable composition is combined in a bolus. In some embodiments, the bolus comprises about 0.002 wt % to about 50 wt % of the haloalkane. In some embodiments, the bolus comprises about 5 wt % to about 50 wt % of the haloalkane. In some embodiments, the bolus comprises about 10 wt % to about 50 wt % of the haloalkane. In some embodiments, the bolus comprises about 25 wt % to about 50 wt % of the haloalkane. In some embodiments, a bolus is configured to release about 50 mg to about 1500 mg of the haloalkane per day. In some embodiments, a bolus is configured to release about 50 mg to about 100 mg of the haloalkane per day. In some embodiments, a bolus is configured to release about 50 mg to about 80 mg of the haloalkane per day. In some embodiments, a bolus is configured to release about 80 mg to about 100 mg of the haloalkane per day. In some embodiments, a bolus is configured to release about 100 mg to about 150 mg of the haloalkane per day. In some embodiments, a bolus is configured to release about 150 mg to about 200 mg of the haloalkane per day. In some embodiments, two or more bolus are combined to achieve a total mass of the haloalkane. For example, two bolus each comprising about 25 mg of the haloalkane are administered to achieve a dose of about 50 mg of the haloalkane to the ruminant. In some embodiments, a bolus is administered to a ruminant daily. In some embodiments, a bolus is administered to a ruminant weekly. In some embodiments, a bolus is administered to a ruminant monthly. In some embodiments, a bolus is administered to a ruminant semi-annually. For example, a bolus to be administered to a ruminant semi-annually with a bioactive release rate of about 50 mg per day will comprise 9000 mg of the bioactive (e.g., haloalkane). For example, a 30 g bolus configured to release 50 mg of bromoform per day over the course of 6 months will comprise about 9000 mg of bromoform.

In some embodiments, a bolus comprises a stabilizing agent. In some embodiments, a bolus comprising casein.

The consumable composition may be administered to a ruminant in any suitable location. In some embodiments, the consumable composition is administered to a ruminant situated in a grazing field. In some aspects, the consumable composition is administered to a ruminant situated in a feedlot. In some aspects, the consumable composition is administered to a ruminant situated in a rangeland.

As provided in FIG. 6, oil-based compositions of the disclosure can be prepared for administering to a ruminant. In some embodiments, an oil-based composition is combined with a feed. In some embodiments, an oil-based composition is coated on top of a total mixed ration. In some embodiments, an oil-based composition is coated on top of a pellet supplement. In some embodiments, an oil-based composition is pressed inside a pellet supplement. In some embodiments, the oil composition coated on a mixed ration is administered to a ruminant in a feedlot. In some embodiments, an oil-based composition coated on top of a pellet supplement is administered to a free grazing ruminant. In some embodiments, an oil-based composition pressed inside a pellet supplement is administered to a free grazing ruminant or a feedlot ruminant. In some embodiments, the oil-based composition comprises a concentration of bromoform of about 1.25 g/L to about 16 g/L. In some embodiments, the oil-based composition is combined with a feed. In some embodiments, the concentration of bromoform in a feed to be administered to a ruminant is about 0.001 wt % bromoform of total dry matter intake (DMI) to about 0.35 wt % bromoform. In some embodiments, a ruminant is administered at most 5 wt % oil per day (e.g., weight of oil over weight of all feed intake). For example, a ruminant consumes 12 kg of feed per day; a feed for such a ruminant is prepared by combining up to 50 mL (e.g., 10 ml) of the oil composition per kilogram of feed. In some embodiments, about 25 mL of the oil composition is combined with 1 kg of pellet supplements and used to coat the pellet. In some embodiments, about 25 mL of the oil composition is combined with 1 kg of pellet supplements and pressed inside the pellet. In some embodiments, a ruminant is administered about 2 kg of supplement per day. As provided in FIG. 7, a solid composition of the disclosure can be prepared for administering to a ruminant. In some embodiments, a solid composition is mixed over pellet supplements. In some embodiments, a solid composition is pressed in pellet supplements. In some embodiments, a solid composition is mixed with a mineral mix. In some embodiments, a solid composition is mixed over a total mixed ration. In some embodiments, a solid composition is mixed with a total mixed ratio comprising a mineral mix. In some embodiments, a solid composition is combined with dried distillers grain. In some embodiments, a solid composition mixed over pellet supplements is administered to a free grazing ruminant. In some embodiments, a solid composition mixed with a mineral mix is administered to a free grazing ruminant. In some embodiments, a solid composition mixed with a mineral mix over a total mixed ration is administered to a ruminant in a feedlot. In some embodiments, the solid composition comprises a concentration of bromoform of about 10 g/kg of solid powder to about 80 g/kg. In some embodiments, the solid composition comprises a concentration of bromoform of about 50 g/kg of solid powder to about 75 g/kg. In some embodiments, the solid composition comprises a concentration of bromoform of about 15 g/kg of solid powder to about 30 g/kg. In some embodiments, the solid composition comprises a concentration of bromoform of about 15 g/kg of solid powder to about 25 g/kg. In some embodiments, the solid composition is combined with a feed. In some embodiments, the concentration of bromoform in a feed to be administered to a ruminant is about 0.0005 wt % bromoform of total dry matter intake (DMI) to about 0.25 wt % bromoform. In some embodiments, a ruminant is administered about 10 g of a solid composition per day. In some embodiments, about 10 g of a solid composition is combined 2 kg of supplement pellets with up to 50 mL of water to coat the solid composition onto the supplement pellets.

As provided in FIG. 7, a water-based composition of the disclosure can be prepared for administering to a ruminant. In some embodiments, a water-based composition is combined with water. In some embodiments, the water is administered through a trough to free grazing ruminant. In some embodiments, the water is administered through a trough to a rangeland ruminant. In some embodiments, the water is administered through a trough to feedlot ruminant. In some embodiments, a ruminant is administered about 40 mL of the water-based composition per day. In some embodiments, the water-based composition is further diluted in water. In some embodiments, a volume of the water-based composition is combined with a volume of water. In some embodiments, a volume of the water-based composition is combined with a volume of water sufficient to yield a pre-determined concentration of bromoform in a vessel (e.g., trough). In some embodiments, the water-based composition is an aqueous liquid. In some embodiments, the water-based composition is an aqueous gel. For example, 8 L of the water-based composition can be diluted with an additional 12 L of water to yield 20 L of water to be administered to a ruminant. In some embodiments, aliquots of the diluted water-based compositions can be prepared. In some embodiments, a 100 mL aliquot of the diluted water-based composition is combined with 10 L of water. In some embodiments, the water-based composition comprises a concentration of bromoform of about 1 g/L to about 15 g/L prior to diluting further with water. In some embodiments, the concentration of bromoform in a vessel is about 0.0002 wt % per liter to about 0.06 wt % per liter. In some embodiments, the concentration of bromoform in a vessel is about 0.0002 wt % per liter to about 0.0005 wt % per liter. In some embodiments, the concentration of bromoform in a vessel is about 0.0002 wt % per liter to about 0.001 wt % per liter. In some embodiments, the concentration of bromoform in a vessel is about 0.0002 wt % per liter to about 0.006 wt % per liter.

Increasing the period of time that lapses in between an administration of a composition of the disclosure (e.g., comprising a dose of bromoform) may improve efficiency of administering a bioactive composition to a ruminant. In some embodiments, a composition of the disclosure is administered to a ruminant daily (e.g., about every 24 hours). In some embodiments, a composition of the disclosure is administered to a ruminant every other day (e.g., about every 48 hours). In some embodiments, a composition of the disclosure is administered to a ruminant about every 72 hours. In some embodiments, a composition of the disclosure is administered to a ruminant about every 96 hours. In some embodiments, a composition of the disclosure is administered to a ruminant about every 120 hours. In some embodiments, a composition of the disclosure is administered to a ruminant about every 6 days. In some embodiments, a composition of the disclosure is administered to a ruminant about every 7 days. In some embodiments, a composition of the disclosure is administered to a ruminant about every 10 days. In some embodiments, a composition of the disclosure is administered to a ruminant about every 14 days. In some embodiments, a composition of the disclosure is administered to a ruminant about every 30 days. In some embodiments, a composition of the disclosure is administered to a ruminant about every 60 hours. In some embodiments, a composition of the disclosure is administered to a ruminant about every 3 months. In some embodiments, a composition of the disclosure is administered to a ruminant about every 4 months. In some embodiments, a composition of the disclosure is administered to a ruminant about every 5 months. In some embodiments, a composition of the disclosure is administered to a ruminant about every 6 months. In some embodiments, a composition of the disclosure is administered to a ruminant about every 1 year.

In some embodiments, a pellet comprises a dry material and an oil component (e.g., an oil-based composition of the disclosure). In some embodiments, a pellet comprises a dry material and a water component (e.g., a water-based composition of the disclosure). In some embodiments, a pellet comprises dry material. In some embodiments, a pellet comprising a composition of the disclosure pressed inside comprises a greater stability than a pellet comprising a composition of the disclosure coated on the outside. In some embodiments, stability comprises chemical stability (e.g., stability of haloalkane in a composition or feed). A pressed pellet is prepared according to a method as known in the art.

Palatability

In some embodiments, a composition of the disclosure may comprise increased palatability for a ruminant. In some embodiments, palatability may be assessed as a measurement of body weight gain over a period of time. In some embodiments, palatability may be assessed as a measurement of rate of consumption of a feed comprising a composition of the disclosure. In some embodiments, palatability of a composition of the disclosure is assessed against a control feed comprising no bioactive composition.

In some embodiments, a composition of the disclosure is more palatable to a ruminant than a composition comprising macroalgae.

In some embodiments, the palatability of a composition is a proxy for consumption of a feed or water comprising the composition. In some instances, a ruminant may not ingest as great of a quantity of a feed comprising a composition that is less palatable than a feed comprising a composition that is more palatable. In some embodiments, feed intake is a proxy for methane reduction. For example, a ruminant consuming a greater quantity of a feed comprising a composition of the disclosure may have greater methane reduction than an otherwise similarly situated ruminant consuming a lesser quantity of a feed comprising the composition of the disclosure. In some embodiments, a ruminant consuming a greater quantity of a feed comprising a composition of the disclosure expels a reduced volume (or mass) methane than an otherwise similarly situated ruminant consuming a lesser quantity of a feed comprising the composition of the disclosure.

In some embodiments, palatability of a composition of the disclosure is assessed against another composition of the disclosure not comprising a particular component (e.g., with or without MSG, with or without canola oil). As shown in FIG. 19a and FIG. 19e, ruminants on average consumed a feed comprising canola oil in a rate about 3 times greater than a feed not comprising canola oil as a taste enhancing agent. In some embodiments, a composition comprising a plant-based oil is more palatable than a composition not comprising the plant-based oil. In some embodiments, a composition comprising a plant-based oil is consumed by a ruminant at a greater rate than a composition not comprising the plant-based oil. In some embodiments, a composition comprising a plant-based oil is consumed by a ruminant at a rate about 2 times greater than a composition not comprising the plant-based oil. In some embodiments, a composition comprising a plant-based oil is consumed by a ruminant at a rate about 3 times greater than a composition not comprising the plant-based oil. In some embodiments, a composition comprising a plant-based oil is consumed by a ruminant at a rate about 4 times greater than a composition not comprising the plant-based oil.

In some embodiments, a composition comprising a lower concentration of MCT is more palatable than a composition comprising a greater concentration of MCT. In some embodiments, a composition comprising a lower concentration of MCT is consumed at a greater rate than a composition comprising a greater concentration of MCT. In some embodiments, a composition comprising a lower concentration of MCT is consumed at a rate about 2 times greater than a composition comprising a greater concentration of MCT. In some embodiments, a composition comprising a lower concentration of MCT is consumed at a rate about 3 times greater than a composition comprising a greater concentration of MCT. In some embodiments, a composition comprising a lower concentration of MCT is consumed at a rate about 4 times greater than a composition comprising a greater concentration of MCT. For example, as shown in FIG. 19a, a composition comprising only MCT and no plant based oil takes the ruminants about 35-60 minutes to consume, whereas, as shown in FIG. 19e, a composition comprising MCT and canola oil is consumed in about 15 minutes. For example, as shown in FIG. 19d ruminants consume pellets comprising MSG and not comprising MSG in about 15 minutes.

In some embodiments, a composition comprising a short chain oil is more palatable than a composition not comprising the short chain oil. In some embodiments, a composition comprising a short chain oil is consumed by a ruminant at a greater rate than a composition not comprising the short chain oil. In some embodiments, a composition comprising a short chain oil is consumed by a ruminant at a rate about 2 times greater than a composition not comprising the short chain oil. In some embodiments, a composition comprising a short chain oil is consumed by a ruminant at a rate about 3 times greater than a composition not comprising the short chain oil. In some embodiments, a composition comprising a short chain oil is consumed by a ruminant at a rate about 4 times greater than a composition not comprising the short chain oil.

In some embodiments, palatability of a composition of the disclosure is assessed against another composition of the disclosure comprising a different concentration of a component (e.g., 4 g/L bromoform vs 8 g/L bromoform). In some instances, as shown in FIG. 19a and FIG. 19b, the concentration of bromoform in a composition may have minimal effect on the palatability of a composition. In some instances, the concentration of bromoform in a composition may have minial effect on the palatability of a composition of the disclosure.

In some embodiments, palatability of a composition of the disclosure is assessed against the form of the composition (e.g., chunk vs. granule vs. powder or coated on pellet vs pressed in pellet). For example, as shown in FIG. 19c, a composition in a powdered form is more palatable than a composition in a more granular form. In some embodiments, a composition coated on a pellet takes the ruminants, on average, 35-60 minutes to consume where as a composition pressed inside a pellet takes the ruminants, on average, 15 minutes to consume. In some embodiments, a composition pressed inside a pellet is more palatable than a composition coated on a pellet. In some embodiments, a composition pressed inside a pellet is consumed by a ruminant at a rate of about 3 times greater than a composition coated on a pellet. In some embodiments, a composition in powder form is more palatable than composition in a granular or chunk form.

In some embodiments, a ruminant gains about 1% or more body weight over a period of about 1 week when ingesting a feed comprising a taste enhancing agent in comparison to when ingesting an ingestible product not comprising the taste enhancing agent. In some embodiments, a ruminat gains about 1% or more body weight over a period of about 2 weeks when ingesting an ingestible product comprising a taste enhancing agent in comparison to when ingesting a feed not comprising the taste enhancing agent. In some embodiments, a ruminant gains about 5% or more body weight over a period of about 1 week when ingesting a feed comprising a taste enhancing agent in comparison to when ingesting an ingestible product not comprising the taste enhancing agent. In some embodiments, a ruminant gains about 5% or more body weight over a period of about 2 weeks when ingesting an ingestible product comprising a taste enhancing agent in comparison to when ingesting a feed not comprising the taste enhancing agent.

Examples

The following examples are provided to further illustrate some embodiments of the present disclosure, but are not intended to limit the scope of the disclosure; it will be understood by their exemplary nature that other procedures, methodologies, or techniques known to those skilled in the art may alternatively be used.

Example 1: Composition of Formulations

Provided in Table 1 are examples of the compositions of the disclosure.

TABLE 1

Illustrative Compositions

| Formulation No. | Type | Components | Note |
|---|---|---|---|
| 1 | Milk-Based Liquid | Bromoform, fresh milk, MCT | Stock (142 mg/mL Bromoform) Prepared using 38 mL MCT, 0.25-1 mL of Ethanol, and 2 mL of Bromoform. Stock is diluted with fresh pasteurized milk to target concentration for trial. Various concentrations prepared - milk only, 1.5 mg/mL bromoform, 0.75 mg/mL and 0.15 mg/mL. For example, 200 mL of Formulation 1 with 0.15 mg/mL bromoform is prepared by diluting 0.211 mL of stock to volume with fresh milk to yield composition with 0.1% MCT. |
| 2 | Milk-based Liquid | Bromoform, milk powder, MCT | 29 g milk powder/200 mL water solution is prepared. Stock(142 mg/mL Bromoform) Prepared using 38 mL MCT, 0.25-1 mL of Ethanol, 2 mL of Bromoform. Small volume (e.g., about 0.2 mL to about 2.2 mL) of spike added to the milk powder solution to target concentration for trial. Various concentrations prepared - milk powder solution only, 1.5 mg/mL bromoform, 0.75 mg/mL and 0.15 mg/mL |
| 3 | Milk-based liquid | Bromoform, double mass milk powder, MCT | 58 g milk powder/200 mL water solution is prepared. Stock (142 mg/mL Bromoform) is prepared using 38 mL MCT, 0.25-1 mL of Ethanol, and 2 mL of Bromoform. Small volume (0.2-2.2 mL) of spike added to the milk powder solution to target concentration for trial. Various concentrations prepared - milk powder solution only, 1.5 mg/mL bromoform, 0.75 mg/mL and 0.15 mg/mL |
| 4 | Milk-based Liquid | Bromoform, milk powder (infant formula), MCT | 4 scoops of infant formula powder (e.g., 4.3 g per scoop) into 200 mL hot water (60 C.-80 C.) prepared. Stock (142 mg/mL Bromoform) Prepared using 38 mL MCT, 0.25-1 mL of Ethanol, and 2 mL of Bromoform. Small volume of spike added to the infant formula powder solution to target concentration for trial. Various concentrations prepared - infant formula powdersolution only, 1.5 mg/mL bromoform, 0.75 mg/mL and 0.15 mg/mL |
| 5 | Oil | Bromoform, MCT | Stock (144.5 mg/mL Bromoform) Prepared using 25 mL MCT, 0.25-0.75 mL of Ethanol, and 2 mL of Bromoform. Stock is diluted with MCT to target concentration for trial. |
| 7 | Solid | Bromoform, milk powder, gelatin | 25 g Milk Powder, 20 g of Gelatin Powder, 175 mL Water, Bromoform to Dose. Prep Strategy Milk Powder and Water first. then Bromoform. then Gelatin. Mix and pour into moulds. |
| 9 | Liquid | Bromoform, milk powder, MCT | Stock (142 mg/mL Bromoform) Prepared using 38 mL MCT, 0.25-1 mL of Ethanol, and 2 mL of Bromoform. 58 g milk powder/200 mL water milk powder solution prepared. Milk powder solution spiked with stock solution to dose. Various concentrations prepared - 0 to 3 mg/mL range |
| 10 | Solid | Bromoform, milk powder, gelatin | Stock (142 mg/mL Bromoform) Prepared using 38 mL MCT, 0.25-1 mL of Ethanol, and 2 mL of Bromoform. 58 g milk powder/200 mL water, 20 g gelatin milk powder gelatin solution prepared. Milk powder gelatin solution spiked with stock solution to dose. Various concentrations prepared - 0 to 3 mg/mL range |

TABLE 1-continued

Illustrative Compositions

| Formulation No. | Type | Components | Note |
|---|---|---|---|
| 11 | Oil | Bromoform, MCT | Stock (142 mg/mL Bromoform) Prepared is 38 mL MCT, 0.25-1 mL of Ethanol, 2 mL of Bromoform. Stock is diluted with MCT to achieve target concentrations of bromoform. |
| 12 | Water | Bromoform, water, lecithin | Water (350 mL) and Lecithin (3.5 mL) prepared. Bromoform (0.5 mL) added to prepare a stock of this solution. This was then diluted using a matched lecithin/water (1% lecithin) solution to hit dose. |
| 13 | Water | Bromoform, water, lecithin, xanthan gum | Water (350 mL) and Lecithin (3.5 mL) and Xanthan Gum (1.5 g) prepared. Bromoform (0.5 mL) added to prepare a stock of this solution. This was then diluted using a matched lecithin/water (1% lecithin) solution to hit dose. |
| 14 | Water | Bromoform, water, MCT, lecithin, | Water (350 mL) and Lecithin (3.5 mL) prepared. Bromoform (0.2 mL) was added to MCT (30 mL). This MCT/Bromoform Solution was then spiked to hit dose in water/lecithin solution. |
| 15 | Water | Bromoform, water, MCT, lecithin, xanthan gum | Water (330 mL) and Lecithin (5 g) and Xanthan Gum (1 g) prepared. Bromoform (2 mL) was added to MCT (38 mL). This MCT/Bromoform Solution was then spiked to hit dose in water/lecithin/gum solution. |
| 17 | Water | Bromoform, water, MCT, lecithin, xanthan gum | Water (350 mL), Lecithin (3.5 mL) and Xanthum Gum (0.15 g) prepared. Bromoform (0.7 mL) was added to MCT (38 mL) with Ethanol (0.8 mL). This MCT/Bromoform Solution was then added to to achieve target concentration in water/lecithin/gum solution. |
| 18 | Water | Bromoform, water, Tween | Water (350 mL), Xanthan Gum (0.15 g) and Tween (0.8%/v) prepared. Bromoform was added to achieve target concentration. |
| 19 | Water | Bromoform, water, MCT, Tween, xanthan gum | Water (350 mL) and Tween (0.8%/v) and Xanthan Gum (0.05%) prepared. Bromoform (0.7 mL) was added to MCT (38 mL) with Ethanol (0.8 mL). This MCT/Bromoform Solution was then added to water/tween/gum solution to achieve target concentration. |
| 20 | Solid | Bromoform, milk powder, gelatin | 50 g Milk Powder with 49 g hot water (60 C.-80 C.), 28 g of Gelatin Powder with 49 g of hot water. Mix together with additional 98 g hot water. (196 g water total). Bromoform spike solution prepared using 0.5 mL bromoform into milk solution (22 g milk powder and 20 mL hot water). Mix and pour into moulds. 1.18 mL of the bromoform spiked solution added to Milk Powder/gelatin mix and pour into moulds. |
| 21 | Oil | Bromoform, MCT | Stock (144.5 mg/mL Bromoform) Prepared using 25 mL MCT, 0.25-0.75 mL of Ethanol, and 2 mL of Bromoform. Diluted with MCT to target concentration for trial. |
| 22 | Oil | Bromoform, MCT, Kolliphor | Stock (142/mL Bromoform) Prepared using 50 mL MCT, 1 mL of Ethanol, 1 mL of Bromoform and Kolliphor EL (1%). Diluted with MCT to target concentration for trial. |
| 23 | Oil | Bromoform, MCT, canola oil | Bromoform (1 mL) is added to MCT (12.5 mL) and Ethanol (5 mL). This solution is mixed into Canola oil (230 mL). Diluted with Canola oil to target concentration for trial. |
| 24 | Oil | Bromoform, MCT, canola oil, Kolliphor | Bromoform (1 mL) is added to MCT (12.5 mL) and Ethanol (5 mL). This solution is mixed into Canola oil (230 mL) and Kolliphor (1% wt %). Diluted with Canola/Kolliphor solution to target concentration for trial. |
| 25 | Solid | Bromoform, MCT, milk powder, gelatin | Active Stock prepared using 250 g Milk Powder, 138 g of Gelatin Powder, 864 mL Water, and Bromoform (108 ul). Dilutionary Stock: 100 g Milk Powder, 55 g of Gelatin Powder, 345 mL Water. Active stock is combined with dilutionary stock to prepare various concentrations prepared - 0 to 1 mg/mL range. |

TABLE 1-continued

Illustrative Compositions

| Formulation No. | Type | Components | Note |
|---|---|---|---|
| 26 | Solid | Bromoform, milk powder, monosodium glutamate | Active Stock prepared using 250 g Milk Powder, 138 g of Gelatin Powder, 864 mL Water, 43 g of MSG and Bromoform (120 ul). Dilutionary Stock: 100 g Milk Powder, 55 g of Gelatin Powder, 345 mL Water and 43 g of MSG. Active stock is combined with dilutionary stock to prepare various concentrations prepared - 0 to 1 mg/mL range. |
| 27 | Solid | Bromoform, milk powder, MCT | Active Stock prepared using 150 g Milk Powder, 84 g of Gelatin Powder, 600 mL Water, MCT (2 mL) and Bromoform (0.8 mL). Dilutionary Stock: 150 g Milk Powder, 84 g of Gelatin Powder, 600 mL Water and MCT (12 mL), Active stock is combined with dilutionary stock to prepare various concentrations prepared - 0 to 1 mg/mL range. |
| 28 | Solid | Bromoform, milk powder, MCT, lecithin | Active Stock prepared using 150 g Milk Powder, 84 g of Gelatin Powder, 600 mL Water, MCT (8 mL), Lecithin (0.25 g) and Bromoform (0.8 mL) to dose. Dilutionary Stock: 150 g Milk Powder, 84 g of Gelatin Powder, 600 mL Water, MCT (8 mL) and Lecithin (0.25 g). Active stock is combined with dilutionary stock to prepare various concentrations prepared - 0 to 1 mg/mL range. |
| 29 | Solid | Bromoform, casein, MCT | Active Stock: 250 g Casein Powder, 138 g of Gelatin Powder, 1000 mL Water, MCT (0.5 mL), and Bromoform (161 ul). Dilutionary Stock: 250 g Casein Powder, 138 g of Gelatin Powder, 1000 mL Water, MCT (0.5 mL). Active stock is combined with dilutionary stock to prepare various concentrations prepared - 0 to 1 mg/mL range. |
| 30 | Solid | Bromoform, casein, MCT, lecithin | Active Stock: 150 g Casein Powder, 84 g of Gelatin Powder, 600 mL Water, MCT (0.5 mL), Lecithin (3 g) and Bromoform (161 ul) Dilutionary Stock: 150 g Casein Powder, 84 g of Gelatin Powder, 600 mL Water, MCT (0.5 mL) and Lecithin (3 g). Active stock is combined with dilutionary stock to prepare various concentrations prepared - 0 to 1 mg/mL range. |
| 31 | Oil | Bromoform, MCT, canola | Active Stock: MCT (20 mL), Ethanol (8.8 mL) and Bromoform (300 microlitres) are combined into Canola oil (400 mL). Dilutionary Stock: MCT (20 mL), Ethanol (8.8 mL) and Canola oil (400 mL) are combined. Active stock is combined with dilutionary stock to prepare various concentrations. |
| 32 | Oil | Bromoform, MCT, canola, Kolliphor | Active Stock: MCT (20 mL), Ethanol (8.8 mL) and Bromoform (300 microlitres) are combined into Canola oil (400 mL) containing Kolliphor (4 mL). Dilutionary Stock: MCT (20 mL), Ethanol (8.8 mL), Canola oil (400 mL) and Kolliphor (4 mL) are combined. Active stock is combined with dilutionary stock to prepare various concentrations. |
| 33 | Oil | Bromoform, MCT, canola, water | Active Stock: MCT (15 mL) and Bromoform (230 microlitres) are combined with a solution containing Water (15 mL) and Tween (3.3 mL). Canola oil (300 mL) added. Dilutionary Stock: MCT (15 mL), Water (15 mL), Tween (3.3 mL) and Canola oil (300 mL) are combined. Active stock is combined with dilutionary stock to prepare various concentrations. |
| 9i | Milk-based Liquid | | 53 g Milk Powder, Made up to 185 g with hot water = Milk Solution. Stock of bromoform made with this milk solution via the addition of bromoform and then diluted with milk solution to dose. |

TABLE 1-continued

Illustrative Compositions

| Formulation No. | Type | Components | Note |
|---|---|---|---|
| 10i | Solid | | 50 g Milk Powder, 20 g Gelatin Powder made up to 175 g of water. Bromoform added to deliver target dose concentration. |
| 17i | Water | | Water (350 mL) and Lecithin (3.5 mL) and Xanthan Gum (1.5 g) prepared. Bromoform (0.2 mL) was added to MCT (30 mL). This MCT/Bromoform Solution was then spiked to hit dose in water/lecithin/gum solution. |

The concentration of bromoform can be adjusted for each of the compositions of Table 1 as required by a dose. In some embodiments, a concentration of bromoform is adjusted through increasing or decreasing the volume of a stock (e.g., spike solution or active stock) when combining with an otherwise similar non-bioactive composition (e.g., dilutionary stock).

Formulation No. 9i, 10i, and 17i are identical in composition for Formulation No. 9, 10, and 17, respectively. IVFT and Rusitec experiment results corresponding to Formulation No. 9, 10, and 17 utilize 9i, 10i, and 17i respectively.

Example 2: Synthesis of Oil-Based Composition, Formulation No. 31

A general schematic illustrating how to prepare an oil-based composition is shown in FIG. 1. To make about 25 L of the oil-based composition at a concentration of about 14 g/L (g bromoform per liter), about 350 g (121.1 ml) bromoform is dissolved in 500 mL ethanol. The solution of bromoform and ethanol is mixed with about 1250 mL of MCT. The solution comprising bromoform, ethanol, and MCT is mixed with 23.2 L canola oil to reach a final dilution and yield 25 L of the composition.

Example 3: Synthesis of Oil-Based Composition, Formulation No. 32

A general schematic illustrating how to prepare an oil-based composition is shown in FIG. 1. To make about 1 L of the oil-based composition, a predetermined mass of bromoform is dissolved in ethanol, the mass being determined by the anticipated dose or concentration of bromoform desired for a final product or composition. The mass of bromoform dissolved in ethanol can be about 1 g to about 20 g. The volume of ethanol is kept at a minimum, not exceeding 20 mL. The solution of bromoform and ethanol is mixed with about 50 mL of MCT. About 10 mL of Koliphor® is added to the solution, before diluting the composition with canola oil, about 920 mL to yield 1 L of the oil-based composition.

Example 4: Synthesis of Oil-Based Composition Comprising Essential Oil

A general schematic illustrating how to prepare an oil-based composition is shown in FIG. 1. To make about 1 L of the oil-based composition, a predetermined mass of bromoform is dissolved in ethanol, the mass being determined by the anticipated dose or concentration of bromoform desired for final product or composition. The mass of bromoform dissolved in ethanol can be about 1 g to about 20 g. The volume of ethanol is kept at a minimum, not exceeding 20 mL. The solution of bromoform and ethanol is mixed with about 50 mL of an essential oil (e.g., a citrus oil) prior to mixing with 50 mL of MCT. This solution is mixed with canola oil to reach a final dilution, about 890 mL to yield 1 L of the oil-based composition.

Example 5: Synthesis of Water-Based Composition, Formulation No. 19

A general schematic on how to prepare the water-based composition is shown in FIG. 2. Provided is a synthesis to yield about 20 L of the water-based composition having a bromoform concentration of about 0.75 wt %. 150 g (about 52 mL) of bromoform is combined with 10 mL ethanol prior to being combined with 1000 mL of MCT, yielding an oil active component. The oil active component is vigorously mixed. Separately, an aqueous component is prepared by combining 20 g of xanthan gum and 500 mL of water and vigorously mixing and blending the two components. The xanthan gum mixture is poured into about 18 L of water. 472 g of Tween is added to the aqueous component and mixed. The oil-active component and the aqueous component are combined and vigorously mixed; thereafter, the combined oil-active component and aqueous component are subjected to ultrasonication for 15 minutes to produce the final water-based composition.

Similar compositions can be produced with different dosing through adjusting the mass of bromoform used. For example, a similar composition with a dose concentration of bromoform of about 0.1 wt % can be prepared through adding about 20 g of bromoform to ethanol.

Example 6: Synthesis of Solid Composition, Formulation No. 20

A general schematic on how to prepare the solid composition is shown in FIG. 3. Provided is a synthesis to yield about 6.5 kg of the solid composition. About 159 g (55 ml) of bromoform is combined with about 100 mL ethanol prior to combining with about 300 mL of MCT. Separately, 4125 g of milk powder is vigorously mixed with about 5000 g of water. Separately, about 2300 g of gelatin is vigorously mixed with 9000 g of water. The milk powder mixture and the bromoform mixture are combined, followed by being combined with the gelatin mixture. The mixture of all components is blended together and mixed vigorously until the mixture is almost set (e.g., comprises some flow). The mixture is then poured into a tray or mold, and cooled in a fridge. Upon cooling, the set mixture is minced. The minced mixture is then dried, optionally with the addition of heat, to evaporate at least 95 wt % of the water in the mixture. The resulting dry mixture is ground or pulverized to yield powdered solid composition.

In some embodiments, the composition can be utilized as a semi-solid composition through omitting the drying and grinding steps.

Example 7: Synthesis of Solid Composition with Agar

A general schematic on how to prepare the solid composition is shown in FIG. 4. Provided is a synthesis to yield about 7.5 kg of the solid composition. About 89.4 g of bromoform is combined with about 232 mL of MCT. Separately, about 4640 g of milk powder is vigorously mixed with 2700 g of water. Separately, about 1390 g of agar and 773 g of corn flour are combined and vigorously mixed with about 1550 g of water at a temperature of about 1° C. to about 10° C. The agar mixture is hydrated in the water for about 30 minutes prior to bringing the mixture to a boil and then subsequently simmering it for about 20 minutes. The bromoform mixture, the milk powder mixture, and the agar mixture are blended together and vigorously mixed. About 387 g of xanthan gum is added to the combined mixture and the entire mixture is mixed until it is almost set (e.g., comprises some flow). The mixture is then poured into a tray or mold, and cooled in a fridge. Upon cooling, the set mixture is minced. The minced mixture is then dried, optionally with the addition of heat, to evaporate at least 95 wt % of the water in the mixture. The resulting dry mixture is ground or pulverized to yield powdered solid composition.

In some embodiments, the composition is provided as a semi-solid composition through omitting the drying and grinding steps.

Example 8: Synthesis of Semi-Solid Composition (aqueous Gel)

A general schematic on how to prepare the semi-solid composition is shown in FIG. 5 To form about 1 kg of an aqueous gel, an aqueous component comprising 20 g of xanthan gum blended and mixed with 270 g of water. 400 g of Tween is added to the aqueous component. Separately, an oil-active component is prepared comprising 150 g of bromoform dissolved in about 10 g of ethanol and mixed with 150 g of MCT. The aqueous and oil-active components are combined and blended together and vigorously mixed. The resulting composition is subjected to ultrasonication for about 15 minutes to yield an emulsion. The emulsion can be combined with water at a later stage (for example, 20 L of water) yield an aqueous-gel composition with a concentration of bromoform of 7.5 mg/mL.

Example 9: In Vitro Methane Reduction Measurements: In Vitro Fermentation (IVFT)

Feed substrate, oaten chaff, was added to 50 mL vials one day prior to performance of the IVFT assay and left in an anaerobic chamber to remove any oxygen. On the day of the IVFT assay, rumen fluid and digesta was collected from fistulated sheep (UWA ethics approval 2021/ET001086) and taken immediately to the lab where it was strained to remove large feed particles. The rumen fluid and digesta was moved into an anaerobic chamber and mixed with a buffer. In the anaerobic chamber, a composition as provided in Table 1 was added to the vial containing the feed substrate. Rumen inoculum was added to the vials. The mixture in the vial was incubated for 24 hours. Gas production was measured using a pressure transducer, and subsamples of the gas were taken for methane quantification through gas chromatography. Total gas production was measured to provide an indicate of overall microbial fermentation. In some cases, fermentation end-products like volatile fatty acids (VFA) and ammonia were measured from the liquid phase. Each composition as provided in Table 1 was tested in triplicate and compared directly to a batch of oaten chaff control or the carrier only (e.g., a composition without the bromoform active.

For all compositions of the disclosure tested, the differences between formulations were analyzed by one-way ANOVA in JMIP 15.2.0 (SAS Institute, Inc) with the Tukey-Kramer HSD post-hoc test to compare means.

The results of the IVFT assay as determined for various concentrations (e.g., dose) of bromoform in the compositions provided in Table 1 are provided in FIG. 8 through FIG. 12.

Example 10: In Vitro Methane Reduction Measurements: Rusitec Experiment

Rumen fluid and digesta collected from fistulated sheep (UWA ethics approval 2021/ET001086) was mixed with buffer and added to 500 mL volume fermenters. Feed (e.g., oaten chaff) was included in the fermenters in two nylon bags (15 g of feed each). Feed in one of the two nylon bags was refreshed each day of the course of the experiment. A constant flow of buffer into the fermenters was used to maintain normal rumen pH of 6.0-7.0. The first seven days of the experiment are a pre-treatment period, for the system to stabilize. On day eight of the experiment, the feed is combined with a composition of the disclosure as provided in Table 1, where the composition can have varying concentration (e.g., dose) of bromoform. During each of day eight through day twenty-one of the experiment, the composition of the disclosure was added to the nylon bag being refreshed each day. The gas produced by each fermenter was collected and measured daily and samples were taken for methane quantification through gas chromatography. Samples of the fermentation fluid were collected three times through the course of the experiment for analysis of volatile fatty acids and ammonia.

The results of the Rusitec experiment as determined for various concentrations (e.g., dose) of bromoform in the compositions provided in Table 1 are provided in FIG. 13 through FIG. 15.

Example 11: In Vivo Methane Production Measurements: Respiration Chamber

A composition of the disclosure as provided in Table 1 is combined with a feed for a ruminant (e.g., pellet). A ruminant is administered the feed comprising a predetermined concentration of bromoform in a respiration chamber. The ruminant is maintained inside the respiration chamber for a period of 24 hours up to 48 hours. The respiration chamber is the gold standard, as known in the art, and detects and quantifies methane expelled from the ruminant.

Example 12: Oil Composition Coated on Total Mixed Ration and Administration Thereof An oil-based composition of the disclosure as provided in Table 1 is provided. 10 mL of the oil-based composition with varying concentration of bromoform in the oil composition (e.g., 1.25 g/L, 3.33 g/L, 5.83 g/L) is coated (e.g., dispersed) onto) 12 kg of mixed ration for administering to a ruminant in a feedlot. FIG. 6 shows examples of an oil-based composition combined with feed for a ruminant (e.g., mixed over total mixed ration, mixed over pellets, pressed in pellets).

Example 13: Oil Composition with a Supplement Pellet and Administration Thereof An oil-based composition of the disclosure as provided in Table 1 is provided in varying concentration of bromoform in the oil composition (e.g., 3 g/L, 4 g/L, 8 g/L, 14 g/L, 16 g/L). 25 mL of the oil composition is mixed with 1 kg of pellet supplement such that the oil composition coats the surface of the pellet.

Alternatively, 25 mL of the oil composition is pressed inside a total of 1 kg of pellet supplement.

A free grazing or a feedlot ruminant is administered about 2 kg of the pellet supplement comprising the oil composition per day.

FIG. 6 shows examples of an oil-based composition combined with feed for a ruminant (e.g., mixed over total mixed ration, mixed over pellets, pressed in pellets).

Example 14: Solid Composition Mixed Over Supplement Pellet

A solid composition of the disclosure as provided in Table 1 is provided in varying concentration of bromoform (e.g., 10 g/kg, 30 g/kg, 50 g/kg bromoform per kilogram of solid composition). 10 g of the solid composition is mixed among 2 kg of pellet supplements and about 50 mL of water to coat and stick the solid composition (e.g., powder form) on the pellet. The pellet comprising the bioactive coating are administered to free grazing ruminant. FIG. 7 shows examples of a solid composition combined with feed for a ruminant (e.g., mixed over supplement pellet, mixed in a mineral mix, mixed over a total mixed ration). In some embodiments, a total mixed ration comprises a mineral mix.

Example 15: Solid Composition with Mineral Mix

A solid composition of the disclosure as provided in Table 1 is provided in varying concentration of bromoform (e.g., 25 g bromoform per kg of solid composition). A mineral mix for a free-grazing ruminant with a body weight of about 300 kg is prepared such that 9 g of the solid composition and 900 g of dried distillers grain is mixed into a mineral mix for daily consumption (900 g DDG and 9 g the solid composition per head per day).

Alternatively, the prepared mineral mix is further combined with the total mixed ration, such that the ruminant is administered about 11 kg of the feed per day.

FIG. 7 shows examples of a solid composition combined with feed for a ruminant (e.g., mixed over supplement pellet, mixed in a mineral mix, mixed over a total mixed ration). In some embodiments, a total mixed ration comprises a mineral mix.

Example 16: Water Composition in Trough

A water-based composition of the disclosure as provided in Table 1 is provided in varying concentration of bromoform (e.g., 1 g/L, 3.75 g/L, 7.5 g/L, 15 g/L grams bromoform per L of water composition). For preparing 20 L of water comprising the water-based composition for administration to hard-to-reach, extensive grazing and rangeland cattle, 8 L of the water-based composition is diluted with 12 L of water. 20 L batches are created for expansive grazing cattle or cattle situated in dry environmental conditions (e.g., humidity of 30% or less).

The composition comprising 8 L of the water-based composition and 12 L of water can be used to create aliquots of 100 mL, where 40 mL of it is the water-based composition, for combination into every 10 L of water for administration to a ruminant through troughs.

Example 17: Administration of Consumable Composition to a Ruminant

A composition of the disclosure as provided in Table 1 is provided. The composition is combined with a pellet, a mineral mix, a total mix ration, or a trough depending on the nature of the composition (e.g., oil-based, water-based, solid) in accordance with Examples 11-15. The concentration, or dose, of bromoform in each composition may be adjusted depending on the target dose. The composition combined with the feed or water is provided to the ruminant for ingestion. The ruminant ingests at least a portion, or all, of the feed or water comprising the composition of the disclosure.

Example 18: Measurement of Feed Intake as a Proxy for Palatability

A composition of the disclosure as provided in Table 1 is provided comprising a taste enhancing agent. 9 heifers were provided about 10-16 kg of EasyBeef pellets (1.1-1.8 kg of EasyBeef pellets per head) not comprising the composition is provided to a ruminant per day for 10 days. Feeding behavior was recorded daily on video for a retrospective analysis. In addition to the pellets, the ruminants had free access to water and pasture (kikuyu and clover) and were provided with fresh oaten hay daily. After the 10 day adjustment period, the ruminant is weighed, body condition is scored, and samples of blood and rumen fluid are collected. Following the adjustment period, a targeted 16 kg of feed comprising the composition of the disclosure is provided to the ruminant each day for 2 weeks. At the end of the two-week sampling period, the ruminant is weighed, body condition scored, samples of blood and rumen fluid are collected. The ruminant is adjusted again by being fed plain pellets (16 kg per day) for about 1-2 weeks prior to sampling another composition of the disclosure.

The blood samples were centrifuged, and plasma and serum removed and frozen. The pH of the rumen fluid was measured immediately after collection using pH paper, and samples were preserved, one sample in 25% (v/v) orthophosphoric acid, to be analyzed for Volatile Fatty Acid (VFA) composition and the other containing only rumen fluid to be analyzed for NH3. The rumen samples were kept on ice and frozen soon after sampling.

Comparing the voluntary uptake of feed, the difference of average weight gain or rate of consumption for a baseline feed and a composition of the disclosure with or without a component (e.g., with plant based oil vs. without plant based oil)provides insight on palatability of a composition. All compositions were voluntarily ingested by the ruminants. A ruminant voluntarily ingests a greater proportion of feed, or ingests a feed at a higher rate, when the feed comprises a composition comprising a taste enhancing agent in comparison to when the feed comprises the composition without the taste enhancing agent. Alternatively, a ruminant voluntarily ingests a greater proportion of feed, or ingests a feed at a higher rate, when the feed comprises a composition comprising a lower MCT concentration and a taste enhancing agent in comparison to the when the feed comprises a higher concentration of MCT and a taste enhancing agent.

Example 19: Palatability Trial Using Formulation No. 11 Treatment 1 (4 g Bromoform Per Liter of Oil Composition)

After a 10-day adjustment period of plain pellets the animals were started on 18 kg of pellets treated with 25 mL of Treatment 1 per kg of pellet. The treatment was hand mixed in batches of 2 kg pellets, then poured into a larger bucket and hand mixed again to ensure even coating of pellets. The quantity of pellets offered was reduced to 10 kg on day 3 and then slowly increased to a total of 16 kg by the end of the treatment period.

The animals were initially started on 2 kg treated pellets each. On Day 1, all the animals ate fairly quickly and did not seem to be deterred by the treatment. On day 2, 4 out of the 9 animals had lost interest in the food and did not eat much of the pellets, while the other 5 finished off the food, consuming more than 2 kg per head. The time the animals took to completely finish all the food offered was between 35-60 minutes each day, while the untreated pellets in the intervening periods had usually been consumed faster (15-20 minutes). The acceptance of the treated pellets varied across the treatment period and among animals with some animals eating more on some days and not eating on other days. The dominance hierarchy seemed to play a role in level of acceptance of food, with the dominant animals pushing the smaller ones away from the food. Other factors like weather and prior hay consumption also likely played a role in acceptance of food. There were many rainy days during this treatment period.

Measurements of weight were taken the day after the two-week treatment period and showed that the animals had gained an average of 10.7 kg body weight compared to pre-treatment. The Angus heifers ate the most food and had gained the most weight, with animal #3 and #9 putting on 27 and 21 kg respectively. Animals #4 and #6 were very picky eaters and did not tend to eat much and had lower body condition scores (BCS). The results are illustrated in FIG. 19a.

Impression:

The acceptance of the treatment was variable and initially some of the animals did not eat much of the pellets. Most of the animals got used to the treatment within a few days and ate a significant amount every day and gained weight at the end of the treatment period. Although the animals were not as enthusiastic about the treatment as with the untreated pellets, they did voluntarily eat all of the treatment offered. Treatment 1 was palatable enough for the animals to ingest the treated pellets voluntarily.

Example 20: Palatability Trial Using Formulation No. 11 Treatment 2 (8 g Bromoform Per Liter of Oil Composition)

Treatment 2 was mixed in with the pellets the same as Treatment 1, at a concentration of 25 mL per kg of pellets, hand mixed in 2 kg batches. Treatment period started with a total of 10 kg pellets (250 mL treatment total) per day, and was increased to 12 kg (300 mL treatment total) based on level of acceptance. On day 9 of the treatment period 2 a sweet-smelling masking agent was added to 12 kg treated pellets at a concentration of 2.5 mL per kg. On the following days of Treatment 2 (days 10-14) the masking agent was mixed in with half (6 kg) of the treated pellets and offered to the animals in a separate trough to compare preference with unmasked treated pellets (Table 2).

The food intake was variable between the animals and the dominant ones (#9 and #3) continued to be the ones that ate most of the food. Few of the animals did not eat anything on the first day and ate a small amount the next day. Most of the animals stopped eating before all the treated pellet were consumed and it took approximately 35-60 minutes before the rest would stop eating. The amount of food offered was increased to 12 kg by day 3 and was not increased further as the animals did not finish all of the treated pellets, so 12 kg was the maximum cut-off. On day 9 of the treatment, a sweet-smelling masking agent provided by Rumin8 was added to the treated pellets to increase acceptance. The animals did not show an immediate increase in acceptance with the masking agent on day 9. On the following days (day 10-14), the masking agent was added to half the treated pellets and the other half was left without any masking to test preference. Both the masked and unmasked pellets were offered at the same time in separate troughs. It was not obvious at first but became clear in the following days that the animals had a slight preference for pellets with the masking agent. Interestingly, even though the masking agent increased the likelihood of the animal eating the treated pellets, it did not increase the amount of pellets consumed. In other words, the masking agent appeared to attract the animals to the food, but not increase the uptake amount.

After treatment period 2, the heifers had gained an average of 25±10 kg body weight, compared to the weight measured after treatment period 1. The actual amount of hay provided and consumed, and the amount of pasture available in the paddock is unknown, but as the weather warmed over the weeks, more pasture grew in the paddock. The results are illustrated in FIG. 19b.

Impression:

Treatment 2 was the least accepted of all the treatments tested during the trial with the animals consuming a maximum of 10-12 kg of treated pellets daily. The animals seemed to prefer pellets mixed with the sweet-smelling masking agent than without, but it did not help with increasing the amount of food consumed. Once again, this was still palatable enough to be voluntarily consumed with plenty of free-grazing pasture around.

Example 21: Palatability Trial Using Formulation No. 10 Treatment 3 (Chunks Vs. Powder Vs. Granules)

Treatment 3 was initially in the form of rubbery chunks of a caseous substance which was rubbed onto the pellets by hand, at a concentration of 10 g/kg pellet, starting with a total of 12 kg pellets (120 g treatment). The chunks did not mix evenly with the pellets and tended to fall to the bottom of the troughs. On day 1 of treatment, the animals finished the offered food fairly quickly but left behind a large number of chunks of the treatment at the bottom of the trough. A small amount of flavor enhancing agent was mixed in with the treatment from day 2 onwards, to potentially flavor the treatment residue and increase acceptance and intake of the treatment. All of the animals ate the treated pellets quickly, finishing the food within 15 minutes on most days. The food offered was increased to 16 kg by day 4 and maintained throughout treatment period 3. On day 5, with the availability of more dried product, the treatment type was changed from chunks to small granules which adhered better to the pellets but were still not evenly coating the pellets and would fall through to the bottom of the troughs. Some of the animals were observed licking the treatment off the troughs and they also had greater saliva production. The last formulation was in powdered form, used from day 9 onwards, and which adhered to the pellets better and coated them more evenly.

The sampling was conducted at the end of treatment period 3, but unfortunately the cattle could not be weighed due to operational issues. It can be expected that all of the animals gained weight as they had been eating very well and had higher body condition scores. The results are illustrated in FIG. 19c.

Impression:

Treatment 3 was overall very well accepted and rapidly ingested by the animals, with some observed licking the treatment off the bottom of the troughs. It is possible the addition of the flavor enhancing agent made the treatment highly appetizing for the animals. The fine powder formulation was superior to the others in terms of sticking to and evenly coating the pellets.

Example 22: Palatability Trial Using Formulation No. 25 and Formulation No. 26 Treatment 4 (No MSG Vs. MSG, Respectively)

Treatment period 4 started using a powdered formulation in two forms, 'T+' and 'T-'. One containing an extra ingredient (T+ type, 10% MSG) and the other without (T- type). The two types were tested against each other to determine if the animals preferred one over the other. Treatment period started with a total of 16 kg pellets, with 8 kg mixed with 45 gm of T+(5.625 g/kg pellet) and the other 8 kg with 45 gm of T−(5.625 g/kg pellet), offered in separate troughs. Both the treatment types were hand mixed with the EasyBeef pellets in batches of 2 kg and approximately 150 ml water was added while mixing to improve adherence of treatment powder to pellet surface. After the addition of water, the treatment evenly coated the pellets with only a small amount falling to the bottom of the troughs.

The animals ate 16 kg treated pellets everyday of the treatment period and finished the offered food within approximately 15 minutes daily. Whereas at day 1 and 2, the cows seemed to prefer the T+ form, this became less obvious for the duration of the 2-week period. Therefore, overall there was no obvious preference of one type of treatment over the other, with both types being consumed equally quickly. After all the pellets were consumed, some of the animals were observed licking the bottom of the troughs, containing small amounts of residual treatment powder. The results are illustrated in FIG. 19d.

Impression

The enthusiastic feeding behavior and fast consumption time suggests high palatability of the treatments and no difference in preference between the two types. The treatment sticks to the pellets well and evenly coats it when mixed with a small amount of water.

Example 23: Palatability Trial Using Formulation No. 23, Treatment 6 (4 g Bromoform Per Liter of Oil Composition with Canola Oil Treatment period 6 began using the oil formulation mixed with the EasyBeef pellets at a concentration of 25 ml/kg pellet. The treatment was hand mixed in batches of 2 kg to ensure even coating. The animals were offered 16 kg of treated pellets every day of the treatment period. On day 1 the animals had been given hay just before the treatment pellets were offered and all except 2 of the animals did not notice the pellets in the trough as they were busy eating hay. The troughs containing the pellets were then moved closer to the animals and as soon as they noticed all of them moved to the troughs and quickly finished the treatment and went back to consuming hay. The 2 animals that were the first to eat the pellets ate a disproportionately greater amount of treated pellets and as a result lost their appetite the next day and did not eat any pellets. The animals, on most days, ate all of the offered pellets within 15 minutes and some bullying from the dominant animals towards the others was observed. The results are illustrated in FIG. 19e.

Impression

The animals swiftly consumed all of the food offered, every day, during the treatment period. It can be safely inferred from the feeding behaviour that the animals were not deterred by the smell or taste of the oil treatment and preferred eating the coated pellets, even over the oaten hay provided. Although the treatment was highly accepted by the animals, it is important to note that when the treated pellets are consumed in quantities greater than 3 kg per animal, it tends to lead to a reduction in appetite on the following days.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby. The section headings used herein are for organizational purposes only and are not to be construed as limiting the subject matter described.

What is claimed is:

1. A consumable composition for methane reduction in a ruminant, comprising:
   a) bromoform, in an amount of about 0.001 wt % to about 8 wt %;
   b) a medium chain triglyceride (MCT), in an amount of about 3 wt % to about 10 wt %; and
   c) a plant-based oil, wherein a ratio of the MCT to the plant-based oil is about 3:97 to about 50:100;
   wherein the bromoform is not derived from a biomass, and wherein the consumable composition reduces methane production more than an otherwise identical composition that lacks MCT.

2. The composition of claim 1, wherein a ratio of the bromoform to the MCT is about 1:99 to about 1:1.

3. The composition of claim 2, wherein the ratio of the bromoform to the MCT is about 10:90 to about 30:70.

4. The composition of claim 1, wherein the ratio of the MCT to the plant-based oil is about 3:97 to 10:90.

5. The composition of claim 4, wherein the ratio of the MCT to the plant-based oil is about 5:95.

6. The composition of claim 1, wherein the plant-based oil is a vegetable oil.

7. The composition of claim 6, wherein the vegetable oil comprises a canola oil.

8. The composition of claim 1, wherein the composition further comprises an essential oil.

9. The composition of claim 1, wherein the composition further comprises water.

10. The composition of claim 9, wherein a ratio of water to the plant-based oil is about 5:95.

11. The composition of claim 10, wherein a ratio of MCT to the plant-based oil is about 5:95.

12. The composition of claim 1, wherein the composition is a concentrate.

13. The composition of claim 12, wherein the concentration of bromoform is about 0.1 wt % to about 1.7 wt %.

14. The composition of claim 1, wherein the composition comprises a feed.

15. The composition of claim 1, wherein the MCT comprises a mixture of a capric acid triglyceride and a caprylic acid triglyceride.

16. The composition of claim 15, wherein the MCT comprises caprylic acid triglyceride in an amount of about 50 wt % to about 80 wt %.

17. A method for reducing methane expelled from a ruminant, the method comprising: providing a ruminant the consumable composition of claim 1.

18. The method of claim 17, further comprising combining the consumable composition with a feed prior to providing the consumable composition to the ruminant.

19. The method of claim 18, wherein the feed comprises a pellet, a total mixed ration, a salt lick, or a mineral mix.

20. The method of claim 17, wherein providing a ruminant the consumable composition of claim 1 results in at least 60% reduction in expulsion of methane from the ruminant relative to an otherwise similar ruminant not administered the composition over the period of at least one day.

* * * * *